US008426173B2

(12) United States Patent
Bramucci et al.

(10) Patent No.: US 8,426,173 B2

(45) Date of Patent: Apr. 23, 2013

(54) METHOD FOR THE PRODUCTION OF 1-BUTANOL

(75) Inventors: Michael G. Bramucci, Boothwyn, PA (US); Dennis Flint, Newark, DE (US); Edward S. Miller, Jr., Knoxville, TN (US); Vasantha Nagarajan, Wilmington, DE (US); Natalia Sedkova, Cherry Hill, NJ (US); Manjari Singh, West Chester, PA (US); Tina K. Van Dyk, Wilmington, DE (US)

(73) Assignee: Butamax (TM) Advanced Biofuels LLC, Wilmington, DE (US)

( * ) Notice: Subject to any disclaimer, the term of this patent is extended or adjusted under 35 U.S.C. 154(b) by 898 days.

(21) Appl. No.: 12/110,503

(22) Filed: Apr. 28, 2008

(65) Prior Publication Data

US 2008/0274524 A1 Nov. 6, 2008

Related U.S. Application Data

(60) Provisional application No. 60/915,455, filed on May 2, 2007.

(51) Int. Cl.
*C12P 7/16* (2006.01)

(52) U.S. Cl.
USPC .......................................... 435/160; 435/165

(58) Field of Classification Search ........................ None
See application file for complete search history.

(56) References Cited

U.S. PATENT DOCUMENTS

| | | | | |
|---|---|---|---|---|
| 2,198,104 | A * | 4/1940 | Carnarius | 435/150 |
| 4,424,275 | A | 1/1984 | Levy | |
| 4,520,104 | A | 5/1985 | Heady et al. | |
| 4,568,643 | A | 2/1986 | Levy | |
| 5,063,156 | A | 11/1991 | Glassner et al. | |
| 5,192,673 | A | 3/1993 | Jain et al. | |
| 5,210,032 | A | 5/1993 | Kashket et al. | |
| 5,424,202 | A | 6/1995 | Ingram et al. | |
| 6,358,717 | B1 | 3/2002 | Blaschek et al. | |
| 6,835,820 | B2 | 12/2004 | Cannon et al. | |
| 6,960,465 | B1 | 11/2005 | Papaoutsakis et al. | |
| 2002/0028492 | A1 | 3/2002 | Lenke et al. | |
| 2002/0182690 | A1 | 12/2002 | Cannon et al. | |
| 2004/0234649 | A1 | 11/2004 | Lewis et al. | |
| 2007/0259411 | A1 | 11/2007 | Bramucci et al. | |
| 2008/0124774 | A1 | 5/2008 | Bramucci et al. | |
| 2008/0138870 | A1 | 6/2008 | Bramucci et al. | |
| 2008/0182308 | A1 * | 7/2008 | Donaldson et al. | 435/160 |

FOREIGN PATENT DOCUMENTS

| | | | |
|---|---|---|---|
| AU | 620802 | | 2/1992 |
| CA | 2039245 | | 10/1991 |
| EP | 0 112 459 | A1 | 7/1984 |
| EP | 0 282 474 | A1 | 9/1988 |
| EP | 0 315 949 | A2 | 5/1989 |
| EP | 1 149 918 | A1 | 10/2001 |
| JP | 1986209594 | | 9/1986 |
| JP | 1988017695 | | 4/1988 |
| JP | 1988102687 | | 5/1988 |
| JP | 1988254986 | | 10/1988 |
| WO | WO 9002193 | A1 | 3/1990 |
| WO | WO 9851813 | A1 | 11/1998 |
| WO | WO 2007/041269 | A2 | 4/2007 |
| WO | WO 2008/006038 | A2 | 1/2008 |
| WO | 2008052991 | | 5/2008 |
| WO | WO 2008/072920 | A1 | 6/2008 |
| WO | WO 2008/072921 | A1 | 6/2008 |

OTHER PUBLICATIONS

Stim-Herndon et al., Gene, 1995, vol. 154, p. 81-85.*

EcoCyc database for *E. coli* K-12, 1 page.*

International Preliminary Report on Patentability in corresponding PCT/US2008/061855 mailed Nov. 12, 2009.

Butanols, Ullmann'S Encyclopedia of Industrial Chemistry, 6th Edition, 2003, vol. 5:716-719.

Girbal Regulation of Solvent Production in *Clostridium acetobutylicum*, et al., Trends in Biotechnology, 1998, vol. 16:11-16.

Amartey et al., Effects of Temperature and Medium Composition on the Ethanol Tolerance of *Bacillus stearothermophilus* LLD-15, Biotechnol. Lett., 1991, vol. 13:627-632.

Herrero et al., Development of Ethanol Tolerance in *Clostridium thermocellum*: Effect of Growth Temperature, Appl. Environ. Microbiol., 1980, vol. 40:571-577.

Brown et al., The Effects of Temperature on the Ethanol Tolerance of the Yeast, *Saccharomyces uvarum*, Biotechnol. Lett., 1982, vol. 4:269-274.

Van Uden, Effects of Ethanol on the Temperature Relations of Viability and Growth in Yeast, CRC Crit. Rev. Biotechnol., 1984, vol. 1:263-273.

Harada, On the Butanol-Rich Production in Acetone-Butanol Fermentation of Molasses, (Part 2) Temperature) Hakko Kyokaishi, 1962, vol. 20:155-156.

Jones et al., Acetone-Butanol Fermentation Revisited, Microbiol. Rev., 1986, vol. 50:484-524.

Baer et al., Effect of Butanol Challenge and Temperature on Lipid Composition and Membrane Fluidity of Butanol-Tolerant *Clostridium acetobutylicum*, Applied and Environmental Microbiology, 1987, vol. 53:2854-2861.

Inui et al., Expression of *Clostridium acetobutylicum* Butanol Synthetic Genes in *Escherichia coli*, Applied and Microbiology and Biotechnology, 2008, vol. 77:1305-1316.

Bermejo et al., Expression of *Clostridium acetobutylicum* ATCC 824 Genes in *Escherichia coli* for Acetone Production and Acetate Detoxification, Applied and Environmental Microbiology, 1998, vol. 64:1079-1085.

M. A. Casadei et al., Heat Resistance of *Bacillus cereus, Salmonella typhimurium* and *Lactobacillus delbrueckii* in Relation to PH and Ethanol, International Journal of Food Microbiology, 2001, vol. 63:125-134.

(Continued)

*Primary Examiner* — Kade Ariani

(74) *Attorney, Agent, or Firm* — Christine M. Lhulier

(57) ABSTRACT

A method for the production of 1-butanol by fermentation using a microbial production host is disclosed. The method employs a reduction in temperature during the fermentation process that results in a more robust tolerance of the production host to the butanol product.

21 Claims, 1 Drawing Sheet

OTHER PUBLICATIONS

Cornillot et al., The Genes for Butanol and Acetone Formation in *Clostridium acetobutylicum* ATCC 824 Reside on a Large Plasmid Whose Loss Leads to Degeneration of the Strain, Journal of Bacteriology, 1997, vol. 179:5442-5447.

Fontaine et al., Molecular Characterization and Transcriptional Analysis of ADHE2, The Gene Encoding the NADH-Dependent Aldehyde/Alcohol Dehydrogenase Responsible for Butanol Production in Alcohologenic Cultures of *Clostridium acetobutylicum*, Journal of Bacteriology, 2002, vol. 184:821-830.

David R. Woods, The Genetic Engineering of Microbial Solvent Production, Tibtech, 1995, vol. 13:259-264.

Harris, Latonia M. et al., Characterization of Recombinant Strains of the *Clostridium acetobutylicum* Butyrate Kinase Inactivation Mutant: Need for New Phenomenological Models for Solventogenesis and Butanol Inhibition, Biotechnology and Bioengineering, 2000, pp. 1-11, vol. 67, No. 1, John Wiley & Sons, Inc.

Durre, P., New Insights and Novel Developments in *Clostridial* Acetone/Butanol/Isopropanol Fermentation, Applied Microbiology and Biotechnology, 1998, pp. 639-648, vol. 49, No. 6, Springer-Verlag.

Berovic et al., "Influence of temperature and carbon dioxide on fermentation of cabernet sauvignon must", Food Technol. Biotechnol., vol. 41, No. 4 pp. 353-359 (2003).

Poulsen et al., "Purification and properties of *Saccharomyces cerevisiae* acetolactate synthase from recombinant *Escherichia coli*", Eur. J. Biochem., vol. 185, pp. 433-439 (1989).

Renna et al., "Regulation of the *Bacillus subtilis* alsS, alsD, and alsR genes involved in post-expoential-phase production of acetoin", J. Bacteriology, vol. 175, No. 12, Jun. 1993, pp. 3863-3875.

Boynton, et al., Cloning, Sequencing, and Expression of Clustered Genes Encoding beta-Hydroxybutyryl-Coenzyme A (CoA) Dehydrognease . . . , J. Bacteriol. 178:3015-3024, 1996.

Branden, et al., Prediction, Engineering, and Design of Protein Structures, Introduction to Protein Structure, Garland Publishing Inc., New York, NY, p. 247, 1991.

Buckel, Special *Clostridia* Enzymes and Fermentation Pathways, Handbook on *Clostridia*, CRC Press, Pub. Mar. 29, 2006, pp. 177, 182-184, and 212-220.

Durre, et al., Transcriptional Regulation of Solventogenesis in *Clostridium acetobutylicum*, J. Mol. Microbiol. Biotechnol. 4:295-300, 2002.

Hoffmeister, et al., Mitochondrial trans-2-Enoyl-CoA Reductase of Wax Ester Fermentation from *Euglena gracilis* Defines a New Family . . . , J. Biol. Chem. 280:4329-4338, 2005.

Stewart, A Chemist's Perspective on the Use of Genetically Engineered Microbes as Reagents for Organic Synthesis, Blotechnol. Genet. Eng. Rev. 14: 67-143, 1997.

Human mitochondrial 2-enoyl thioester reductase (CGI-63), Crystal structure 1ZSY, RCSB Protein Data Bank (www.pbd.org), retrieved Sep. 8, 2010.

* cited by examiner

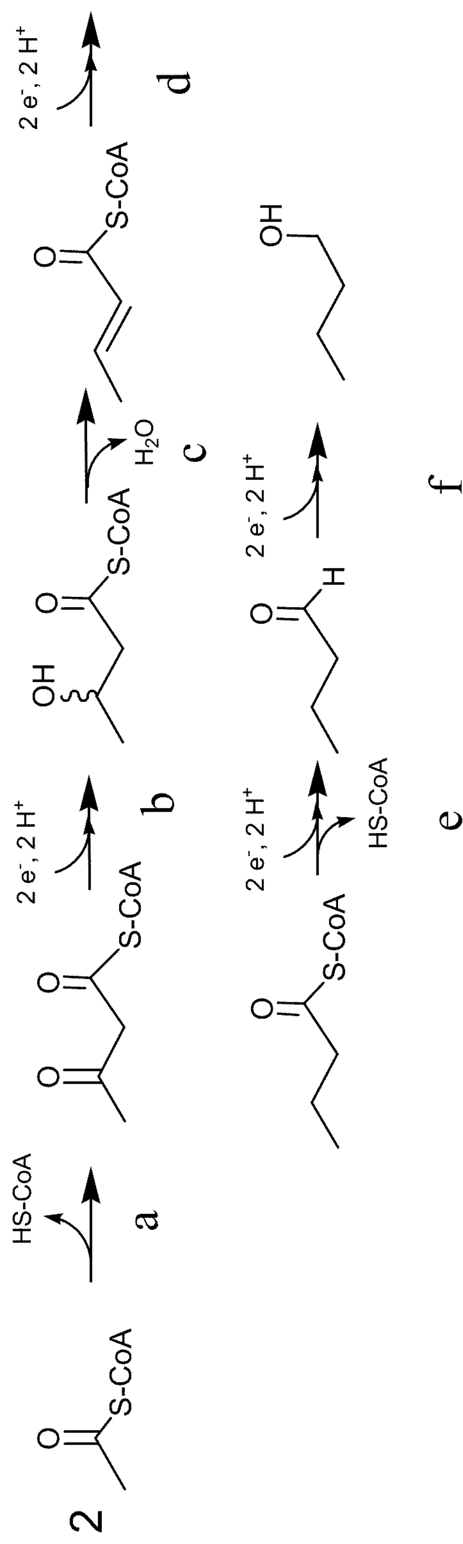
2
S-CoA
HS-CoA
a
2 e⁻, 2 H⁺
b
H2O
c
2 e⁻, 2 H⁺
d
HS-CoA
e
2 e⁻, 2 H⁺
f
OH

METHOD FOR THE PRODUCTION OF 1-BUTANOL

This Application claims priority to U.S. Provisional Application 60/915,455 filed May 2, 2007.

FIELD OF THE INVENTION

The invention relates to a method for the production of 1-butanol by fermentation using a recombinant microbial host. Specifically, the method employs a decrease in temperature during fermentation that results in more robust tolerance of the production host to the 1-butanol product.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of 1-butanol are known, such as the Oxo Process, the Reppe Process, and the hydrogenation of crotonaldehyde (*Ullmann's Encyclopedia of Industrial Chemistry,* $6^{th}$ edition, 2003, Wiley-VCHVerlag GmbH and Co., Weinheim, Germany, Vol. 5, pp. 716-719). These processes use starting materials derived from petrochemicals and are generally expensive and are not environmentally friendly. The production of 1-butanol from plant-derived raw materials would minimize greenhouse gas emissions and would represent an advance in the art.

Methods of producing 1-butanol by fermentation are also known, where the most popular process produces a mixture of acetone, 1-butanol and ethanol and is referred to as the ABE process (Blaschek et al., U.S. Pat. No. 6,358,717). Acetone-butanol-ethanol (ABE) fermentation by *Clostridium acetobutylicum* is one of the oldest known industrial fermentations, and the pathways and genes responsible for the production of these solvents have been reported (Girbal et al., *Trends in Biotechnology* 16:11-16 (1998)). Additionally, recombinant microbial production hosts expressing a 1-butanol biosynthetic pathway have been described (Donaldson et al., copending and commonly owned U.S. patent application Ser. No. 11/527,995). However, biological production of 1-butanol is believed to be limited by butanol toxicity to the host microorganism used in the fermentation.

Some microbial strains that are tolerant to 1-butanol are known in the art (see for example, Jain et al. U.S. Pat. No. 5,192,673; Blaschek et al. U.S. Pat. No. 6,358,717; Papoutsakis et al. U.S. Pat. No. 6,960,465; and Bramucci et al., copending and commonly owned U.S. patent application Ser. Nos. 11/743,220, 11/761,497, and 11/949,793). However, biological methods of producing 1-butanol to higher levels are required for cost effective commercial production.

There have been reports describing the effect of temperature on the tolerance of some microbial strains to ethanol. For example, Amartey et al. (*Biotechnol. Lett.* 13(9):627-632 (1991)) disclose that *Bacillus stearothermophillus* is less tolerant to ethanol at 70° C. than at 60° C. Herrero et al. (*Appl. Environ. Microbiol.* 40(3):571-577 (1980)) report that the optimum growth temperature of a wild-type strain of *Clostridium thermocellum* decreases as the concentration of ethanol challenge increases, whereas the optimum growth temperature of an ethanol-tolerant mutant remains constant. Brown et al. (*Biotechnol. Lett.* 4(4):269-274 (1982)) disclose that the yeast *Saccharomyces uvarum* is more resistant to growth inhibition by ethanol at temperatures 5° C. and 10° C. below its growth optimum of 35° C. However, fermentation became more resistant to ethanol inhibition with increasing temperature. Additionally, Van Uden (*CRC Crit. Rev. Biotechnol.* 1 (3):263-273 (1984)) report that ethanol and other alkanols depress the maximum and the optimum growth temperature for growth of *Saccharomyces cerevisiae* while thermal death is enhanced. Moreover, Lewis et al. (U.S. patent Application Publication No. 2004/0234649) describe methods for producing high levels of ethanol during fermentation of plant material comprising decreasing the temperature during saccharifying, fermenting, or simultaneously saccharifying and fermenting.

Much less is known about the effect of temperature on the tolerance of microbial strains to 1-butanol. Harada (*Hakko Kyokaishi* 20:155-156 (1962)) discloses that the yield of 1-butanol in the ABE process is increased from 18.4%-18.7% to 19.1%-21.2% by lowering the temperature from 30° C. to 28° C. when the growth of the bacteria reaches a maximum. Jones et al. (*Microbiol. Rev.* 50(4):484-524 (1986)) review the role of temperature in ABE fermentation. They report that the solvent yields of three different solvent producing strains remains fairly constant at 31% at 30° C. and 33° C., but decreases to 23 to 25% at 37° C. Similar results were reported for *Clostridium acetobutylicum* for which solvent yields decreased from 29% at 25° C. to 24% at 40° C. In the latter case, the decrease in solvent yield was attributed to a decrease in acetone production while the yield of 1-butanol was unaffected. However, Carnarius (U.S. Pat. No. 2,198,104) reports that an increase in the butanol ratio is obtained in the ABE process by decreasing the temperature of the fermentation from 30° C. to 24° C. after 16 hours. However, the effect of temperature on the production of 1-butanol by recombinant microbial hosts is not known in the art.

There is a need, therefore, for a cost-effective process for the production of 1-butanol by fermentation that provides higher yields than processes known in the art. The present invention addresses this need through the discovery of a method for producing 1-butanol by fermentation using a recombinant microbial host, which employs a decrease in temperature during fermentation, resulting in more robust tolerance of the production host to the 1-butanol product.

SUMMARY OF THE INVENTION

The invention provides a method for the production of 1-butanol by fermentation using a recombinant microbial host, which employs a decrease in temperature during fermentation that results in more robust tolerance of the production host to the 1-butanol product.

Accordingly, the invention provides a method for the production of 1-butanol comprising:

a) providing a recombinant microbial production host which produces 1-butanol;
b) seeding the production host of (a) into a fermentation medium comprising a fermentable carbon substrate to create a fermentation culture;
c) growing the production host in the fermentation culture at a first temperature for a first period of time;
d) lowering the temperature of the fermentation culture to a second temperature; and
e) incubating the production host at the second temperature of step (d) for a second period of time;

whereby 1-butanol is produced.

BRIEF DESCRIPTION OF THE FIGURES AND SEQUENCE DESCRIPTIONS

The invention can be more fully understood from the following detailed description, FIGURE, and the accompanying sequence descriptions, which form a part of this application.

FIG. 1 shows the 1-butanol biosynthetic pathway. The steps labeled "a", "b", "c", "d", "e", and "f" represent the substrate to product conversions described below.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers

| Description | SEQ ID NO Nucleic acid | SEQ ID NO Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| Acetyl-CoA acetyltransferase from *Escherichia coli* | 128 | 129 |
| Acetyl-CoA acetyltransferase from *Bacillus subtilis* | 130 | 131 |
| Acetyl-CoA acetyltransferase from *Saccharomyces cerevisiae* | 132 | 133 |
| 3-Hydroxybutyryl-CoA dehydrogenase from *Clostridium acetobutylicum* ATCC 824 | 5 | 6 |
| 3-Hydroxybutyryl-CoA dehydrogenase from *Bacillus subtilis* | 134 | 135 |
| 3-Hydroxybutyryl-CoA dehydrogenase from *Ralstonia eutropha* | 136 | 137 |
| 3-Hydroxybutyryl-CoA dehydrogenase from *Alcaligenes eutrophus* | 138 | 139 |
| Crotonase from *Clostridium acetobutylicum* ATCC 824 | 7 | 8 |
| Crotonase from *Escherichia coli* | 140 | 141 |
| Crotonase from *Bacillus subtilis* | 142 | 143 |
| Crotonase from *Aeromonas caviae* | 144 | 145 |
| Putative trans-enoyl CoA reductase from *Clostridium acetobutylicum* ATCC 824 | 9 | 10 |
| Butyryl-CoA dehydrogenase from *Euglena gracilis* | 146 | 147 |
| Butyryl-CoA dehydrogenase from *Streptomyces collinus* | 148 | 149 |
| Butyryl-CoA dehydrogenase from *Streptomyces coelocolor* | 150 | 151 |
| Butyraldehyde dehydrogenase from *Clostridium beijerinckii* NRRL B594 | 11 | 12 |
| Butyraldehyde dehydrogenase from *Clostridium acetobutylicum* | 152 | 153 |
| Butanol dehydrogenase bdhB from *Clostridium acetobutylicum* ATCC 824 | 13 | 14 |
| Butanol dehydrogenase bdhA from *Clostridium acetobutylicum* ATCC 824 | 15 | 16 |
| Butanol dehydrogenase from *Clostridium acetobutylicum* | 152 | 153 |
| Butanol dehydrogenase from *Escherichia coli* | 154 | 155 |

SEQ ID NOs:17-44 are the nucleotide sequences of oligonucleotide primers used to amplify the genes of the 1-butanol biosynthetic pathway.

SEQ ID NOs:45-72 are the nucleotide sequences of oligonucleotide primers used for sequencing.

SEQ ID NOs:73-75 are the nucleotide sequences of oligonucleotide primers used to construct the transformation vectors described in Example 13.

SEQ ID NO:76 is the nucleotide sequence of the codon-optimized CAC0462 gene, referred to herein as CaTER.

SEQ ID NO:77 is the nucleotide sequence of the codon-optimized EgTER gene, referred to herein as EgTER(opt).

SEQ ID NO:78 is the nucleotide sequence of the codon-optimized ald gene, referred to herein as ald (opt).

SEQ ID NO:79 is the nucleotide sequence of the plasmid pFP988.

SEQ ID NO:'s 80-127, 160-185, and 190-207 are the nucleic acid sequences of cloning, sequencing, or PCR screening primers used for the cloning, sequencing, or screening of the genes of the 1-butanol biosynthetic pathway described herein, and are more fully described in Tables 4 and 5.

SEQ ID NO:156 is the nucleotide sequence of the cscBKA gene cluster.

SEQ ID NO:157 is the amino acid sequence of sucrose hydrolase (CscA).

SEQ ID NO:158 is the amino acid sequence of D-fructokinase (CscK).

SEQ ID NO:159 is the amino acid sequence of sucrose permease (CscB).

SEQ ID NO:186 is the nucleotide sequence of the codon optimized tery gene described in Example 21.

SEQ ID NO:187 is the amino acid sequence of the butyl-CoA dehydrogenase (ter) encoded by the codon optimized tery gene (SEQ ID NO:186).

SEQ ID NO:188 is the nucleotide sequence of the codon optimized aldy gene described in Example 21.

SEQ ID NO:189 is the amino acid sequence of the butyraldehyde dehydrogenase (ald) encoded by the codon optimized aldy gene (SEQ ID NO:188).

SEQ ID NO:208 is the nucleotide sequence of the template DNA used in Example 18.

DETAILED DESCRIPTION OF THE INVENTION

The present invention relates to a method for the production of 1-butanol using recombinant microorganisms that employs a decrease in temperature during fermentation, resulting in more robust tolerance of the production host to the 1-butanol product and therefore a higher titer of 1-butanol. The present invention meets a number of commercial and industrial needs. 1-Butanol is an important industrial commodity chemical with a variety of applications, where its potential as a fuel or fuel additive is particularly significant. Although only a four-carbon alcohol, butanol has an energy content similar to that of gasoline and can be blended with any fossil fuel. Butanol is favored as a fuel or fuel additive as it yields only $CO_2$ and little or no $SO_X$ or $NO_X$ when burned in the standard internal combustion engine. Additionally 1-butanol is less corrosive than ethanol, the most preferred fuel additive to date.

In addition to its utility as a biofuel or fuel additive, 1-butanol has the potential of impacting hydrogen distribution problems in the emerging fuel cell industry. Fuel cells today are plagued by safety concerns associated with hydrogen transport and distribution. 1-Butanol can be easily reformed for its hydrogen content and can be distributed through existing gas stations in the purity required for either fuel cells or vehicles.

Finally the present invention produces 1-butanol from plant derived carbon sources, avoiding the negative environmental impact associated with standard petrochemical processes for butanol production.

The following definitions and abbreviations are to be used for the interpretation of the claims and the specification.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

"ABE" is the abbreviation for the Acetone-Butanol-Ethanol fermentation process.

The term "1-butanol biosynthetic pathway" means the enzyme pathway to produce 1-butanol from acetyl-coenzyme A (acetyl-CoA).

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [*Enzyme Nomenclature* 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728 (SEQ ID NO:129), NC_000913 (SEQ ID NO:128); NCBI (National Center for Biotechnology Information) amino acid sequence, NCBI nucleotide sequence), *Clostridium acetobutylicum* (GenBank Nos: NP_349476.1 (SEQ ID NO:2), NC_003030 (SEQ ID NO:1); NP_149242 (SEQ ID NO:4), NC_001988 (SEQ ID NO:3), *Bacillus subtilis* (GenBank Nos: NP_390297 (SEQ ID NO:131), NC_000964 (SEQ ID NO:130)), and *Saccharomyces cerevisiae* (GenBank Nos: NP_015297 (SEQ ID NO:133), NC_001148 (SEQ ID NO:132)).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030 (SEQ ID NO:5)), *B. subtilis* (GenBank NOs: AAB09614 (SEQ ID NO:135), U29084 (SEQ ID NO:134)), *Ralstonia eutropha* (GenBank NOs: YP_294481 (SEQ ID NO:137), NC_007347 (SEQ ID NO:136)), and *Alcaligenes eutrophus* (GenBank NOs: AAA21973 (SEQ ID NO:139), J04987 (SEQ ID NO:138)).

The term "crotonase" refers to an enzyme that catalyzes the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:141), NC_000913 (SEQ ID NO:140)), *C. acetobutylicum* (GenBank NOs: NP_349318 (SEQ ID NO:8), NC_003030 (SEQ ID NO:6)), *B. subtilis* (GenBank NOs: CAB13705 (SEQ ID NO:143), Z99113 (SEQ ID NO:142)), and *Aeromonas caviae* (GenBank NOs: BAA21816 (SEQ ID NO:145), D88825 (SEQ ID NO:144)).

The term "butyryl-CoA dehydrogenase" refers to an enzyme that catalyzes the conversion of crotonyl-CoA to butyryl-CoA. Butyryl-CoA dehydrogenases may be either NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102

(SEQ ID NO:10), NC_003030 (SEQ ID NO:9))), *Euglena gracilis* (GenBank NOs: Q5EU90 SEQ ID NO:147), AY741582 SEQ ID NO:146)), *Streptomyces collinus* (GenBank NOs: AAA92890 (SEQ ID NO:149), U37135 (SEQ ID NO:148)), and *Streptomyces coelicolor* (GenBank NOs: CAA22721 (SEQ ID NO:151), AL939127 (SEQ ID NO:150)).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306 (SEQ ID NO:11)) and *C. acetobutylicum* (GenBank NOs: NP_149325 (SEQ ID NO:153), NC_001988 (SEQ ID NO:152)).

The term "butanol dehydrogenase" refers to an enzyme that catalyzes the conversion of butyraldehyde to 1-butanol, using either NADH or NADPH as cofactor. Butanol dehydrogenases are available from, for example, *C. acetobutylicum* (GenBank NOs: NP_149325 (SEQ ID NO:153), NC_001988 SEQ ID NO:152; note: this enzyme possesses both aldehyde and alcohol dehydrogenase activity); NP_349891 (SEQ ID NO:14), NC_003030 (SEQ ID NO:13); and NP_349892 (SEQ ID NO:16), NC_003030 (SEQ ID NO:15)) and *E. coli* (GenBank NOs: NP_417-484 (SEQ ID NO:155), NC_000913 (SEQ ID NO:154)).

The term "a facultative anaerobe" refers to a microorganism that can grow in both aerobic and anaerobic environments.

The term "carbon substrate" or "fermentable carbon substrate" refers to a carbon source capable of being metabolized by host organisms disclosed herein and particularly carbon sources selected from the group consisting of monosaccharides, oligosaccharides, polysaccharides, and one-carbon substrates or mixtures thereof.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "heterologous gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, an "isolated nucleic acid fragment" or "isolated nucleic acid molecule" or "genetic construct" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.,* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment disclosed herein. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

The 1-Butanol Biosynthetic Pathway

Carbohydrate utilizing microorganisms employ the Embden-Meyerhof-Parnas (EMP) pathway, the Entner-Doudoroff pathway and the pentose phosphate cycle as the central, metabolic routes to provide energy and cellular precursors for growth and maintenance. These pathways have in common the intermediate glyceraldehyde-3-phosphate and, ultimately, pyruvate is formed directly or in combination with the EMP pathway. Subsequently, pyruvate is transformed to acetyl-coenzyme A (acetyl-CoA) via a variety of means, including reaction with the pyruvate dehydrogenase complex, pyruvate-formate lyase, and pyruvate-ferredoxin oxidoreductase. Acetyl-CoA serves as a key intermediate, for example, in generating fatty acids, amino acids and secondary metabolites. The combined reactions of sugar conversion to acetyl-CoA produce energy (e.g. adenosine-5'-triphosphate, ATP) and reducing equivalents (e.g. reduced nicotinamide adenine dinucleotide, NADH, and reduced nicotinamide adenine dinucleotide phosphate, NADPH). NADH and NADPH must be recycled to their oxidized forms ($NAD^+$ and $NADP^+$, respectively). In the presence of inorganic electron acceptors (e.g. $O_2$, $NO_3^-$ and $SO_4^{2-}$), the reducing equivalents may be used to augment the energy pool; alternatively, a reduced carbon by-product may be formed. The production of ethanol and 1-butanol resulting from the fermentation of carbohydrate are examples of the latter. As described by Donaldson, supra, 1-butanol can be produced from carbohydrate sources by recombinant microorganisms comprising a complete 1-butanol biosynthetic pathway from acetyl-CoA to 1-butanol, as shown in FIG. 1."

This biosynthetic pathway, generally lacking in the microbial community due to the absence of genes or the lack of appropriate gene regulation, comprises the following substrate to product conversions:

a) acetyl-CoA to acetoacetyl-CoA, as catalyzed for example by acetyl-CoA acetyltransferase;

b) acetoacetyl-CoA to 3-hydroxybutyryl-CoA, as catalyzed for example by 3-hydroxybutyryl-CoA dehydrogenase;

c) 3-hydroxybutyryl-CoA to crotonyl-CoA, as catalyzed for example by crotonase;

d) crotonyl-CoA to butyryl-CoA, as catalyzed for example by butyryl-CoA dehydrogenase;

e) butyryl-CoA to butyraldehyde, as catalyzed for example by butyraldehyde dehydrogenase; and f) butyraldehyde to 1-butanol, as catalyzed for example by butanol dehydrogenase.

The pathway requires no ATP and generates $NAD^+$ and/or $NADP^+$, thus, balances with the central metabolic routes that generate acetyl-CoA. The ability of natural organisms to produce 1-butanol by fermentation is rare and exemplified most prominently by *Clostridium beijerinckii* and *Clostridium acetobutylicum*. The gene organization and gene regulation for *Clostridium acetobutylicum* has been described (L. Girbal and P. Soucaille, *Trends in Biotechnology* 216:11-16 (1998)). However, many of these enzyme activities are associated also with alternate pathways, for example, hydrocarbon utilization, fatty acid oxidation, and poly-hydroxyalkanoate metabolism. Thus, in providing a recombinant pathway from acetyl-CoA to 1-butanol, there exist a number of choices to fulfill the individual reaction steps, and the person of skill in the art will be able to utilize publicly available sequences to construct the relevant pathways. A listing of a representative number of genes known in the art and useful in the construction of the 1-butanol biosynthetic pathway are listed below in Table 2 and in Donaldson et al., copending and commonly owned U.S. patent application Ser. No. 11/527,995, incorporated herein by reference.

TABLE 2

Sources of 1-Buatnol Pathway Genes

| Gene | GenBank Citation |
|---|---|
| acetyl-CoA acetyltransferase | NC_000913 *Escherichia coli* K12, complete genome gi\|49175990\|ref\|NC_000913.2\|[49175990] |
| | NC_001988 *Clostridium acetobutylicum* ATCC 824 plasmid pSOL1, complete sequence gi\|15004705\|ref\|NC_001988.2\|[15004705] |
| | NC_000964 *Bacillus subtilis* subsp. *subtilis* str. 168, complete genome gi\|50812173\|ref\|NC_000964.2\|[50812173] |
| | NC_001148 *Saccharomyces cerevisiae* chromosome XVI, complete chromosome sequence gi\|50593503\|ref\|NC_001148.3\|[50593503] |
| | CP000017 *Streptococcus pyogenes* MGAS5005, complete genome gi\|71852596\|gb\|CP000017.1\|[71852596] |
| | NC_005773 *Pseudomonas syringae* pv. phaseolicola 1448A, complete genome |

TABLE 2-continued

Sources of 1-Buatnol Pathway Genes

| Gene | GenBank Citation |
|---|---|
| | gi\|71733195\|ref\|NC_005773.3\|[71733195] |
| | CR931997 *Corynebacterium jeikeium* K411 complete genome gi\|68262661\|emb\|CR931997.1\|[68262661] |
| 3-hydroxybutyryl-CoA dehydrogenase | NC_003030 *Clostridium acetobutylicum* ATCC 824, complete genome gi\|15893298\|ref\|NC_003030.1\|[15893298] |
| | U29084 *Bacillus subtilis* (mmgA), (mmgB), (mmgC), and citrate synthase III (mmgD) genes, complete cds, and (mmgE) gene, partial cds gi\|881603\|gb\|U29084.1\|BSU29084[881603] |
| | NC_007347 *Ralstonia eutropha* JMP134 Raeut01_1, whole genome shotgun sequence gi\|45517296\|ref\|NZ_AADY01000001.1\|[45517296] |
| | J04987 *A. eutrophus* beta-ketothiolase (phbA) and acetoacetyl-CoA reductase (phbB) genes, complete cds gi\|141953\|gb\|J04987.1\|AFAKTLAACA[141953] |
| | NC_004129 *Pseudomonas fluorescens* Pf-5, complete genome gi\|70728250\|ref\|NC_004129.6\|[70728250] |
| | NC_000913 *Escherichia coli* K12, complete genome gi\|49175990\|ref\|NC_000913.2\|[49175990] |
| | NC_004557 *Clostridium tetani* E88, complete genome gi\|28209834\|ref\|NC_004557.1\|[28209834] |
| | NC_006350 *Burkholderia pseudomallei* K96243 chromosome 1, complete sequence gi\|53717639\|ref\|NC_006350.1\|[53717639] |
| | NC_002947 *Pseudomonas putida* KT2440, complete genome gi\|26986745\|ref\|NC_002947.3\|[26986745] |
| crotonase | NC_000913 *Escherichia coli* K12, complete genome gi\|49175990\|ref\|NC_000913.2\|[49175990] |
| | NC_003030 *Clostridium acetobutylicum* ATCC 824, complete genome gi\|15893298\|ref\|NC_003030.1\|[15893298] |
| | Z99113 *Bacillus subtilis* complete genome (section 10 of 21): from 1807106 to 2014934 gi\|32468758\|emb\|Z99113.2\|BSUB0010[32468758] |
| | D88825 *Aeromonas caviae* phaC gene for PHA synthase, complete cds gi\|2335048\|dbj\|D88825.1\|[2335048] |
| | NC_006274 *Bacillus cereus* ZK, complete genome gi\|52140164\|ref\|NC_006274.1\|[52140164] |
| | NC_004557 *Clostridium tetani* E88, complete genome gi\|28209834\|ref\|NC_004557.1\|[28209834] |
| butyryl-CoA dehydrogenase | NC_003030 *Clostridium acetobutylicum* ATCC 824, complete genome gi\|15893298\|ref\|NC_003030.1\|[15893298] |
| | AY741582 *Euglena gracilis* trans-2-enoyl-CoA reductase mRNA, complete cds gi\|58201539\|gb\|AY741582.1\|[58201539] |
| | U37135 *Streptomyces collinus* crotonyl-CoA reductase (ccr) gene, complete cds gi\|1046370\|gb\|U37135.1\|SCU37135[1046370] |
| | AL939127 *Streptomyces coelicolor* A3(2) complete genome; segment 24/29 gi\|24429552\|emb\|AL939127.1\|SCO939127[24429552] |
| | AP006716 *Staphylococcus haemolyticus* JCSC1435, complete genome gi\|68445725\|dbj\|AP006716.1\|[68445725] |
| | NC_006274 *Bacillus cereus* ZK, complete genome gi\|52140164\|ref\|NC_006274.1\|[52140164] |
| | NC_004557 *Clostridium tetani* E88, complete genome gi\|28209834\|ref\|NC_004557.1\|[28209834] |
| butyraldehyde dehydrogenase | AF157306 *Clostridium beijerinckii* strain NRRL B593 hypothetical protein, coenzyme A acylating aldehyde dehydrogenase (ald), acetoacetate:butyrate/acetate coenzyme A transferase (ctfA), acetoacetate:butyrate/acetate coenzyme A transferase (ctfB), and acetoacetate |

TABLE 2-continued

| Sources of 1-Buatnol Pathway Genes | |
|---|---|
| Gene | GenBank Citation |
| | decarboxylase (adc) genes, complete cds<br>gi\|47422980\|gb\|AF157306.2\|[47422980]<br>NC_001988 *Clostridium acetobutylicum* ATCC 824 plasmid pSOL1, complete sequence<br>gi\|15004705\|ref\|NC_001988.2\|[15004705]<br>AY251646 *Clostridium saccharoperbutylacetonicum* sol operon, complete sequence<br>gi\|31075382\|gb\|AY251646.1\|[31075382] |
| butanol dehydrogenase | NC_001988 *Clostridium acetobutylicum* ATCC 824 plasmid pSOL1, complete sequence<br>gi\|15004705\|ref\|NC_001988.2\|[15004705]<br>NC_003030 *Clostridium acetobutylicum* ATCC 824, complete genome<br>gi\|15893298\|ref\|NC_003030.1\|[15893298]<br>NC_000913 *Escherichia coli* K12, complete genome<br>gi\|49175990\|ref\|NC_000913.2\|[49175990]<br>NC_003198 *Salmonella enterica* subsp. *enterica* serovar *Typhi* str. CT18, complete genome<br>gi\|16758993\|ref\|NC_003198.1\|[16758993]<br>BX571966 *Burkholderia pseudomallei* strain K96243, chromosome 2, complete sequence<br>gi\|52211453\|emb\|BX571966.1\|[52211453<br>Z99120 *Bacillus subtilis* complete genome (section 17 of 21): from 3213330 to 3414388<br>gi\|32468813\|emb\|Z99120.2\|BSUB0017[32468813<br>NC_003366 *Clostridium perfringens* str. 13, complete genome<br>gi\|18308982\|ref\|NC_003366.1\|[18308982<br>NC_004431 *Escherichia coli* CFT073, complete genome<br>gi\|26245917\|ref\|NC_004431.1\|[26245917 |

Pathway Steps:

a) Acetyl-CoA to acetoacetyl-CoA, is catalyzed by acetyl-CoA acetyltransferase. The skilled person will appreciate that polypeptides having by acetyl-CoA acetyltransferase activity isolated from a variety of sources will be useful in the present invention independent of sequence homology. Examples of suitable by acetyl-CoA acetyltransferase enzymes are available from a number of sources, for example, for example, *Escherichia coli* (GenBank Nos: NP_416728 (SEQ ID NO:129), NC_000913 (SEQ ID NO:128); NCBI (National Center for Biotechnology Information) amino acid sequence, NCBI nucleotide sequence), *Clostridium acetobutylicum* (GenBank Nos: NP_349476.1 (SEQ ID NO:2), NC_003030 (SEQ ID NO:1); NP_149242 (SEQ ID NO:4), NC_001988 (SEQ ID NO:3), *Bacillus subtilis* (GenBank Nos: NP_390297 (SEQ ID NO:131), NC_000964 (SEQ ID NO:130)), and *Saccharomyces cerevisiae* (GenBank Nos: NP_015297 (SEQ ID NO:133), NC_001148 (SEQ ID NO:132)). Preferred by acetyl-CoA acetyltransferase enzymes are those that have at least 80%-85% identity to SEQ ID NO:2, SEQ ID NO:4, SEQ ID NO:129, SEQ ID NO:131, or SEQ ID NO:133, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

b) Acetoacetyl-CoA to 3-hydroxybutyryl-CoA is catalyzed by 3-hydroxybutyryl-CoA dehydrogenase. The skilled person will appreciate that polypeptides having 3-hydroxybutyryl-CoA dehydrogenase activity isolated from a variety of sources will be useful in the present invention independent of sequence homology. Example of suitable 3-hydroxybutyryl-CoA dehydrogenase enzymes are available from a number of sources, for example, *C. acetobutylicum* (GenBank NOs: NP_349314 (SEQ ID NO:6), NC_003030 (SEQ ID NO:5)), *B. subtilis* (GenBank NOs: AAB09614 (SEQ ID NO:135), U29084 (SEQ ID NO:134)), *Ralstonia eutropha* (GenBank NOs: YP_294481 (SEQ ID NO:137), NC_007347 (SEQ ID NO:136)), and *Alcaligenes eutrophus* (GenBank NOs: AAA21973 (SEQ ID NO:139), J04987 (SEQ ID NO:138)). Preferred 3-hydroxybutyryl-CoA dehydrogenase enzymes are those that have at least 80%-85% identity to SEQ ID NO:6, SEQ ID NO:135, SEQ ID NO:137, or SEQ ID NO:139 where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

c) 3-hydroxybutyryl-CoA to crotonyl-CoA is catalyzed by crotonase. The skilled person will appreciate that polypeptides having crotonase activity isolated from a variety of sources will be useful in the present invention independent of sequence homology. Examples of suitable crotonase enzymes are available from a number of sources, for example, *E. coli* (GenBank NOs: NP_415911 (SEQ ID NO:141), NC_000913 (SEQ ID NO:140)), *C. acetobutylicum* (GenBank NOs: NP_349318 (SEQ ID NO:8), NC_003030 (SEQ ID NO:6)), *B. subtilis* (GenBank NOs: CAB13705 (SEQ ID NO:143), Z99113 (SEQ ID NO:142)), and *Aeromonas caviae* (GenBank NOs: BAA21816 (SEQ ID NO:145), D88825 (SEQ ID NO:144)). Preferred crotonase enzymes are those that have at least 80%-85% identity to SEQ ID NO:8, SEQ ID NO:141, SEQ ID NO:143, and SEQ ID NO:145 where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

d) Crotonyl-CoA to butyryl-CoA, is catalyzed by butyryl-CoA dehydrogenase. The skilled person will appreciate that polypeptides having butyryl-CoA dehydrogenase activity isolated from a variety of sources will be useful in the present invention independent of sequence homology. Examples of suitable butyryl-CoA dehydrogenase enzymes are available from a number of sources, for example, *C. acetobutylicum* (GenBank NOs: NP_347102 (SEQ ID NO:10), NC_003030 (SEQ ID NO:9))), *Euglena gracilis* (GenBank NOs: Q5EU90 SEQ ID NO:147), AY741582 SEQ ID NO:146)), *Streptomyces collinus* (GenBank NOs: AAA92890 (SEQ ID NO:149), U37135 (SEQ ID NO:148)), and *Streptomyces coelicolor* (GenBank NOs: CAA22721 (SEQ ID NO:151), AL939127 (SEQ ID NO:150)). Preferred butyryl-CoA dehydrogenase enzymes are those that have at least 80%-85% identity to SEQ ID NO:10, SEQ ID NO:147, SEQ ID NO:149, SEQ ID NO:151, and SEQ ID NO:187 where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

e) Butyryl-CoA to butyraldehyde, is catalyzed by butyraldehyde dehydrogenase. The skilled person will appreciate that polypeptides having butyraldehyde dehydrogenase activity isolated from a variety of sources will be useful in the present invention independent of sequence homology. Examples of suitable butyraldehyde dehydrogenase enzymes are available from a number of sources, for example, *Clostridium beijerinckii* (GenBank NOs: AAD31841 (SEQ ID NO:12), AF157306 (SEQ ID NO:11)) and *C. acetobutylicum* (GenBank NOs: NP_149325 (SEQ ID NO:153), NC_001988 (SEQ ID NO:152)). Preferred butyraldehyde dehydrogenase enzymes are those that have at least 80%-85% identity to SEQ ID NO:12, SEQ ID NO:153, and SEQ ID NO:189 where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

f) Butyraldehyde to 1-butanol, is catalyzed by butanol dehydrogenase. The skilled person will appreciate that polypeptides having butanol dehydrogenase activity isolated from a variety of sources will be useful in the present invention independent of sequence homology. Some example of suitable butanol dehydrogenase enzymes are available from a number of sources, for example, *C. acetobutylicum* (GenBank NOs: NP_149325 (SEQ ID NO:153), NC_001988 SEQ ID NO:152; note: this enzyme possesses both aldehyde and alcohol dehydrogenase activity); NP_349891 (SEQ ID NO:14), NC_003030 (SEQ ID NO:13); and NP_349892 (SEQ ID NO:16), NC_003030 (SEQ ID NO:15)) and *E. coli* (GenBank NOs: NP_417484 (SEQ ID NO:155), NC_000913 (SEQ ID NO:154)). Preferred butanol dehydrogenase enzymes are those that have at least 80%-85% identity to SEQ ID NO:14, SEQ ID NO:16, SEQ ID NO:153, SEQ ID NO:155, and SEQ ID NO:157 where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

Microbial Hosts for 1-Butanol Production

Microbial hosts for 1-butanol production may be selected from bacteria, cyanobacteria, filamentous fungi and yeasts. The microbial host used for 1-butanol production is preferably tolerant to 1-butanol so that the yield is not limited by butanol toxicity. Microbes that are metabolically active at high titer levels of 1-butanol are not well known in the art. Although 1-butanol-tolerant mutants have been isolated from solventogenic Clostridia, little information is available concerning the 1-butanol tolerance of other potentially useful bacterial strains. Most of the studies on the comparison of alcohol tolerance in bacteria suggest that 1-butanol is more toxic than ethanol (de Cavalho et al., *Microsc. Res. Tech.* 64:215-22 (2004) and Kabelitz et al., *FEMS Microbiol. Lett.* 220:223-227 (2003)). Tomas et al. (*J. Bacteriol.* 186:2006-2018 (2004)) report that the yield of 1-butanol during fermentation in *Clostridium acetobutylicum* may be limited by toxicity. The primary effect of 1-butanol on *Clostridium acetobutylicum* is disruption of membrane functions (Hermann et al., *Appl. Environ. Microbiol.* 50:1238-1243 (1985)).

The microbial hosts selected for the production of 1-butanol are preferably tolerant to 1-butanol and are able to convert carbohydrates to 1-butanol. The criteria for selection of suitable microbial hosts include the following: intrinsic tolerance to 1-butanol, high rate of glucose utilization, availability of genetic tools for gene manipulation, and the ability to generate stable chromosomal alterations.

Suitable host strains with a tolerance for 1-butanol may be identified by screening based on the intrinsic tolerance of the strain. The intrinsic tolerance of microbes to 1-butanol may be measured by determining the concentration of 1-butanol that is responsible for 50% inhibition of the growth rate (IC50) when grown in a minimal medium. The IC50 values may be determined using methods known in the art. For example, the microbes of interest may be grown in the presence of various amounts of 1-butanol and the growth rate monitored by measuring the optical density at 600 nanometers. The doubling time may be calculated from the logarithmic part of the growth curve and used as a measure of the growth rate. The concentration of 1-butanol that produces 50% inhibition of growth may be determined from a graph of the percent inhibition of growth versus the 1-butanol concentration. Preferably, the host strain should have an IC50 for 1-butanol of greater than about 0.5% weight/volume.

The microbial host for 1-butanol production should also utilize glucose at a high rate. Most microbes are capable of utilizing carbohydrates. However, certain environmental microbes cannot utilize carbohydrates to high efficiency, and therefore would not be suitable hosts.

The ability to genetically modify the host is essential for the production of any recombinant microorganism. The mode of gene transfer technology may be by electroporation, conjugation, transduction or natural transformation. A broad range of host conjugative plasmids and drug resistant markers are available. The cloning vectors are tailored to the host organisms based on the nature of antibiotic resistance markers that can function in that host.

The microbial host also has to be manipulated in order to inactivate competing pathways for carbon flow by deleting various genes. This requires the availability of either transposons to direct inactivation or chromosomal integration vectors. Additionally, the production host should be amenable to chemical mutagenesis so that mutations to improve intrinsic 1-butanol tolerance may be obtained.

Based on the criteria described above, suitable microbial hosts for the production of 1-butanol include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* and *Saccharomyces cerevisiae*.

Construction of Production Host

Recombinant organisms containing the necessary genes that will encode the enzymatic pathway for the conversion of a fermentable carbon substrate to 1-butanol may be constructed using techniques well known in the art. Genes encoding the enzymes of the 1-butanol biosynthetic pathway, i.e., acetyl-CoA acetyltransferase, 3-hydroxybutyryl-CoA dehydrogenase, crotonase, butyryl-CoA dehydrogenase, butyraldehyde dehydrogenase, and butanol dehydrogenase, may be isolated from various sources, as described above.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer-directed amplification methods such as polymerase chain reaction (Mullis, U.S. Pat. No. 4,683,202) to obtain amounts of DNA suitable for transformation using appropriate vectors. Tools for codon optimization for expression in a heterologous host are readily available. Some tools for codon optimization are available based on the GC content of the host organism. The GC content of some exemplary microbial hosts is given Table 3.

TABLE 3

GC Content of Microbial Hosts

| Strain | % GC |
|---|---|
| *B. licheniformis* | 46 |
| *B. subtilis* | 42 |
| *C. acetobutylicum* | 37 |
| *E. coli* | 50 |
| *P. putida* | 61 |
| *A. eutrophus* | 61 |
| *Paenibacillus macerans* | 51 |
| *Rhodococcus erythropolis* | 62 |
| *Brevibacillus* | 50 |
| *Paenibacillus polymyxa* | 50 |

Once the relevant pathway genes are identified and isolated they may be transformed into suitable expression hosts by means well known in the art. Vectors or cassettes useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); and lac, ara, tet, trp, $IP_L$, $IP_R$, T7, tac, and trc (useful for expression in *Escherichia coli, Alcaligenes*, and *Pseudomonas*); the amy, apr, npr promoters and various phage promoters useful for expression in *Bacillus subtilis, Bacillus licheniformis*, and *Paenibacillus macerans*; nisA (useful for expression Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)).

Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to create gene replacement in a range of Gram-positive bacteria (Maguin et al., *J. Bacteriol.* 174(17):5633-5638 (1992)). Additionally, in vitro transposomes are available to create random mutations in a variety of genomes from commercial sources such as EPICENTRE®.

The expression of the 1-butanol biosynthetic pathway in various preferred microbial hosts is described in more detail below.

Expression of the 1-Butanol Biosynthetic Pathway in *E. Coli*

Vectors or cassettes useful for the transformation of *E. coli* are common and commercially available from the companies listed above. For example, the genes of the 1-butanol biosynthetic pathway may be isolated from various strains of *Clostridium*, cloned into a modified pUC19 vector and transformed into *E. coli* NM522, as described in Example 15. The expression of the 1-butanol biosynthetic pathway in several other strains of *E. coli* is described in Example 17.

Expression of the 1-Butanol Biosynthetic Pathway in *Rhodococcus erythropolis*

A series of *E. coli-Rhodococcus* shuttle vectors are available for expression in *R. erythropolis*, including, but not limited to pRhBR17 and pDA71 (Kostichka et al., *Appl. Microbiol. Biotechnol* 62:61-68 (2003)). Additionally, a series of promoters are available for heterologous gene expression in *R. erythropolis* (see for example Nakashima et al., *Appl. Envir. Microbiol.* 70:5557-5568 (2004), and Tao et al., *Appl. Microbiol. Biotechnol.* 2005, DOI 10.1007/s00253-005-0064). Targeted gene disruption of chromosomal genes in *R. erythropolis* may be created using the method described by Tao et al., supra, and Brans et al. (*Appl. Envir. Microbiol.* 66: 2029-2036 (2000)).

The heterologous genes required for the production of 1-butanol, as described above, may be cloned initially in pDA71 or pRhBR71 and transformed into *E. coli*. The vectors may then be transformed into *R. erythropolis* by electroporation, as described by Kostichka et al., supra. The recombinants may be grown in synthetic medium containing glucose and the production of 1-butanol can be followed using methods known in the art.

Expression of the 1-Butanol Biosynthetic Pathway in *Bacillus subtilis*

Methods for gene expression and creation of mutations in *B. Subtilis* are also well known in the art. For example, the genes of the 1-butanol biosynthetic pathway may be isolated from various strains of *Clostridium*, cloned into a modified pUC19 vector and transformed into *Bacillus subtilis* BE1010, as described in Example 16. Additionally, the six genes of the 1-biosynthetic pathway can be split into two operons for expression, as described in Example 18. The first three genes of the pathway (thl, hbd, and crt) were integrated into the chromosome of *Bacillus subtilis* BE1010 (Payne and Jackson, *J. Bacteriol.* 173:2278-2282 (1991)). The last three genes (EgTER, ald, and bdhB) were cloned into expression plasmids and transformed into the *Bacillus* strain carrying the integrated 1-butanol genes Expression of the 1-Butanol Biosynthetic Pathway in *Bacillus licheniformis*

Most of the plasmids and shuttle vectors that replicate in *B. subtilis* may be used to transform *B. licheniformis* by either protoplast transformation or electroporation. For example, the genes required for the production of 1-butanol may be cloned in plasmids pBE20 or pBE60 derivatives (Nagarajan et al., *Gene* 114:121-126 (1992)). Methods to transform *B. licheniformis* are known in the art (for example see Fleming et al. *Appl. Environ. Microbiol.,* 61(11):3775-3780 (1995)). The plasmids constructed for expression in *B. subtilis* may also be transformed into *B. licheniformis* to produce a recombinant microbial host that produces 1-butanol.

Expression of the 1-Butanol Biosynthetic Pathway in *Paenibacillus macerans*

Plasmids may be constructed as described above for expression in *B. subtilis* and used to transform *Paenibacillus macerans* by protoplast transformation to produce a recombinant microbial host that produces 1-butanol.

Expression of the 1-Butanol Biosynthetic Pathway in *Alcaligenes* (*Ralstonia*) *eutrophus*

Methods for gene expression and creation of mutations in *Ralstonia eutrophus* are known in the art (see for example Taghavi et al., *Appl. Environ. Microbiol.,* 60(10):3585-3591 (1994)). The genes for the 1-butanol biosynthetic pathway may be cloned in any of the broad host range vectors described above, and electroporated to generate recombinants that produce 1-butanol. The polyhydroxy butyrate pathway in *Ralstonia* has been described in detail and a variety of genetic techniques to modify the *Ralstonia eutrophus* genome is known, and those tools can be applied for engineering the 1-butanol biosynthetic pathway.

Expression of the 1-Butanol Biosynthetic Pathway in *Pseudomonas putida*

Methods for gene expression in *Pseudomonas putida* are known in the art (see for example Ben-Bassat et al., U.S. Pat. No. 6,586,229, which is incorporated herein by reference). For example, the 1-butanol pathway genes may be inserted into PPCU18 and this ligated DNA may be electroporated into electrocompetent *Pseudomonas putida* DOT-T1 C5aAR1 cells to generate recombinants that produce 1-butanol.

Expression of the 1-Butanol Biosynthetic Pathway in *Saccharomyces cerevisiae*

Methods for gene expression in *Saccharomyces cerevisiae* are known in the art (see for example *Methods in Enzymology*, Volume 194*, Guide to Yeast Genetics and Molecular and Cell Biology* (Part A, 2004, Christine Guthrie and Gerald R. Fink (Eds.), Elsevier Academic Press, San Diego, Calif.). Expression of genes in yeast typically requires a promoter, followed by the gene of interest, and a transcriptional terminator. A number of yeast promoters can be used in constructing expression cassettes for genes encoding the 1-butanol biosynthetic pathway, including, but not limited to constitutive promoters FBA, GPD, and GPM, and the inducible promoters GAL1, GAL10, and CUP1. Suitable transcriptional terminators include, but are not limited to FBAt, GPDt, GPMt, ERG10t, and GAL1t. Suitable promoters, transcriptional terminators, and the genes of the 1-butanol biosynthetic pathway may be cloned into yeast 2 micron (2μ) plasmids, as described in Example 21.

Expression of the 1-Butanol Biosynthetic Pathway in *Lactobacillus plantarum*

The *Lactobacillus* genus belongs to the Lactobacillales family and many plasmids and vectors used in the transformation of *Bacillus subtilis* and *Streptococcus* may be used for *lactobacillus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (e.g., van Kranenburg R, Golic N, Bongers R, Leer R J, de Vos W M, Siezen R J, Kleerebezem M. *Appl. Environ. Microbiol.* 2005 March; 71(3): 1223-1230). For example, expression of the 1-butanol biosynthetic pathway in *Lactobacillus plantarum* is described in Example 22.

Expression of the 1-Butanol Biosynthetic Pathway in *Enterococcus faecium, Enterococcus gallinarium*, and *Enterococcus faecalis*

The *Enterococcus* genus belongs to the Lactobacillales family and many plasmids and vectors used in the transformation of *Lactobacillus, Bacillus subtilis*, and *Streptococcus* may be used for *Enterococcus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Expression vectors for *E. faecalis* using the nisA gene from *Lactococcus* may also be used (Eichenbaum et al., *Appl. Environ. Microbiol.* 64:2763-2769 (1998). Additionally, vectors for gene replacement in the *E. faecium* chromosome may be used (Nallaapareddy et al., *Appl. Environ. Microbiol.* 72:334-345 (2006)). For example, expression of the 1-butanol biosynthetic pathway in *Enterococcus faecalis* is described in Example 23.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C*1 Compd., [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in co-owned and co-pending U.S. Patent Application Publication No. 2007/0031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of the enzymatic pathway necessary for 1-butanol production.

Culture Conditions with Temperature Lowering

In the present method, the recombinant microbial production host which produces 1-butanol is seeded into a fermentation medium comprising a fermentable carbon substrate to create a fermentation culture. The production host is grown in the fermentation culture at a first temperature for a first period of time. The first temperature is typically from about 25° C. to about 40° C.

Suitable fermentation media in the present invention include common commercially prepared media such as Luria Bertani (LB) broth, Sabouraud Dextrose (SD) broth or Yeast Medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

The first period of time to grow the production host at the first temperature may be determined in a variety of ways. For example, during this period of growth a metabolic parameter of the fermentation culture may be monitored. The metabolic parameter that is monitored may be any parameter known in the art, including, but not limited to the optical density, pH, respiratory quotient, fermentable carbon substrate utilization, $CO_2$ production, and 1-butanol production. During this period of growth, additional fermentable carbon substrate may be added, the pH may be adjusted, oxygen may be added for aerobic cells, or other culture parameters may be adjusted to support the metabolic activity of the culture. Though nutrients and culture conditions are supportive of growth, after a period of time the metabolic activity of the fermentation culture decreases as determined by the monitored parameter described above. For example, a decrease in metabolic activity may be indicated by a decrease in one or more of the following parameters: rate of optical density change, rate of pH change, rate of change in respiratory quotient (if the host cells are aerobic), rate of fermentable carbon substrate utilization, rate of 1-butanol production, rate of change in $CO_2$ production, or rate of another metabolic parameter. The decrease in metabolic activity is related to the sensitivity of the host cells to the production of 1-butanol and/or the presence of 1-butanol in the culture. When decreased metabolic activity is detected, the temperature of the fermentation culture is lowered to reduce the sensitivity of the host cells to 1-butanol and thereby allow further production of 1-butanol. In one embodiment, the lowering of the temperature coincides with a change in the metabolic parameter that is monitored.

In one embodiment, the change in metabolic activity is a decrease in the rate of 1-butanol production. 1-Butanol production may be monitored by analyzing the amount of 1-butanol present in the fermentation culture medium as a function of time using methods well known in the art, such as using high performance liquid chromatography (HPLC) or gas chromatography (GC), which are described in the Examples herein. GC is preferred due to the short assay time.

Alternatively, the lowering of the temperature of the fermentation culture may occur at a predetermined time. The first period of time may be predetermined by establishing a correlation between a metabolic parameter of the fermentation culture and time in a series of test fermentations runs. A correlation between a metabolic parameter, as described above, and time of culture growth may be established for any 1-butanol producing host by one skilled in the art. The specific correlation may vary depending on conditions used including, but not limited to, carbon substrate, fermentation conditions, and the specific recombinant 1-butanol producing microbial production host. The correlation is most suitably made between 1-butanol production or specific glucose consumption rate and time of culture growth. Once the predetermined time has been established from the correlation, the temperature of the fermentation culture in subsequent fermentation runs is lowered at the predetermined time. For example, if it is determined by monitoring a metabolic parameter in the test fermentation runs that the rate of production of 1-butanol decreases after 12 hours, the temperature in subsequent fermentations runs is lowered after 12 hours without the need to monitor 1-butanol production in the subsequent runs.

After the first period of time, the temperature of the fermentation culture is lowered to a second temperature. Typically, the second temperature is about 3° C. to about 25° C. lower than the first temperature. Reduction in temperature to enhance tolerance of the host cells to 1-butanol is balanced with maintaining the temperature at a level where the cells continue to be metabolically active for 1-butanol production. For example, a fermentation culture that has been grown at about 35° C. may be reduced in temperature to about 28° C.; or a culture grown at about 30° C. may be reduced in temperature to about 25° C. The change in temperature may be done gradually over time or may be made as a step change. The production host is incubated at the second temperature for a second period of time, so that 1-butanol production continues. The second period of time may be determined in the same manner as the first period of time described above, e.g., by monitoring a metabolic parameter or by using a predetermined time.

Additionally, the temperature lowering and incubation steps may be repeated one or more times to more finely balance metabolic activity for 1-butanol production and 1-butanol sensitivity. For example, a culture that has been grown at about 35° C. may be reduced in temperature to about 32° C., followed by an incubation period. During this period a metabolic parameter of the fermentation culture may be monitored as described above, or a predetermined time may be used. It is particularly suitable to monitor the production of 1-butanol during this incubation period. When monitoring indicates a decrease in metabolic activity or at a predetermined time, the temperature may be reduced a second time. For example, the temperature may be reduced from about 32° C. to about 28° C. The temperature lowering and incubation steps may be repeated a third time where the temperature is reduced, for example, to about 20° C. The production host is incubated at the lowered temperature so that 1-butanol production continues. The steps may be repeated further as necessary to obtain the desired 1-butanol titer.

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1-butanol production.

Methods for 1-Butanol Isolation from the Fermentation Medium

The bioproduced 1-butanol may be isolated from the fermentation medium using methods known in the art. For example, solids may be removed from the fermentation medium by centrifugation, filtration, decantation, or the like. Then, the 1-butanol may be isolated from the fermentation medium, which has been treated to remove solids as described above, using methods such as distillation, liquid-liquid extraction, or membrane-based separation. Because 1-butanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify 1-butanol include, but are not limited to, decantation, liquid-liquid extraction, adsorption, and membrane-based techniques. Additionally, 1-butanol may be isolated using azeotropic distillation using an entrainer (see for example Doherty and Malone, *Conceptual Design of Distillation Systems*, McGraw Hill, N.Y., 2001).

The 1-butanol-water mixture forms a heterogeneous azeotrope so that distillation may be used in combination with decantation to isolate and purify the 1-butanol. In this method, the 1-butanol containing fermentation broth is distilled to near the azeotropic composition. Then, the azeotropic mixture is condensed, and the 1-butanol is separated from the fermentation medium by decantation. The decanted aqueous phase may be returned to the first distillation column as reflux. The 1-butanol-rich decanted organic phase may be further purified by distillation in a second distillation column.

The 1-butanol may also be isolated from the fermentation medium using liquid-liquid extraction in combination with distillation. In this method, the 1-butanol is extracted from the fermentation broth using liquid-liquid extraction with a suitable solvent. The 1-butanol-containing organic phase is then distilled to separate the 1-butanol from the solvent.

Distillation in combination with adsorption may also be used to isolate 1-butanol from the fermentation medium. In this method, the fermentation broth containing the 1-butanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the 1-butanol from the fermentation medium. In this method, the fermentation broth containing the 1-butanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified. Microbial samples were obtained from The American Type Culture Collection (ATCC; Manassas, Va.) unless otherwise noted.

The oligonucleotide primers used for cloning in the following Examples are given in Table 4. The primers used to sequence or screen the cloned genes are given in Table 5. All the oligonucleotide primers were synthesized by Sigma-Genosys (Woodlands, Tex.).

TABLE 4

Oligonucleotide Cloning Primers

| Gene | Primer Name | Sequence | SEQ ID NO: | Description |
|---|---|---|---|---|
| crt | N3 | CACCATGGAACTAAACAAT GTCATCCTTG | 17 | crt forward |
| crt | N4 | CCTCCTATCTATTTTTGAA GCCTTC | 18 | crt reverse |
| hbd | N5 | CACCATGAAAAAGGTATGT GTTATAGGT | 19 | hbd forward |
| hbd | N6 | CATTTGATAATGGGGATTC TTGT | 20 | hbd reverse |
| thlA | N7 | CACCATGAAAGAAGTTGTA ATAGCTAGTGC | 21 | thlA forward |
| thlA | N8 | CTAGCACTTTTCTAGCAAT ATTGCTG | 22 | thlA reverse |
| bdhA | N9 | CACCATGCTAAGTTTTGAT TATTCAATAC | 23 | bdhA forward |
| bdhA | N10 | TTAATAAGATTTTTTAAATA TCTCA | 24 | bdhA reverse |
| bdhB | N11 | CACCATGGTTGATTTCGAA TATTCAATACC | 25 | bdhB forward |
| bdhB | N12 | TTACACAGATTTTTTGAATA TTTGT | 26 | bdhB reverse |
| thlB | N15 | CACCATGAGAGATGTAGTA ATAGTAAGTGCTG | 27 | thlB forward |
| thlB | N16 | CCGCAATTGTATCCATATT GAACC | 28 | thlB reverse |
| CAC0462 | N17 | CACCATGATAGTAAAAGCA AAGTTTG | 29 | CAC0462 forward |
| CAC0462 | N21 | GCTTAAAGCTTAAAACCGC TTCTGGCG | 30 | CAC0462 reverse |
| ald | N27F1 | CACCATGAATAAAGACACA CTAATACC | 31 | ald forward |
| ald | N28R1 | GCCAGACCATCTTTGAAAA TGCGC | 32 | ald reverse |
| thlA | N44 | CATGCATGCAAAGGAGGTT AGTAGAATGAAAGAAG | 33 | thlA forward |
| thlA | N45 | GTCCTGCAGGGCGCGCCC AATACTTTCTAGCACTTTTC | 34 | thlA reverse |
| hbd | N42 | CATGTCGACAAAGGAGGT CTGTTTAATGAAAAAGGTA TG | 35 | hbd forward |
| hbd | N43 | GTCGCATGCCTTGTAAACT TATTTTGAA | 36 | hbd reverse |
| CAC0462 | N68 | CATAGATCTGGATCCAAAG GAGGGTGAGGAAATGATA GTAAAAG | 37 | CAC0462 forward |
| CAC0462 | N69 | CATGTCGACGTGCAGCCTT TTTAAGGTTCT | 38 | CAC0462 reverse |
| crt | N38 | CATGAATTCACGCGTAAAG GAGGTATTAGTCATGGAAC | 39 | crt forward |
| crt | N39 | GTCGGATCCCTTACCTCCT ATCTATTTTTG | 40 | crt reverse |

TABLE 4-continued

Oligonucleotide Cloning Primers

| Gene | Primer Name | Sequence | SEQ ID NO: | Description |
|---|---|---|---|---|
| ald | N58 | CATGCCCGGGGGTCACCAAAGGAGGAATAGTTCATGAATAAA | 41 | ald forward |
| ald | N59 | CATGGTTAACAAGAAGTTAGCCGGCAAGTACA | 42 | ald reverse |
| bdhB | N64 | CATGGTTAACAAAGGAGGGGTTAAAATGGTTGATTTCGAAT | 43 | bdhB forward |
| bdhB | N65 | CATGGCATGCGTTTAAACGTAGGTTTACACAGATTTT | 44 | bdhB reverse |
| — | BenF | ACTTTCTTTCGCCTGTTTCAC | 73 | — |
| — | BenMA R | CATGAAGCTTGGCGCGCCGGGACGCGTTTTTGAAAATAATGAAAACT | 74 | — |
| — | BenBPR | CATGAAGCTTGTTTAAACTCGGTGACCTTGAAAATAATGAAAACTTATATTGTTTTGAAAATAATGAAAACTTATATTG | 75 | — |
| EgTER (opt) | N85 | CATAGATCTGGATCCAAAGGAGGGTGAGGAAATGGCGATGTTTACG | 80 | Egter forward |
| EgTER (opt) | N86 | GTCGACTTACTGCTGGGCGG | 81 | Egter reverse |
| Ptrc-ald(opt) | T-Ptrc (BspEl) | TTCCGTACTTCCGGACGACTGCACGGTGCACCAATGCTTCTG | 87 | Ptrc forward |
| Ptrc-ald(opt) | B-aldopt (Scal) | CGGATCTTAAGTACTTTAAC CCGCCAGCACACAGCGGCGCTGG | 88 | ald reverse |
| ald | AF BamHI | CATTGGATCCATGAATAAAGACACACTAATACCTACAAC | 93 | ald forward |
| ald | AR Aat2 | CATGACGTCACTAGTGTTAACAAGAAGTTAGCCGGCAAG | 94 | ald reverse |
| EgTER | Forward 1 (E) | CATGTTAACAAAGGAGGAAAGATCTATGGCGATGTTTACGACCACCGCAA | 95 | EgTER SOE forward |
| EgTER | Bottom Reverse 1 (E) | CCCCTCCTTTGGCGCGCCTTACTGCTGGGCGGCGCTCGGCAGA | 96 | EgTER SOE reverse |
| bdh | Top Forward 2 (B) | GCCCAGCAGTAAGGCGCGCCAAAGGAGGGGTTAAAATGGTTGATTTCGAAT | 97 | bdh SOE forward |
| bdh | Reverse 2 (B) | GTCGACGTCATACTAGTTTACACAGATTTTTTGAATATTTGT | 98 | bdh SOE reverse |
| — | Pamy/lacO F | CATTGTACAGAATTCGAGCTCTCGAGGCCCCGCACATACGAAAAGAC | 99 | Pamy forward |
| — | Pamy/lacO R | CATTGTACAGTTTAAACATAGGTCACCCTCATTTTCGTAGGAATTGTTATCC | 100 | Pamy reverse |
| — | Spac F | CATCTCGAGTAATTCTACACAGCCCAGTCC | 101 | Pspac forward |
| — | Spac R | CATGTTTAAACGGTGACCCAAGCTGGGGATCCGCGG | 102 | Pspac reverse |
| thl | Top TF | CATTGGTCACCATTCCCGGGCATGCAAAGGAGGTTAGTAGAATG | 103 | thl SOE Forward |
| thl | Bot TR | CCTTTACGCGACCGGTACTAGTCAAGTCGACAGGGCGCGCCCAATACTTTC | 104 | thl SOE reverse |
| crt | Top CF | CGCGCCCTGTCGACTTGACTAGTACCGGTCGCGTAAAGGAGGTATTAGTCATGGAAC | 105 | crt SOE forward |
| crt | Bot CR | CATCGTTTAAACTTGGATCCAGATCCCTTACCTCCTAT | 106 | crt SOE reverse |
| ERG10-ERG10t | OT731 | AAAGCTGGAGCTCCACCGCGGTGGCGGCCGCTCTAGAAGTTTTCAAAGCAGAGTTTCGTTTGAATATTTTACCA | 164 | ERG10-ERG10t forward |
| ERG10-ERG10t | OT732 | TTCAATATGCATGCCTCAGAACGTTTACATTGTATCGACTGCCAGAACCC | 165 | ERG10-ERG10t reverse |
| GAL1-GAL10 | OT733 | GCAGTCGATACAATGTAAACGTTCTGAGGCATGCATATTGAATTTTCAAAAATTCTTACTTTTTTTTTGGATGGACGCA | 166 | GAL1-GAL10 forward |
| GAL1-GAL10 | OT734 | ACCTGCACCTATAACACATACCTTTTCCATGGTAGTTTTTTCTCCTTGACGTTAAAGTATAGAGGTATATTA | 167 | GAL1-GAL10 reverse |
| hbd | OT735 | AAAAACTACCATGGAAAAGGTATGTGTTATAGGTGCAGGTACTATGGGTTCAGGAATTGC | 168 | hbd forward |
| hbd | OT736 | GTAAAAAAAAGAAGGCCGTATAGGCCTTATTTTGAATAATCGTAGAAACCTTTTCCTGATTTTCTTCCAAG | 169 | hbd reverse |
| GAL1t | OT737 | ACGATTATTCAAAATAAGGCCTATACGGCCTTCTTTTTTTTACTTTGTTCAGAACAACTTCTCATTTTTTTCTACTCATAA | 170 | GAL1t forward |
| GAL1t | OT738 | GAATTGGGTACCGGGCCCCCCCTCGAGGTCGACCGATGCCTCATAAACTTCGGTAGTTATATTACTCTGAGAT | 171 | GAL1t reverse |
| thlA | OT797 | AAAGTAAGAATTTTTGAAAATTCAATATGCATGCAAGAAGTTGTAATAGCTAGTGCAGTAAGAAC | 172 | thlA forward |
| thlA | OT798 | GAAAAAGATCATGAGAAAATCGCAGAACGTAAGGCGCGCCTCAGCACTTTTCTAGCAATATTGCTGTTCCTTG | 173 | thlA reverse |

TABLE 4-continued

Oligonucleotide Cloning Primers

| Gene | Primer Name | Sequence | SEQ ID NO: | Description |
|---|---|---|---|---|
| CUP1 | OT806 | CTCGAAAATAGGGCGCGCCCCCATTACCGACATTTGGGCGC | 174 | CUP1 forward |
| CUP1 | OT807 | ACTGCACTAGCTATTACAACTTCTTGCATGCGTGATGATTGATTGATTGATTGTA | 175 | CUP1 reverse |
| GPD promoter | OT808 | TCGGTAATGGGGGCGCGCCCTATTTTCGAGGACCTTGTCACCTTGA | 176 | GPD promoter forward |
| GPD promoter | OT809 | TTTCGAATAAACACACATAAACAAACACCCCATGGAAAAGGTATGTGTTATAGGTGCAGG | 177 | GPD promoter reverse |
| FBA1 promoter | OT799 | TACCGGGCCCCCCCTCGAGGTCGACGGCGCGCCACTGGTAGAGAGCGACTTTGTATGCCCCA | 178 | FBA1 promoter forward |
| FBA1 promoter | OT761 | CTTGGCCTTCACTAGCATGCTGAATATGTATTACTTGGTTATGGTTATATATGACAAAAG | 179 | FBA1 promoter reverse |
| GPM1 promoter | OT803 | CCCTCACTAAAGGGAACAAAAGCTGGAGCTCGATATCGGCGCGCCCACATGCAGTGATGCACGCGCGA | 180 | GPM1 promoter forward |
| GPM1 promoter | OT804 | AAGGATGACATTGTTTAGTTCCATGGTTGTAATATGTGTGTTTGTTTGG | 181 | GPM1 promoter reverse |
| crt | OT785 | CACACATATTACAACCATGGAACTAAACAATGTCATCCTTGAAAAGGAAGG | 182 | Crt forward |
| crt | OT786 | ATCATTCATTGGCCATTCAGGCCTTATCTATTTTTGAAGCCTTCAATTTTTCTTTTCTCTATG | 183 | Crt reverse |
| GPM1t terminator | OT787 | CAAAAATAGATAAGGCCTGAATGGCCAATGAATGATTTGATGATTTCTTTTTCCCTCCATTTTTC | 184 | GPM1t terminator forward |
| GPM1t terminator | OT805 | GAATTGGGTACCGGGCCCCCCCTCGAGGTCGACTTATAGTATTATATTTTCTGATTTGGTTATAGCAAGCAGCGTTT | 185 | GPM1t terminator reverse |
| GPD promoter | OT800 | GGGAACAAAAGCTGGAGCTCCACCGCGGTGGGGCGCGCCCTATTTTCGAGGACCTTGTCACCTTGAGCC | 190 | GPD promoter forward |
| GPD promoter | OT758 | TTAAGGTATCTTTATCCATGGTGTTTGTTTATGTGTGTTTATTCGAAACT | 191 | GPD promoter reverse |
| GPD terminator | OT754 | TTGGGTACCGGGCCCCCCCTCGAGGTCGACTGGCCATTAATCTTTCCCATAT | 192 | GPD terminator forward |
| GPD terminator | OT755 | TGTGTCCTAGCAGGTTAGGGCCTGCAGGGCCGTGAATTTACTTTAAATCTTG | 193 | GPD terminator reverse |
| FBA1 promoter | OT760 | CGAAAATAGGGCGCGCCACTGGTAGAGAGCGACTTTGTATGCCCCAATTG | 194 | FBA1 promoter forward |
| FBA1 promoter | OT792 | CCCTTGACGAACTTGGCCTTCACTAGCATGCTGAATATGTATTACTTGGTTATGGTTATATATGACAAAAG | 195 | FBA1 promoter reverse |
| FBA1 terminator | OT791 | CCCTTGACGAACTTGGCCTTCACTAGCATGCTGAATATGTATTACTTGGTTATGGTTATATATGACAAAAG | 196 | FBA1 terminator forward |
| FBA1 terminator | OT765 | GGAACAAAAGCTGGAGCTCCACCGCGGTGGTTTAACGTATAGACTTCTAATATATTTCTCCATACTTGGTATT | 197 | FBA1 terminator reverse |
| ldhL | LDH EcoRV F | GACGTCATGACCACCCGCCGATCCCTTTT | 198 | ldhL forward |
| ldhL | LDH AatIIR | GATATCCAACACCAGCGACCGACGTATTAC | 199 | ldhL reverse |
| Cm | Cm F | ATTTAAATCTCGAGTAGAGGATCCCAACAAACGAAAATTGGATAAAG | 200 | Cm forward |
| Cm | Cm R | ACGCGTTATTATAAAAGCCAGTCATTAGG | 201 | Cm reverse |
| P11 | P11 F | TCGAGAGCGCTATAGTTGTTGACAGAATGGACATACTATGATATATTGTTGCTATAGCGCCC | 202 | P11 promoter forward |
| P11 | P11 R | GGGCGCTATAGCAACAATATATCATAGTATGTCCATTCTGTCAACAACTATAGCGCTC | 203 | P11 promoter reverse |
| PldhL | PldhL F | GAGCTCGTCGACAAACCAACATTATGACGTGTCTGGGC | 204 | ldhL promoter forward |
| PldhL | PldhL R | GGATCCTACCATGTTTGTGCAAAATAAGTG | 205 | ldhL promoter reverse |
| PnisA | F-PnisA (EcoRV) | TTCAGTGATATCGACATACTTGAATGACCTAGTC | 206 | PnisA forward |
| PnisA | R-PnisA(Pmel BamHI) | TTGATTAGTTTAAACTGTAGGATCCTTTGAGTGCCTCCTTATAATTTA | 207 | PnisA reverse |

TABLE 5

Sequencing and PCR Screening Primers

| Name | Sequence | Gene-specific | SEQ ID NO: |
|---|---|---|---|
| M13 Forward | GTAAAACGACGGCCAGT | TOPO vector | 45 |

TABLE 5-continued

Sequencing and PCR Screening Primers

| Name | Sequence | Gene-specific | SEQ ID NO: |
|---|---|---|---|
| M13 Reverse | AACAGCTATGACCATG | TOPO vector | 46 |
| N7SeqF1 | GCAGGAGATGCTGACGTAATAA | thlA | 47 |
| N7SeqR1 | CCAACCTGCTTTTTCAATAGCTGC | thlA | 48 |
| N15SeqF1 | CAGAGATGGGGTCAAAGAATG | thlB | 49 |
| N16SeqR1 | GTGGTTTTATTCCGAGAGCG | thlB | 50 |
| N5SeqF2 | GGTCTATACTTAGAATCTCC | hbd | 51 |
| N6SeqR2 | CGGAACAGTTGACCTTAATATGGC | hbd | 52 |
| N22SeqF1 | GCCTCATCTGGGTTTGGTCTTG | CAC0426 | 53 |
| N22SeqF2 | CGCCTAGGAGAAAGGACTATAAAA CTGG | CAC0426 | 54 |
| N22SeqF3 | CAGAGTTATAGGTGGTAGAGCC | CAC0426 | 55 |
| N23SeqR1 | CCATCCCGCTGTTCCTATTCTTCT | CAC0426 | 56 |
| N23SeqR2 | CCAATCCTCTCCACCCATTACC | CAC0426 | 57 |
| N23SeqR3 | CGTCCATCCTTAATCTTCCC | CAC0426 | 58 |
| N31SeqF2 | CCAACTATGGAATCCCTAGATGC | ald | 59 |
| N31SeqF3 | GCATAGTCTGCGAAGTAAATGC | ald | 60 |
| N31SeqF4 | GGATCTACTGGTGAAGGCATAACC | ald | 61 |
| N32SeqR1 | GTTAGCCGGCAAGTACACATC | ald | 72 |
| N32SeqR2 | GGCATCATGAGTTCTGTCATGAC | ald | 62 |
| N32SeqR3 | GCCTTCAATGATACTCTTACCAGCC | ald | 63 |
| N32SeqR4 | GCATTTCCAGCAGCTATCATGC | ald | 64 |
| N32SeqR5 | CCTTCCCATATGTGTTTCTTCC | ald | 65 |
| N11SeqF1 | GTTGAAGTAGTACTAGCTATAG | bdhB | 66 |
| N11SeqF2 | GACATAACACACGGCGTAGGGC | bdhB | 67 |
| N12SeqR1 | TAAGTGTACACTCCAATTAGTG | bdhB | 68 |
| N12SeqR2 | GCCATCTAACACAATATCCCATGG | bdhB | 69 |
| N9SeqF1 | GCGATACATGGGACATGGTTAAAG | bdhA | 70 |
| N10SeqR1 | TGCACTTAACTCGTGTTCCATA | bdhA | 71 |
| T7Primer | TAATACGACTCACTATAGGG | pET23 vector | 82 |
| Trc99aF | TTGACAATTAATCATCCGGC | p Trc99a vector | 83 |
| N5SeqF4 | GGTCAACTGTTCCGGAAATTC | hbd | 84 |
| T-ald(BamHI) | TGATCTGGATCCAAGAAGGAGCCC TTCACCATGAATAAAGACACAC | ald | 85 |
| B-ald(EgTER) | CATCGCCATTTCCTCACCCTCCTTT TTAGCCGGCAAGTACACATCTTCTT TGTC | ald | 86 |
| N3SeqF1 | CCATCATACCATACTGACCC | crt | 107 |
| N3SeqF2 | GCTACTGGAGCATTGCTCAC | crt | 108 |
| N3SeqF3 | CCATTAACAGCTGCTATTACAGGC | crt | 109 |
| N4SeqR3 | GGTCTCGGAATAACACCTGG | crt | 110 |
| N5SeqF3 | CAAGCTTCATAACAGGAGCTGG | hbd | 111 |
| N7SeqR2 | ATCCCACAATCCGTCAGTGATC | thlA | 112 |
| N31SeqF1 | CTGAGATAAGAAAGGCCGCA | ald | 113 |
| N62SeqF2 | CAACCCTGGGCGTGTTTCTG | EgTER | 114 |
| N62SeqF3 | GTGGCGAAGATTGGGAACTG | EgTER | 115 |
| N62SeqF4 | GGGAAATGGCAGAAGATGTTCAGC | EgTER | 116 |
| N63SeqR1 | CGGTCTGATAACCTGCAAAATCGC | EgTER | 117 |
| N63SeqR2 | CACCAGCGCTTTGGCAACAAC | EgTER | 118 |
| N63SeqR3 | GAACGTGCATACAGACCTGCTTC | EgTER | 119 |
| N63SeqR4 | CGGCTGAATAACTTTTGCGG | EgTER | 120 |
| Pamy SeqF2 | GCCTTTGATGACTGATGATTTGGC | pFP988 vector | 121 |
| Pamy SeqF | TCTCCGGTAAACATTACGGCAAAC | pFP988 vector | 122 |
| Pamy SeqR | CGGTCAGATGCAATTCGACATGTG | pFP988 vector | 123 |
| SpacF Seq | GAAGTGGTCAAGACCTCACT | Pspac promoter | 124 |
| sacB Up | CGGGTTTGTTACTGATAAAGCAGG | sacB | 125 |
| sacB Dn | CGGTTAGCCATTTGCCTGCTTTTA | sacB | 126 |
| HT R | ACAAAGATCTCCATGGACGCGT | pHT01 vector | 127 |
| Scr1 | CCTTTCTTTGTGAATCGG | csc | 160 |
| Scr2 | AGAAACAGGGTGTGATCC | csc | 161 |
| Scr3 | AGTGATCATCACCTGTTGCC | csc | 162 |
| Scr4 | AGCACGGCGAGAGTCGACGG | csc | 163 |

Methods for Determining 1-Butanol Concentration in Culture Media

The concentration of 1-butanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. 1-Butanol had a retention time of 52.8 min under the conditions used. Alternatively, gas chromatography (GC) methods are available. For example, a specific GC method utilized an HP-INNOWax column (30 m×0.53 mm id, 1 μm film thickness, Agilent Technologies, Wilmington, Del.), with a flame ionization detector (FID). The carrier gas was helium at a flow rate of 4.5 mL/min, measured at 150° C. with constant head pressure;

injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of 1-butanol was 5.4 min. A similar GC method using a Varian CP-WAX 58(FFAP) CB column (25 m×0.25 mm id×0.2 μm film thickness, Varian, Inc., Palo Alto, Calif.) was also used.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "M" means molar, "mmol" means millimole(s), "μmole" means micromole(s)", "g" means gram(s), "μg" means microgram(s) and "ng" means nanogram(s), "PCR" means polymerase chain reaction, "OD" means optical density, "$OD_{600}$" means the optical density measured at a wavelength of 600 nm, $OD_{550}$" means the optical density measured at a wavelength of 550 nm, "kDa" means kilodaltons, "g" means the gravitation constant, "rpm" means revolutions per minute, "bp" means base pair(s), "kbp" means kilobase pair(s), "% w/v" means weight/volume percent, % v/v" means volume/volume percent, "nt" means not tested, "HPLC" means high performance liquid chromatography, and "GC" means gas chromatography.

Example 1

Increased Tolerance of *Lactobacillus plantarum* PN0512 to 1-Butanol, Iso-Butanol and 2-Butanol at Decreased Growth Temperatures Tolerance levels of bacterial strain *Lactobacillus plantarum* PN0512 (ATCC # PTA-7727) were determined at 25° C., 30° C. and 37° C. as follows. The strain was cultured in S30L medium (i.e., 10 mM ammonium sulfate, 5 mM potassium phosphate buffer, pH 7.0, 50 mM MOPS, pH 7.0, 2 mM $MgCl_2$, 0.7 mM $CaCl_2$, 50 μM $MnCl_2$, 1 μM $FeCl_3$, 1 μM $ZnCl_2$, 1.72 μM $CuCl_2$, 2.53 μM $COCl_2$, 2.42 μM $Na_2MoO_4$, 2 μM thiamine hydrochloride, 10 mM glucose, and 0.2% yeast extract). An overnight culture in the absence of any test compound was started in 15 mL of the S30L medium in a 150 mL flask, with incubation at 37° C. in a shaking water bath. The next morning, the overnight culture was diluted into three 500 mL flasks containing 150 mL of fresh medium to an initial $OD_{600}$ of about 0.08. Each flask was incubated in a shaking water bath, one each at 25° C., 30° C. and 37° C. Each large culture was allowed to acclimate at the test temperature for at least 0.5 h. After the acclimation period, each large culture was split into flasks in the absence (control) and in the presence of various amounts of 1-butanol, isobutanol or 2-butanol, as listed in Tables 6, 7, and 8, respectively. Growth was followed by measuring $OD_{600}$ for six hours after addition of the compounds. The results are summarized in Tables 6, 7, and 8 below.

TABLE 6

Growth of *L. plantarum* PN0512 in the presence of 1-butanol at different temperatures

| Concentration 1-butanol (% w/v) | 37° C. | 30° C. | 25° C. |
|---|---|---|---|
| 0.0 | + | + | + |
| 1.0 | + | nt | nt |
| 1.2 | + | nt | nt |
| 1.4 | + | nt | nt |
| 1.5 | + | + | + |
| 1.6 | + | nt | nt |
| 1.8 | + | nt | nt |
| 2.0 | + | + | + |
| 2.1 | + | nt | nt |
| 2.2 | + | nt | nt |
| 2.3 | + | nt | nt |
| 2.4 | − | + | + |
| 2.5 | − | nt | nt |
| 2.7 | − | + | nt |
| 2.9 | − | − | + |
| 3.1 | − | − | + |
| 3.2 | nt | − | − |
| 3.3 | nt | nt | − |
| 3.4 | nt | − | − |

TABLE 7

Growth of *L. plantarum* PN0512 in the presence of isobutanol at different temperatures

| Concentration isobutanol (% w/v) | 37° C. | 30° C. | 25° C. |
|---|---|---|---|
| 0.0 | + | + | + |
| 0.5 | + | nt | nt |
| 1.0 | + | nt | nt |
| 1.5 | + | + | + |
| 1.6 | + | nt | nt |
| 1.8 | + | nt | nt |
| 2.0 | + | + | + |
| 2.1 | + | nt | nt |
| 2.3 | + | nt | nt |
| 2.4 | + | + | + |
| 2.5 | + | nt | nt |
| 2.7 | + | + | + |
| 2.9 | + | + | + |
| 3.1 | + | + | + |
| 3.3 | nt | − | + |
| 3.4 | − | nt | nt |
| 3.5 | nt | nt | + |
| 3.6 | nt | nt | − |
| 3.8 | − | nt | nt |
| 4.3 | − | nt | nt |

TABLE 8

Growth of *L. plantarum* PN0512 in the presence of 2-butanol at different temperatures

| Concentration 2-butanol (% w/v) | 37° C. | 30° C. | 25° C. |
|---|---|---|---|
| 0.0 | + | + | + |
| 1.8 | + | nt | nt |
| 2.1 | + | nt | nt |
| 2.5 | + | nt | nt |
| 2.9 | + | + | + |
| 3.1 | + | nt | nt |
| 3.5 | + | nt | nt |
| 3.6 | + | nt | nt |
| 3.8 | + | + | + |
| 4.0 | nt | + | nt |
| 4.3 | + | + | + |
| 4.5 | − | + | nt |
| 4.7 | − | + | + |
| 4.9 | nt | − | + |
| 5.2 | − | nt | + |

TABLE 8-continued

Growth of *L. plantarum* PN0512 in the presence of 2-butanol at different temperatures

| Concentration 2-butanol (% w/v) | 37° C. | 30° C. | 25° C. |
|---|---|---|---|
| 5.6 | – | nt | – |
| 6.0 | – | nt | nt |
| 6.4 | – | nt | nt |
| 7.3 | – | nt | nt |

"+" = growth observed as an increase in $OD_{600}$.
"–" = no growth observed, i.e. no change in $OD_{600}$.

All three butanols showed a similar effect of temperature on growth inhibition of *L. plantarum* PN0512. The concentration that resulted in full growth inhibition was greater at 25° C. than at 37° C. In the case of 1-butanol, growth was observed at 37° C. in 2.3% 1-butanol, but not 2.4%. However, at 30° C. growth was observed in 2.7%, but not 2.9%, and at 25° C. growth was observed even in 3.1% 1-butanol. Thus, the concentration of 1-butanol that completely inhibited growth increased as growth temperature decreased. Likewise, in the case of isobutanol, growth was observed in 3.5% at 25° C. while growth was observed in 3.1% at 30° C. and 37° C., but not in 3.3% or 3.4%. Similarly, in the case of 2-butanol growth was observed at 37° C. in 4.3%, but not in 4.5%; at 30° C. in 4.7%, but not in 4.9%; and at 25° C. in 5.2%. Thus the tolerance of *L. plantarum* PN0512 to butanols increased with decreased growth temperature.

Example 2

Increased Tolerance of *Escherichia coli* to 1-Butanol at Decreased Exposure Temperature The effect of growth and exposure temperature on survival of *Escherichia coli* in the presence of 1-butanol was tested using stationary phase cultures in a rich medium and log phase cultures in a defined medium. For the stationary phase studies, *E. coli* strain MG1655 (ATCC #700926) was grown overnight in LB medium (Teknova, Half Moon Bay, Calif.) with shaking at 250 rpm at 42° C., 29° C. or 28° C. Survival of 1-butanol shock was tested at exposure temperatures of 0° C., 28° C. or 42° C. The 1-butanol exposure at 28° C. or 42° C. was started immediately after removing the overnight cultures from the growth incubators. The 1-butanol exposure at 0° C. was done after allowing the overnight cultures to cool on ice for about 15 min. A series of solutions of 1-butanol at different concentrations in LB medium was made and 90 μL aliquots were put in microfuge tubes. To these were added 10 μL of the overnight cultures and the tubes were immediately placed in shaking incubators at 42° C. or 28° C. or left on ice for 30 min. To stop the effect of 1-butanol on the cultures, a $10^{-2}$ dilution was done by placing 2 μL of the treated culture into 198 μL of LB medium in wells of a microplate. Then, 5 μL of the undiluted treated cultures were spotted on LB agar plates. Subsequent 10-fold serial dilutions of $10^{-3}$, $10^{-4}$, $10^{-5}$ and $10^{-6}$ of the exposed cultures were done by serial pipetting of 20 μL, starting with the $10^{-2}$ dilution cultures, into 180 μL of LB medium in the microplate, using a multi-channel pipette. Prior to each transfer, the cultures were mixed by pipetting up and down six times. Each dilution (5 μL) was spotted onto an LB plate using a multi-channel pipette and allowed to soak into the plate. The plates were inverted and incubated overnight at 37° C. The number of colonies for each dilution was counted and the % growth inhibition was calculated by comparison with a control culture that had not been exposed to 1-butanol. Survival of 0% was recorded when no colonies in the spots of the undiluted or any of the serial dilutions were observed. The results are shown in Table 9.

TABLE 9

Survival of stationary phase *E. coli* in 1-butanol at 42° C., 28° C., or 0° C.

| 1-Butanol % (w/v) | Grown at 42° C. | Grown at 29° C. | Grown at 42° C. | Grown at 28° C. | Grown at 42° C. | Grown at 29° C. |
|---|---|---|---|---|---|---|
| | % survival after 30 min exposure at 42° C. | | % survival after 30 min exposure at 28° C. | | % survival after 30 min exposure at 0° C. | |
| 1.0 | 100 | 100 | 100 | 100 | 100 | 100 |
| 1.5 | 0.1 | 0.1 | 100 | 100 | 100 | 100 |
| 2.0 | 0 | 0.1 | 100 | 100 | 100 | 100 |
| 2.5 | 0 | 0 | 100 | 100 | 100 | 100 |
| 3.0 | 0 | 0 | 100 | 100 | 100 | 100 |
| 3.5 | 0 | 0 | 3 | 10 | 100 | 100 |
| 4.0 | 0 | 0 | 0.0004 | 0.0003 | 100 | 100 |
| 5.0 | nt | nt | nt | nt | 1 | 1 |
| 6.0 | nt | nt | nt | nt | 0 | 0.001 |
| 7.0 | nt | nt | nt | nt | 0 | 0 |

A similar study was done with log-phase cultures of *E. coli* grown in a defined medium. *E. coli* strain MG1655 was allowed to grow overnight in MOPS 0.2% glucose medium (Teknova, Half Moon Bay, Calif.) at 42° C. or 28° C. The following day, the cultures were diluted into fresh medium and allowed to grow at the same temperature until in the log phase of growth. The $OD_{600}$ was 0.74 for the 28° C. culture and was 0.72 for the 42° C. culture. Both of these log phase cultures were exposed to 1-butanol at 42° C., 28° C. and 0° C. as follows. A series of solutions of 1-butanol at different concentrations in MOPS 0.2% glucose medium was made and 90 μL aliquots were put in microfuge tubes. To these were added 10 μL of the log phase cultures and the tubes were immediately placed in shaking incubators at 42° C. or 28° C. or left on ice for 30 min. To stop the effect of 1-butanol on the cultures, a $10^{-2}$ dilution was done by placing 2 μL of the treated culture into 198 μL of LB medium in wells of a microplate. Then 5 μL of the undiluted treated cultures were spotted on LB agar plates. Subsequent 10-fold serial dilutions of $10^{-3}$, $10^{-4}$, $10^{-5}$ and $10^{-6}$ of the exposed cultures were done by serial pipetting of 20 μL, starting with the $10^{-2}$ dilution cultures, into 180 μL of LB medium in the microplate, using a multi-channel pipette. Prior to each transfer, the cultures were mixed by pipetting up and down six times. Each dilution (5 μL) was spotted onto an LB plate using a multi-channel pipette and allowed to soak into the plate. The plates were inverted and incubated overnight at 37° C. The number of colonies for each dilution was counted and the % growth inhibition was calculated by comparison with a control culture that had not been exposed to 1-butanol. Survival of 0% was recorded when no colonies in the spots of the undiluted or any of the serial dilutions were observed. The results are shown in Table 10.

TABLE 10

Survival of log-phase *E. coli* in 1-butanol at 42° C., 28° C., or 0° C.

| 1-Butanol % (w/v) | Grown at 42° C. | Grown at 28° C. | Grown at 42° C. | Grown at 28° C. | Grown at 42° C. | Grown at 29° C. |
|---|---|---|---|---|---|---|
| | % survival after 30 min exposure at 42° C. | | % survival after 30 min exposure at 28° C. | | % survival after 30 min exposure at 0° C. | |
| 1.0 | 100 | 100 | nt | nt | nt | nt |
| 1.5 | 0 | 0 | 100 | 100 | nt | nt |
| 2.0 | 0 | 0 | 100 | 100 | nt | nt |
| 2.5 | 0 | 0 | 0.1 | 50 | 100 | 100 |
| 3.0 | 0 | 0 | 0 | 0 | 100 | 100 |
| 3.5 | 0 | 0 | 0.01 | 0 | 100 | 100 |
| 4.0 | 0 | 0 | 0.001 | 0 | 100 | 100 |
| 4.5 | nt | nt | 0 | 0 | 100 | 100 |
| 5.0 | nt | nt | nt | nt | 10 | 50 |
| 6.0 | nt | nt | nt | nt | 1 | 1 |

For both the stationary phase and log-phase cultures of *E. coli* MG1655, the growth temperature had very little, if any, effect on the survival of a 1-butanol shock. However, the exposure temperature had a major effect on the survival of *E. coli* to 1-butanol shock. As can be seen from the data in Tables 9 and 10, the tolerance of *E. coli* MG1655 to 1-butanol increased with decreasing exposure temperature.

Example 3

Increased Tolerance of *Escherichia Coli* to 2-Butanone at Decreased Exposure Temperature The effect of exposure temperature on survival of *Escherichia coli* in the presence of 2-butanone (also referred to herein as methyl ethyl ketone or MEK) was tested as follows. *E. coli* strain BW25113 (The Coli Genetic Stock Center (CGSC), Yale University; #7636) was grown overnight in LB medium (Teknova, Half Moon Bay, Calif.) with shaking at 250 rpm at 37° C. Survival of MEK shock was tested at exposure temperatures of 28° C. or 37° C. A series of solutions of MEK at different concentrations in LB medium was made and 90 μL aliquots were put in microfuge tubes. To these were added 10 μL of the overnight culture and the tubes were immediately placed in shaking incubators at 37° C. or 28° C. for 30 min. To stop the effect of MEK on the cultures, a $10^{-2}$ dilution was done by placing 2 μL of the MEK treated culture into 198 μL of LB medium in wells of a microplate. Then 5 μL of the undiluted treated cultures were spotted on LB agar plates. Subsequent 10-fold serial dilutions of $10^{-3}$, $10^{-4}$, $10^{-5}$ and $10^{-6}$ of the exposed cultures were done by serial pipetting of 20 μL, starting with the $10^{-2}$ dilution cultures, into 180 μL of LB medium in the microplate, using a multi-channel pipette. Prior to each transfer, the cultures were mixed by pipetting up and down six times. Each dilution (5 μL) was spotted onto LB plates using a multi-channel pipette and allowed to soak into the plate. The plates were inverted and incubated overnight at 37° C. The number of colonies for each dilution was counted and the % growth inhibition was calculated by comparison with a control culture that had not been exposed to MEK. Survival of 0% was recorded when no colonies in the spots of the undiluted or any of the serial dilutions were observed. The results, given as the average of duplicate experiments, are shown in Table 11.

TABLE 11

Survival of *E. coli* in MEK at 37° C. and 28° C.

| MEK % w/v | % Survival at 37° C. | % Survival at 28° C. |
|---|---|---|
| 0 | 100 | 100 |
| 4 | 100 | 100 |
| 6 | 0 | 100 |
| 8 | 0 | 0.002 |

Reducing the exposure temperature from 37° C. to 28° C. dramatically improved survival of *E. coli* to MEK treatment. At 37° C. there was full survival at 4% w/v and no survival at 6% w/v, while at 28° C. there was full survival at 6% w/v. Thus, the tolerance of *E. coli* to MEK increased with decreasing exposure temperature.

Example 4

Increased Tolerance of *E. Coli* and *L. Plantarum* PN0512 to 1-Butanol at Decreased Exposure Temperature This Example demonstrates that the toxic effects of 1-butanol and 2-butanol on various microbial cells was reduced at lower temperatures. This was demonstrated by incubating *E. coli* (strain MG1655; ATCC #700926), and *L. plantarum* (strain PN0512; ATCC #PTA-7727) with either 1-butanol or 2-butanol at different temperatures and then determining the fraction of the cells that survived the treatment at the different temperatures.

Using overnight cultures or cells from plates, 30 mL cultures of the microorganisms to be tested were started in the following culture media:

*E. coli*—Miller's LB medium (Teknova, Half Moon Bay, Calif.):

*L. plantarum* PN0512—*Lactobacilli* MRS Broth (BD Diagnostic Systems, Sparks, Md.).

The *E. coli* and *L. plantarum* cultures were grown at 37° C. aerobically with shaking until the cultures were in log phase and the $OD_{600}$ was between 0.6 and 0.8. A 50 μL aliquot of each culture was removed for a time zero sample. The remainder of the cultures was divided into six 5 mL portions and placed in six small incubation flasks or tubes. Different amounts of 1-butanol or 2-butanol were added to the six flasks to bring the concentration to predetermined values, as listed in the tables below. The flasks or tubes were incubated at a desired temperature, aerobically without shaking for 1 h. After the incubation with one of the butanols, 2 μL from each of the flasks (and in addition 2 μL of the time zero sample of the culture before exposure to one of the butanols) were pipetted into the "head" wells of a 96 well (8×12) microtiter plate, each containing 198 μL of LB medium to give a $10^{-2}$ dilution of the culture. Subsequently, $10^{-3}$, $10^{-4}$, $10^{-5}$, and $10^{-6}$ serial dilutions of the cultures were prepared as follows. The $10^{-3}$ dilution was prepared by pipetting 20 μL of the sample from the head well into the 180 μL LB medium in the next well using a multi-channel pipette. This procedure was repeated 3 more times on successive wells to prepare the $10^{-4}$, $10^{-5}$, and $10^{-6}$ dilutions. After each liquid transfer, the solution in the well was mixed by pipetting it up and down 10 times with the multi-channel pipetor. A 5 μL aliquot of each dilution was spotted onto an LB plate using a multi-channel pipette starting with the $10^{-6}$ dilution, then the $10^{-5}$, and so on working from more to less dilute without a change of tips. The spots were allowed to soak into the agar by leaving the lid of the plate slightly open for 15 to 30 min in a sterile transfer hood. The plates were covered, inverted, and incubated overnight at 37° C. The following day, the number of colonies in the spots were counted from the different dilutions. The number of living cells/mL in each of the original culture solutions from which the 2 μL was withdrawn was calculated and compared to the number of cells in the control untreated culture to determine the % of the cells surviving.

The results of experiments in which *E. coli* cells were treated with 1-butanol at temperatures of 0, 30, and 37° C. are shown Table 12.

TABLE 12

Percentage of *E. coli* cells surviving in 1-butanol at 0, 30 and 37° C.

| 1-butanol % v/v | % Survival at 0° C. | % Survival at 30° C. | % Survival at 37° C. |
|---|---|---|---|
| 0 | 100 | 100 | 100 |
| 1 | nt | 100 | 72 |
| 1.5 | nt | 100 | 20 |
| 2 | nt | 100 | 0 |
| 2.5 | 100 | 23 | 0 |
| 3 | 100 | 0 | 0 |
| 3.5 | 100 | 0 | nt |
| 4 | 100 | nt | nt |
| 4.5 | 100 | nt | nt |

The concentration at which 1-butanol kills *E. coli* cells was affected by the treatment temperature. At 0° C., concentrations of 1-butanol as high as 4.5% v/v had no toxic effect on *E. coli* cells during a one hour treatment. At 30° C., *E. coli* cells were killed when treated with 3% v/v 1-butanol for one hour. At 37° C., *E. coli* cells were killed when treated with 2% v/v 1-butanol for one hour.

The results of experiments in which *L. plantarum* PN0512 cells were treated with 1-butanol at temperatures of 0, 23, and 37° C. for one hour are shown Table 13.

TABLE 13

Percentage of *L. plantarum* PN0512 cells surviving in 1-butanol at 0, 23 and 37° C.

| 1-butanol % v/v | % Survival at 0° C. | % Survival at 23° C. | % Survival at 37° C. |
|---|---|---|---|
| 0 | 100 | 100 | 100 |
| 1 | nt | nt | 80 |
| 1.5 | nt | nt | 58 |
| 2 | nt | 100 | 29 |
| 2.5 | nt | 100 | 8 |
| 3 | 100 | 82 | 0 |
| 3.5 | 100 | 0 | 0 |
| 4 | 100 | 0 | nt |
| 4.5 | 100 | 0 | nt |
| 5 | 0 | nt | nt |
| 5.5 | 0 | nt | nt |

The concentration at which 1-butanol kills *L. plantarum* PN0512 cells was affected by the treatment temperature. At 0° C., concentrations of 1-butanol as high as 4.5% v/v had no toxic effect on *L. plantarum* PN0512 cells during a one hour treatment. At 23° C., *L. plantarum* PN0512 cells were killed when treated with 3.5% v/v 1-butanol for one hour. At 37° C., *L. plantarum* PN0512 cells were killed when treated with 2.5% v/v 1-butanol for one hour.

Example 5

Cloning and Expression of Acetyl-CoA Acetyltransferase

The purpose of this Example was to express the enzyme acetyl-CoA acetyltransferase, also referred to herein as acetoacetyl-CoA thiolase, in *E. coli*. The acetoacetyl-CoA thiolase gene thlA was cloned from *C. acetobutylicum* (ATCC 824) and expressed in *E. coli*. The thlA gene was amplified from *C. acetobutylicum* (ATCC 824) genomic DNA using PCR, resulting in a 1.2 kbp product.

The genomic DNA from *Clostridium acetobutylicum* (ATCC 824) was either purchased from the American Type Culture Collection (ATCC, Manassas, Va.) or was isolated from *Clostridium acetobutylicum* (ATCC 824) cultures, as described below.

Genomic DNA from *Clostridium acetobutylicum* (ATCC 824) was prepared from anaerobically grown cultures. The *Clostridium* strain was grown in 10 mL of Clostridial growth medium (Lopez-Contreras et al., *Appl. Env. Microbiol.* 69(2), 869-877 (2003)) in stoppered and crimped 100 mL Bellco serum bottles (Bellco Glass Inc., Vineland, N.J.) in an anaerobic chamber at 30° C. The inoculum was a single colony from a 2×YTG plate (Kishii, et al., *Antimicrobial Agents & Chemotherapy,* 47(1), 77-81 (2003)) grown in a 2.5 L MGC AnaeroPak™ (Mitsubishi Gas Chemical America Inc, New York, N.Y.) at 37° C.

Genomic DNA was prepared using the Gentra Puregene® kit (Gentra Systems, Inc., Minneapolis, Minn.; catalog no. D-6000A) with modifications to the manufacturer's instruction (Wong et al., *Current Microbiology,* 32, 349-356 (1996)). The thlA gene was amplified from *Clostridium acetobutylicum* (ATCC 824) genomic DNA by PCR using primers N7 and N8 (see Table 4), given as SEQ ID NOs:21 and 22, respectively. Other PCR amplification reagents were supplied in manufacturers' kits for example, Kod HiFi DNA Polymerase (Novagen Inc., Madison, Wis.; catalog no. 71805-3) and used according to the manufacturer's protocol. Amplification was carried out in a DNA Thermocycler GeneAmp 9700 (PE Applied Biosystems, Foster city, CA).

For expression studies the Gateway cloning technology (Invitrogen Corp., Carlsbad, Calif.) was used. The entry vector pENTR/SD/D-TOPO allowed directional cloning and provided a Shine-Dalgarno sequence for the gene of interest. The destination vector pDEST14 used a T7 promoter for expression of the gene with no tag. The forward primer incorporated four bases (CACC) immediately adjacent to the translational start codon to allow directional cloning into pENTR/SD/D-TOPO (Invitrogen) to generate the plasmid pENTRSDD-TOPOthlA. The pENTR construct was transformed into *E. coli* Top10 (Invitrogen) cells and plated according to manufacturer's recommendations. Transformants were grown overnight and plasmid DNA was prepared using the QIAprep Spin Miniprep kit (Qiagen, Valencia, Calif.; catalog no. 27106) according to manufacturer's recommendations. Clones were submitted for sequencing with M13 Forward and Reverse primers (see Table 5), given as SEQ ID NOs:45 and 46, respectively, to confirm that the genes inserted in the correct orientation and to confirm the sequence. Additional sequencing primers, N7SeqF1 and N7SeqR1 (see Table 5), given as SEQ ID NOs:47 and 48, respectively, were needed to completely sequence the PCR product. The nucleotide sequence of the open reading frame (ORF) for this gene and the predicted amino acid sequence of the enzyme are given as SEQ ID NO:1 and SEQ ID NO:2, respectively.

To create an expression clone, the thlA gene was transferred to the pDEST 14 vector by recombination to generate pDEST14thlA. The pDEST14thlA vector was transformed into BL21-AI cells. Transformants were inoculated into LB medium supplemented with 50 μg/mL of ampicillin and grown overnight. An aliquot of the overnight culture was used to inoculate 50 mL of LB supplemented with 50 μg/mL of ampicillin. The culture was incubated at 37° C. with shaking until the $OD_{600}$ reached 0.6-0.8. The culture was split into two 25-mL cultures and arabinose was added to one of the flasks to a final concentration of 0.2% by weight. The negative control flask was not induced with arabinose. The flasks were incubated for 4 h at 37° C. with shaking. Cells were harvested by centrifugation and the cell pellets were resuspended in 50 mM MOPS, pH 7.0 buffer. The cells were disrupted either by sonication or by passage through a French Pressure Cell. The whole cell lysate was centrifuged yielding the supernatant or cell free extract and the pellet or the insoluble fraction. An aliquot of each fraction (whole cell lysate, cell free extract and insoluble fraction) was resuspended in SDS (MES) loading buffer (Invitrogen), heated to 85° C. for 10 min and subjected to SDS-PAGE analysis (NuPAGE 4-12% Bis-Tris Gel, catalog no. NPO322Box, Invitrogen). A protein of the expected molecular weight of about 41 kDa, as deduced from the nucleic acid sequence, was present in the induced culture but not in the uninduced control.

Acetoacetyl-CoA thiolase activity in the cell free extracts was measured as degradation of a $Mg2^+$-acetoacetyl-CoA complex by monitoring the decrease in absorbance at 303 nm. Standard assay conditions were 100 mM Tris-HCl pH 8.0, 1 mM DTT (dithiothreitol) and 10 mM $MgCl_2$. The cocktail was equilibrated for 5 min at 37° C.; then the cell-free extract was added. The reaction was initiated with the addition of 0.05 mM acetoacetyl-CoA plus 0.2 mM CoA. Protein concentration was measured by either the Bradford method or by the Bicinchoninic Kit (Sigma, catalog no. BCA-1). Bovine serum albumin (Bio-Rad, Hercules, Calif.) was used as the standard in both cases. In one typical assay, the specific activity of the ThlA protein in the induced culture was determined to be 16.0 μmol $mg^{-1}$ $min^{-1}$ compared to 0.27 μmol $mg^{-1}$ $min^{-1}$ in the uninduced culture.

Example 6

Cloning and Expression of Acetyl-CoA Acetyltransferase

The purpose of this Example was to express the enzyme acetyl-CoA acetyltransferase, also referred to herein as acetoacetyl-CoA thiolase, in *E. coli*. The acetoacetyl-CoA thiolase gene thlB was cloned from *C. acetobutylicum* (ATCC 824) and expressed in *E. coli*. The thlB gene was amplified from *C. acetobutylicum* (ATCC 824) genomic DNA using PCR.

The thlB gene was cloned and expressed in the same manner as the thlA gene described in Example 5. The *C. acetobutylicum* (ATCC 824) genomic DNA was amplified by PCR using primers N15 and N16 (see Table 4), given as SEQ ID NOs:27 and 28, respectively, creating a 1.2 kbp product. The forward primer incorporated four bases (CCAC) immediately adjacent to the translational start codon to allow directional cloning into pENTR/SD/D-TOPO (Invitrogen) to generate the plasmid pENTRSDD-TOPOthlB. Clones were submitted for sequencing with M13 Forward and Reverse primers, given as SEQ ID NOs:45 and 46 respectively, to confirm that the genes inserted in the correct orientation and to confirm the sequence. Additional sequencing primers, N15SeqF1 and N16SeqR1 (see Table 5), given as SEQ ID NOs:49 and 50 respectively, were needed to completely sequence the PCR product. The nucleotide sequence of the open reading frame (ORF) for this gene and the predicted amino acid sequence of the enzyme are given as SEQ ID NO:3 and SEQ ID NO:4, respectively.

To create an expression clone, the thlB gene was transferred to the pDEST 14 (Invitrogen) vector by recombination to generate pDEST14thlB. The pDEST14thlB vector was transformed into BL21-AI cells and expression from the T7 promoter was induced by addition of arabinose. A protein of the expected molecular weight of about 42 kDa, as deduced from the nucleic acid sequence, was present in the induced culture, but not in the uninduced control. Enzyme assays were performed as described in Example 5. In one typical assay, the specific activity of the ThlB protein in the induced culture was determined to be 14.9 μmol $mg^{-1}$ $min^{-1}$ compared to 0.28 μmol $mg^{-1}$ $min^{-1}$ in the uninduced culture.

Example 7

Cloning and Expression of 3-Hydroxybutyryl-CoA Dehydrogenase

The purpose of this Example was to clone the hbd gene from *C. acetobutylicum* (ATCC 824) and express it in *E. coli*. The hbd gene was amplified from *C. acetobutylicum* (ATCC 824) genomic DNA using PCR.

The hbd gene was cloned and expressed using the method described in Example 5. The hbd gene was amplified from *C. acetobutylicum* (ATCC 824) genomic DNA by PCR using primers N5 and N6 (see Table 4) given as SEQ ID NOs:19 and 20 respectively, creating a 881 bp product. The forward primer incorporated four bases (CACC) immediately adjacent to the translational start codon to allow directional cloning into pENTR/SD/D-TOPO (Invitrogen) to generate the plasmid pENTRSDD-TOPOhbd. Clones were submitted for sequencing with M13 Forward and Reverse primers, given as SEQ ID NOs:45 and 46 respectively, to confirm that the genes inserted in the correct orientation and to confirm the sequence. Additional sequencing primers, N5SeqF2 and N6SeqR2 (see Table 5), given as SEQ ID NOs:51 and 52 respectively, were needed to completely sequence the PCR product. The nucleotide sequence of the open reading frame (ORF) for this gene and the predicted amino acid sequence of the enzyme are given as SEQ ID NO:5 and SEQ ID NO:6, respectively.

To create an expression clone, the hbd gene was transferred to the pDEST 14 (Invitrogen) vector by recombination to generate pDEST14hbd. The pDEST14hbd vector was transformed into BL21-AI cells and expression from the T7 promoter was induced by addition of arabinose, as described in Example 5. A protein of the expected molecular weight of about 31 kDa, as deduced from the nucleic acid sequence, was present in the induced culture, but was absent in the uninduced control.

Hydroxybutyryl-CoA dehydrogenase activity was determined by measuring the rate of oxidation of NADH as measured by the decrease in absorbance at 340 nm. A standard assay mixture contained 50 mM MOPS, pH 7.0, 1 mM DTT and 0.2 mM NADH. The cocktail was equilibrated for 5 min at 37° C. and then the cell free extract was added. Reactions were initiated by addition of the substrate, 0.1 mM acetoacetyl-CoA. In one typical assay, the specific activity of the BHBD protein in the induced culture was determined to be 57.4 μmol $mg^{-1}$ $min^{-1}$ compared to 0.885 μmol $mg^{-1}$ $min^{-1}$ in the uninduced culture.

Example 8

Cloning and Expression of Crotonase

The purpose of this Example was to clone the crt gene from *C. acetobutylicum* (ATCC 824) and express it in *E. coli*. The crt gene was amplified from *C. acetobutylicum* (ATCC 824) genomic DNA using PCR.

The crt gene was cloned and expressed using the method described in Example 5. The crt gene was amplified from *C. acetobutylicum* (ATCC 824) genomic DNA by PCR using primers N3 and N4 (see Table 4), given as SEQ ID NOs:17 and 18, respectively, creating a 794 bp product. The forward primer incorporated four bases (CACC) immediately adjacent to the translational start codon to allow directional cloning into pENTR/SD/D-TOPO (Invitrogen) to generate the plasmid pENTRSDD-TOPOcrt. Clones were submitted for sequencing with M13 Forward and Reverse primers, given as SEQ ID NOs:45 and 46 respectively, to confirm that the genes inserted in the correct orientation and to confirm the sequence. The nucleotide sequence of the open reading frame (ORF) for this gene and its predicted amino acid sequence are given as SEQ ID NO:7 and SEQ ID NO:8, respectively.

To create an expression clone, the crt gene was transferred to the pDEST 14 (Invitrogen) vector by recombination to generate pDEST14crt. The pDEST14crt vector was transformed into BL21-AI cells and expression from the T7 promoter was induced by addition of arabinose, as described in Example 5. A protein of the expected molecular weight of about 28 kDa, as deduced from the nucleic acid sequence, was present in much greater amounts in the induced culture than in the uninduced control.

Crotonase activity was assayed as described by Stern (*Methods Enzymol.* 1, 559-566, (1954)). In one typical assay, the specific activity of the crotonase protein in the induced culture was determined to be 444 μmol $mg^{-1}$ $min^{-1}$ compared to 47 μmol $mg^{-1}$ $min^{-1}$ in the uninduced culture.

Example 9

Cloning and Expression of Butyryl-CoA Dehydrogenase

The purpose of this Example was to express the enzyme butyryl-CoA dehydrogenase, also referred to herein as trans-2-Enoyl-CoA reductase, in *E. coli*. The CAC0462 gene, a putative trans-2-enoyl-CoA reductase homolog, was cloned from *C. acetobutylicum* (ATCC 824) and expressed in *E. coli*. The CAC0462 gene was amplified from *C. acetobutylicum* (ATCC 824) genomic DNA using PCR.

The CAC0462 gene was cloned and expressed using the method described in Example 5. The CAC0462 gene was amplified from *C. acetobutylicum* (ATCC 824) genomic DNA by PCR using primers N17 and N21 (see Table 4), given as SEQ ID NOs:29 and 30, respectively, creating a 1.3 kbp product. The forward primer incorporated four bases (CACC) immediately adjacent to the translational start codon to allow directional cloning into pENTR/SD/D-TOPO (Invitrogen) to generate the plasmid pENTRSDD-TOPOCAC0462. Clones were submitted for sequencing with M13 Forward and Reverse primers, given as SEQ ID NO:45 and 46 respectively, to confirm that the genes inserted in the correct orientation and to confirm the sequence. Additional sequencing primers, N22SeqF1 (SEQ ID NO:53), N22SeqF2 (SEQ ID NO:54), N22SeqF3 (SEQ ID NO:55), N23SeqR1 (SEQ ID NO:56), N23SeqR2 (SEQ ID NO:57), and N23SeqR3 (SEQ ID NO:58) (see Table 5) were needed to completely sequence the PCR product. The nucleotide sequence of the open reading frame (ORF) for this gene and the predicted amino acid sequence of the enzyme are given as SEQ ID NO:9 and SEQ ID NO:10, respectively.

To create an expression clone, the CAC0462 gene was transferred to the pDEST 14 (Invitrogen) vector by recombination to generate pDEST14CAC0462. The pDEST14CA0462 vector was transformed into BL21-AI cells and expression from the T7 promoter was induced by addition of arabinose, as described in Example 5. Analysis by SDS-PAGE showed no overexpressed protein of the expected molecular weight in the negative control or in the induced culture. The *C. acetobutylicum* CAC0462 gene used many rare *E. coli* codons. To circumvent problems with codon usage the pRARE plasmid (Novagen) was transformed into BL21-AI cells harboring the pDEST14CAC0462 vector. Expression studies with arabinose induction were repeated with cultures carrying the pRARE vector. A protein of the expected molecular weight of about 46 kDa was present in the induced culture but not in the uninduced control.

Trans-2-enoyl-CoA reductase activity was assayed as described by Hoffmeister et al. (*J. Biol. Chem.* 280, 4329-4338 (2005)). In one typical assay, the specific activity of the TER CAC0462 protein in the induced culture was determined to be 0.694 μmol $mg^{-1}$ $min^{-1}$ compared to 0.0128 μmol $mg^{-1}$ $min^{-1}$ in the uninduced culture.

Example 10

Cloning and Expression of Butyraldehyde Dehydrogenase (Acetylating)

The purpose of this Example was to clone the ald gene from *C. beijerinckii* (ATCC 35702) and express it in *E. coli*. The ald gene was amplified from *C. beijerinckii* (ATCC 35702) genomic DNA using PCR.

The ald gene was cloned and expressed using the method described in Example 5. The ald gene was amplified from *C. beijerinckii* (ATCC 35702) genomic DNA (prepared from anaerobically grown cultures, as described in Example 5) by PCR using primers N27 F1 and N28 R1 (see Table 4), given as SEQ ID NOs:31 and 32 respectively, creating a 1.6 kbp product. The forward primer incorporated four bases (CACC) immediately adjacent to the translational start codon to allow directional cloning into pENTR/SD/D-TOPO (Invitrogen) to generate the plasmid pENTRSDD-TOPOald. Clones were submitted for sequencing with M13 Forward and Reverse primers, given as SEQ ID NOs:45 and 46 respectively, to confirm that the genes inserted in the correct orientation and to confirm the sequence. Additional sequencing primers, N31SeqF2 (SEQ ID NO:59), N31SeqF3 (SEQ ID NO:60), N31SeqF4 (SEQ ID NO:61), N32SeqR1 (SEQ ID NO:72), N31SeqR2 (SEQ ID NO:62), N31SeqR3 (SEQ ID NO:63), N31SeqR4 (SEQ ID NO:64), and N31SeqR5 (SEQ ID NO:65) (see Table 5) were needed to completely sequence the PCR product. The nucleotide sequence of the open reading frame (ORF) for this gene and the predicted amino acid sequence of the enzyme are given as SEQ ID NO:11 and SEQ ID NO:12, respectively.

To create an expression clone, the ald gene was transferred to the pDEST 14 (Invitrogen) vector by recombination to generate pDEST14ald. The pDEST14ald vector was transformed into BL21-AI cells and expression from the T7 promoter was induced by addition of arabinose, as described in Example 5. A protein of the expected molecular weight of about 51 kDa, as deduced from the nucleic acid sequence, was present in the induced culture, but not in the uninduced control.

Acylating aldehyde dehydrogenase activity was determined by monitoring the formation of NADH, as measured by the increase in absorbance at 340 nm, as described by Husemann et al. (*Appl. Microbiol. Biotechnol.* 31:435-444 (1989)). In one typical assay, the specific activity of the Ald protein in the induced culture was determined to be 0.106 μmol mg$^{-1}$ min$^{-1}$ compared to 0.01 μmol mg$^{-1}$ min$^{-1}$ in the uninduced culture

Example 11

Cloning and Expression of Butanol Dehydrogenase

The purpose of this Example was to clone the bdhB gene from *C. acetobutylicum* (ATCC 824) and express it in *E. coli*. The bdhB gene was amplified from *C. acetobutylicum* (ATCC 824) genomic DNA using PCR.

The bdhB gene was cloned and expressed using the method described in Example 5. The bdhB gene was amplified from *C. acetobutylicum* (ATCC 824) genomic DNA by PCR using primers N11 and N12 (see Table 4), given as SEQ ID NOs:25 and 26, respectively, creating a 1.2 kbp product. The forward primer incorporated four bases (CACC) immediately adjacent to the translational start codon to allow directional cloning into pENTR/SD/D-TOPO (Invitrogen) to generate the plasmid pENTRSDD-TOPObdhB. The translational start codon was also changed from "GTG" to "ATG" by the primer sequence. Clones were submitted for sequencing with M13 Forward and Reverse primers, given as SEQ ID NOs:45 and 46 respectively, to confirm that the genes inserted in the correct orientation and to confirm the sequence. Additional sequencing primers, N11SeqF1 (SEQ ID NO:66), N11SeqF2 (SEQ ID NO:67), N12SeqR1 (SEQ ID NO:68), and N12SeqR2 (SEQ ID NO:69), (see Table 5) were needed to completely sequence the PCR product. The nucleotide sequence of the open reading frame (ORF) for this gene and the predicted amino acid sequence of the enzyme are given as SEQ ID NO:13 and SEQ ID NO:14, respectively.

To create an expression clone, the bdhB gene was transferred to the pDEST 14 (Invitrogen) vector by recombination to generate pDEST14bdhB. The pDEST14bdhB vector was transformed into BL21-AI cells and expression from the T7 promoter was induced by addition of arabinose, as described in Example 5. A protein of the expected molecular weight of about 43 kDa, as deduced from the nucleic acid sequence, was present in the induced culture, but not in the uninduced control.

Butanol dehydrogenase activity was determined from the rate of oxidation of NADH as measured by the decrease in absorbance at 340 nm as described by Husemann and Papoutsakis, supra. In one typical assay, the specific activity of the BdhB protein in the induced culture was determined to be 0.169 μmol mg$^{-1}$ min$^{-1}$ compared to 0.022 μmol mg$^{-1}$ min$^{-1}$ in the uninduced culture.

Example 12

Cloning and Expression of Butanol Dehydrogenase

The purpose of this Example was to clone the bdhA gene from *C. acetobutylicum* 824 and express it in *E. coli*. The bdhA gene was amplified from *C. acetobutylicum* 824 genomic DNA using PCR.

The bdhA gene was cloned and expressed using the method described in Example 5. The bdhA gene was amplified from *C. acetobutylicum* 824 genomic DNA by PCR using primers N9 and N10 (see Table 4), given as SEQ ID NOs:23 and 24, respectively, creating a 1.2 kbp product. The forward primer incorporated four bases (CACC) immediately adjacent to the translational start codon to allow directional cloning into pENTR/SD/D-TOPO (Invitrogen) to generate the plasmid pENTRSDD-TOPObdhA. Clones, given as SEQ ID NOs:45 and 46 respectively, to confirm that the genes inserted in the correct orientation and to confirm the sequence. Additional sequencing primers, N9SeqF1 (SEQ ID NO:70) and N10SeqR1 (SEQ ID NO:71), (see Table 5) were needed to completely sequence the PCR product. The nucleotide sequence of the open reading frame (ORF) for this gene and the predicted amino acid sequence of the enzyme are given as SEQ ID NO:15 and SEQ ID NO:16, respectively.

To create an expression clone, the bdhA gene was transferred to the pDEST 14 (Invitrogen) vector by recombination to generate pDEST14bdhA. The pDEST14bdhA vector was transformed into BL21-AI cells and expression from the T7 promoter was induced by addition of arabinose, as described in Example 5. A protein of the expected molecular weight of about 43 kDa, as deduced from the nucleic acid sequence, was present in the induced culture, but not in the uninduced control.

Butanol dehydrogenase activity was determined from the rate of oxidation of NADH as measured by the decrease in absorbance at 340 nm, as described by Husemann and Papoutsakis, supra. In one typical assay, the specific activity of the BdhA protein in the induced culture was determined to be 0.102 μmol mg$^{-1}$ min$^{-1}$ compared to 0.028 μmol mg$^{-1}$ min$^{-1}$ in the uninduced culture

Example 13

Construction of a Transformation Vector for the Genes in the 1-Butanol Biosynthetic Pathway—Lower Pathway To construct a transformation vector comprising the genes encoding the six steps in the 1-butanol biosynthetic pathway, the genes encoding the 6 steps in the pathway were divided into two operons. The upper pathway comprises the first four steps catalyzed by acetyl-CoA acetyltransferase, 3-hydroxybutyryl-CoA dehydrogenase, crotonase, and butyryl-CoA dehydrogenase. The lower pathway comprises the last two steps, catalyzed by butyraldehyde dehydrogenase and butanol dehydrogenase.

The purpose of this Example was to construct the lower pathway operon. Construction of the upper pathway operon is described in Example 14.

The individual genes were amplified by PCR with primers that incorporated restriction sites for later cloning and the forward primers contained an optimized *E. coli* ribosome binding site (AAAGGAGG). PCR products were TOPO cloned into the pCR 4Blunt-TOPO vector and transformed into *E. coli* Top10 cells (Invitrogen). Plasmid DNA was prepared from the TOPO clones and the sequence of the genes was verified. Restriction enzymes and T4 DNA ligase (New England Biolabs, Beverly, Mass.) were used according to manufacturer's recommendations. For cloning experiments, restriction fragments were purified by gel electrophoresis using QIAquick Gel Extraction kit (Qiagen).

After confirmation of the sequence, the genes were subcloned into a modified pUC19 vector as a cloning platform. The pUC19 vector was modified by a HindIII/SapI digest, creating pUC19dHS. The digest removed the lac promoter adjacent to the MCS (multiple cloning site), preventing transcription of the operons in the vector.

The ald gene was amplified from *C. beijerinckii* ATCC 35702 genomic DNA by PCR using primers N58 and N59 (see Table 4), given as SEQ ID NOs:41 and 42, respectively, creating a 1.5 kbp product. The forward primer incorporated the restriction sites AvaI and BstEII and a RBS (ribosome binding site). The reverse primer incorporated the HpaI restriction site. The PCR product was cloned into pCRBlunt II-TOPO creating pCRBluntII-ald. Plasmid DNA was prepared from the TOPO clones and the sequence of the genes verified with primers M13 Forward (SEQ ID NO:45), M13 Reverse (SEQ ID NO:46), N31SeqF2 (SEQ ID NO:59), N31SeqF3 (SEQ ID NO:60), N31SeqF4 (SEQ ID NO:61), N32SeqR1 (SEQ ID NO:72), N31SeqR2 (SEQ ID NO:62), N31SeqR3 SEQ ID NO:63), N31SeqR4 (SEQ ID NO:64), and N31SeqR5 (SEQ ID NO:65) (see Table 5).

The bdhB gene was amplified from *C. acetobutylicum* (ATCC 824) genomic DNA by PCR using primers N64 and N65 (see Table 4), given as SEQ ID NOs:43 and 44, respectively, creating a 1.2 kbp product. The forward primer incorporated an HpaI restriction site and a RBS. The reverse primer incorporated a PmeI and a SphI restriction site. The PCR product was cloned into pCRBlunt II-TOPO creating pCRBluntII-bdhB. Plasmid DNA was prepared from the TOPO clones and the sequence of the genes verified with primers M13 Forward (SEQ ID NO:45), M13 Reverse (SEQ ID NO:46), N11SeqF1 (SEQ ID NO:66), N11SeqF2 (SEQ ID NO:67), N12SeqR1 (SEQ ID NO:68), and N12SeqR2 (SEQ ID NO:69) (see Table 5).

To construct the lower pathway operon, a 1.2 kbp SphI and HpaI fragment from pCRBluntII-bdhB, a 1.4 kbp HpaI and SphI fragment from pCRBluntII-ald, and the large fragment from a AvaI and SphI digest of pUC19dHS were ligated together. The three-way ligation created pUC19dHS-ald-bdhB.

The pUC19dHS-ald-bdhB vector was digested with BstEII and PmeI releasing a 2.6 kbp fragment that was cloned into pBenBP, an *E. coli-Bacillus subtilis* shuttle vector. Plasmid pBenBP was created by modification of the pBE93 vector, which is described by Nagarajan, WO 93/24631 (Example 4). The *Bacillus amyloliquefaciens* neutral protease promoter (NPR), signal sequence and the phoA gene were removed from pBE93 with a NcoI/HindIII digest. The NPR promoter was PCR amplified from pBE93 by primers BenF and BenBPR, given by SEQ ID NOs:73 and 75, respectively. Primer BenBPR incorporated BstEII, PmeI and HindIII sites downstream of the promoter. The PCR product was digested with NcoI and HindIII and the fragment was cloned into the corresponding sites in the vector pBE93 to create pBenBP. The lower operon fragment was subcloned into the BstEII and PmeI sites in pBenBP creating pBen-ald-bdhB.

Assays for butyraldehyde dehydrogenase and butanol dehydrogenase activity were conducted on crude extracts using the methods described above. Both enzyme activities were demonstrated at levels above the control strain that contained an empty vector.

Example 14 (Prophetic)

Construction of a Transformation Vector for the Genes in the 1-Butanol Biosynthetic Pathway—Upper Pathway The purpose of this prophetic Example is to describe how to assemble the upper pathway operon. The general approach is the same as described in Example 13.

The thlA gene is amplified from *C. acetobutylicum* (ATCC 824) genomic DNA by PCR using primer pair N44 and N45 (see Table 4), given as SEQ ID NOs:33 and 34, respectively, creating a 1.2 kbp product. The forward primer incorporates a SphI restriction site and a ribosome binding site (RBS). The reverse primer incorporates AscI and PstI restriction sites. The PCR product is cloned into pCR4 Blunt-TOPO creating pCR4 Blunt-TOPO-thlA. Plasmid DNA is prepared from the TOPO clones and the sequence of the genes is verified with primers M13 Forward (SEQ ID NO:45), M13 Reverse (SEQ ID NO:46), N7SeqF1 (SEQ ID NO:47), and N7SeqR1 (SEQ ID NO:48) (see Table 5).

The hbd gene is amplified from *C. acetobutylicum* (ATCC 824) genomic DNA by PCR using primer pair N42 and N43 (see Table 4) given as SEQ ID NOs:35 and 36, respectively, creating a 0.9 kbp product. The forward primer incorporates a SalI restriction site and a RBS. The reverse primer incorporates a SphI restriction site. The PCR product is cloned into pCR4 Blunt-TOPO creating pCR4 Blunt-TOPO-hbd. Plasmid DNA is prepared from the TOPO clones and the sequence of the genes verified with primers M13 Forward (SEQ ID NO:45), M13 Reverse (SEQ ID NO:46), N5SeqF2 (SEQ ID NO:51), and N6SeqR2 (SEQ ID NO:52) (see Table 5).

The CAC0462 gene is codon optimized for expression in *E. coli* as primary host and *B. subtilis* as a secondary host. The new gene called CaTER, given as SEQ ID NO:76, is synthesized by Genscript Corp (Piscataway, N.J.). The gene CaTER is cloned in the pUC57 vector as a BamHI-SalI fragment and includes a RBS, producing plasmid pUC57-CaTER.

The crt gene is amplified from *C. acetobutylicum* (ATCC 824) genomic DNA by PCR using primer pair N38 and N39 (see Table 4), given as SEQ ID NOs:39 and 40, respectively, creating a 834 bp product. The forward primer incorporates EcoRI and MluI restriction sites and a RBS. The reverse primer incorporates a BamHI restriction site. The PCR product is cloned into pCR4 Blunt-TOPO creating pCR4 Blunt-TOPO-crt. Plasmid DNA is prepared from the TOPO clones and the sequence of the genes is verified with primers M13 Forward (SEQ ID NO:45) and M13 Reverse (SEQ ID NO:46) (see Table 5).

After confirmation of the sequence, the genes are subcloned into a modified pUC19 vector as a cloning platform. The pUC19 vector was modified by a SphI/SapI digest, creating pUC19dSS. The digest removed the lac promoter adjacent to the MCS, preventing transcription of the operons in the vector.

To construct the upper pathway operon pCR4 Blunt-TOPO-crt is digested with EcoRI and BamHI releasing a 0.8 kbp crt fragment. The pUC19dSS vector is also digested with EcoRI and BamHI releasing a 2.0 kbp vector fragment. The crt fragment and the vector fragment are ligated together using T4 DNA ligase (New England Biolabs) to form pUC19dSS-crt. The CaTER gene is inserted into pCU19dSS-crt by digesting pUC57-CaTER with BamHI and SalI, releasing a 1.2 kbp CaTER fragment. The pUC19dSS-crt is digested with BamHI and SalI and the large vector fragment is ligated with the CaTER fragment, creating pUC19dSS-crt-CaTER. To complete the operon a 884 bp SalI and SphI fragment from pCR4 Blunt-TOPO-hbd, a 1.2 kb SphI and PstI thlA fragment from pCR4 Blunt-TOPO-thlA and the large fragment from a SalI and PstI digest of pUC19dSS-crt-CaTER are ligated. The product of the 3-way ligation is pUC19dSS-crt-CaTER-hbd-thlA.

The pUC19dSS-crt-CaTER-hbd-thlA vector is digested with MluI and AscI releasing a 4.1 kbp fragment that is cloned into a derivative of pBE93 (Caimi, WO2004/018645, pp. 39-40) an *E. coli-B. subtilis* shuttle vector, referred to as pBenMA. Plasmid pBenMA was created by modification of the pBE93 vector. The *Bacillus amyloliquefaciens* neutral protease promoter (NPR), signal sequence and the phoA gene are removed from pBE93 with a NcoI/HindIII digest. The NPR promoter is PCR amplified from pBE93 by primers BenF and BenMAR, given as SEQ ID NOS:73 and 74, respectively. Primer BenMAR incorporates MluI, AscI, and HindIII sites downstream of the promoter. The PCR product was digested with NcoI and HindIII and the fragment is cloned into the corresponding sites in the vector pBE93, creating pBenMA. The upper operon fragment is subcloned into the MluI and AscI sites in pBenMA creating pBen-crt-hbd-CaTER-thlA.

Example 15 (Prophetic)

Expression of the 1-Butanol Biosynthetic Pathway in *E. coli*

The purpose of this prophetic Example is to describe how to express the 1-butanol biosynthetic pathway in *E. coli.*

The plasmids pBen-crt-hbd-CaTER-thlA and pBen-ald-bdhB, constructed as described in Examples 14 and 13, respectively, are transformed into *E. coli* NM522 (ATCC 47000) and expression of the genes in each operon is monitored by SDS-PAGE analysis, enzyme assay and Western analysis. For Westerns, antibodies are raised to synthetic peptides by Sigma-Genosys (The Woodlands, Tex.). After confirmation of expression of all the genes, pBen-ald-bdhB is digested with EcoRI and PmeI to release the NPR promoter-ald-bdhB fragment. The EcoRI digest of the fragment is blunt ended using the Klenow fragment of DNA polymerase (New England Biolabs, catalog no. M0210S). The plasmid pBen-crt-hbd-CaTER-thlA is digested with PvuII to create a linearized blunt ended vector fragment. The vector and NPR-ald-bdhB fragment are ligated, creating p1B1 O.1 and p1B1 O.2, containing the complete 1-butanol biosynthetic pathway with the NPR promoter-ald-bdhB fragment in opposite orientations. The plasmids p1B1 O.1 and p1B1 O.2 are transformed into *E. coli* NM522 and expression of the genes are monitored as previously described.

*E. coli* strain NM522/p1B1 O.1 or NM522/p1B1 O.1 is inoculated into a 250 mL shake flask containing 50 mL of medium and shaken at 250 rpm and 35° C. The medium is composed of: dextrose, 5 g/L; MOPS, 0.05 M; ammonium sulfate, 0.01 M; potassium phosphate, monobasic, 0.005 M; S10 metal mix, 1% (v/v); yeast extract, 0.1% (w/v); casamino acids, 0.1% (w/v); thiamine, 0.1 mg/L; proline, 0.05 mg/L; and biotin 0.002 mg/L, and is titrated to pH 7.0 with KOH. S10 metal mix contains: $MgCl_2$, 200 mM; $CaCl_2$, 70 mM; $MnCl_2$, 5 mM; $FeCl_3$, 0.1 mM; $ZnCl_2$, 0.1 mM; thiamine hydrochloride, 0.2 mM; $CuSO_4$, 172 μM; $COCl_2$, 253 μM; and $Na_2MoO_4$, 242 μM. After 18 to 24 h, 1-butanol is detected by HPLC or GC analysis, as described in the General Methods section.

Example 16 (Prophetic)

Expression of the 1-Butanol Biosynthetic Pathway in *Bacillus subtilis*

The purpose of this prophetic Example is to describe how to express the 1-butanol biosynthetic pathway in *Bacillus subtilis*. The same approach as described in Example 15 is used.

The upper and lower operons constructed as described in Examples 14 and 13, respectively, are used. The plasmids p1B1 O.1 and p1B1 O.2 are transformed into *Bacillus subtilis* BE1010 (*J. Bacteriol.* 173:2278-2282 (1991)) and expression of the genes in each operon is monitored as previously described.

*B. subtilis* strain BE1010/p1B1 O.1 or BE1010/p1B1 O.2 is inoculated into a 250 mL shake flask containing 50 mL of medium and shaken at 250 rpm and 35° C. for 18 h. The medium is composed of: dextrose, 5 g/L; MOPS, 0.05 M; glutamic acid, 0.02 M; ammonium sulfate, 0.01 M; potassium phosphate, monobasic buffer, 0.005 M; S10 metal mix (as described in Example 15), 1% (v/v); yeast extract, 0.1% (w/v); casamino acids, 0.1% (w/v); tryptophan, 50 mg/L; methionine, 50 mg/L; and lysine, 50 mg/L, and is titrated to pH 7.0 with KOH. After 18 to 24 h, 1-butanol is detected by HPLC or GC analysis, as described in the General Methods section.

Example 17

Production of 1-Butanol from Glucose Using Recombinant *E. coli*

This Example describes the production of 1-butanol in *E. coli*. Expression of the genes encoding the 6 steps of the 1-butanol biosynthetic pathway was divided into three operons. The upper pathway comprised the first four steps encoded by thlA, hbd, crt and EgTER in one operon. The next step, encoded by ald, was provided by a second operon. The last step in the pathway, encoded by yqhD, was provided in a third operon. 1-Butanol production was demonstrated in *E. coli* strains comprising the three operons.

Unless otherwise indicated in the text, cloning primers described in this Example are referenced by their SEQ ID NO in Table 4, and sequencing and PCR screening primers are referenced by their SEQ ID NO in Table 5.

Acetyl-CoA acetyltransferase. The thlA gene was amplified from *C. acetobutylicum* (ATCC 824) genomic DNA by PCR using primer pair N44 and N45 (see Table 4), given as SEQ ID NOs:33 and 34, respectively, creating a 1.2 kbp product. The forward primer incorporated a SphI restriction site and a ribosome binding site (RBS). The reverse primer incorporated AscI and PstI restriction sites. The PCR product was cloned into pCR4Blunt-TOPO (Invitrogen Corp., Carlsbad, Calif.) creating pCR4Blunt-TOPO-thlA. Plasmid DNA was prepared from the TOPO clones and the sequence of the genes was verified with primers M13 Forward (SEQ ID NO:45), M13 Reverse (SEQ ID NO:46), N7SeqF1 (SEQ ID NO:47), and N7SeqR1 (SEQ ID NO:48) (see Table 5).

3-Hydroxybutyryl-CoA dehydrogenase. The hbd gene was amplified from *C. acetobutylicum* (ATCC 824) genomic DNA by PCR using primer pair N42 and N43 (see Table 4) given as SEQ ID NOs:35 and 36, respectively, creating a 0.9 kbp product. The forward primer incorporated a SalI restriction site and a RBS. The reverse primer incorporated a SphI restriction site. The PCR product was cloned into pCR4Blunt-TOPO creating pCR4Blunt-TOPO-hbd. Plasmid DNA was prepared from the TOPO clones and the sequence of the genes verified with primers M13 Forward (SEQ ID NO:45), M13 Reverse (SEQ ID NO:46), N5SeqF2 (SEQ ID NO:51), and N6SeqR2 (SEQ ID NO:52) (see Table 5).

Crotonase. The crt gene was amplified from *C. acetobutylicum* (ATCC 824) genomic DNA by PCR using primer pair N38 and N39 (see Table 4), given as SEQ ID NOs:39 and 40, respectively, creating a 834 bp product. The forward primer incorporated EcoRI and MluI restriction sites and a RBS. The reverse primer incorporated a BamHI restriction site. The PCR product was cloned into pCR4Blunt-TOPO creating pCR4Blunt-TOPO-crt. Plasmid DNA was prepared from the TOPO clones and the sequence of the genes was verified with primers M13 Forward (SEQ ID NO:45) and M13 Reverse (SEQ ID NO:46) (see Table 5).

Butyryl-CoA Dehydrogenase (trans-2-enoyl-CoA reductase). The CAC0462 gene was synthesized for enhanced codon usage in *E. coli* as primary host and *B. subtilis* as a secondary host. The new gene (CaTER, SEQ ID NO:76) was synthesized and cloned by Genscript Corporation (Piscataway, N.J.) in the pUC57 vector as a BamHI-SalI fragment and includes a RBS.

An alternative gene for butyryl-CoA dehydrogenase from *Euglena gracilis* (TER, GenBank No. Q5EU90) was synthesized for enhanced codon usage in *E. coli* and *Bacillus subtilis*. The gene was synthesized and cloned by GenScript Corporation into pUC57 creating pUC57::EgTER. Primers N85 and N86, (SED ID NO: 80 and 81 respectively) together with pUC57::EgTER as template DNA, provided a PCR fragment comprising 1224 bp from pUC57::EgTER DNA. The sequence of the 1224 bp is given as SEQ ID NO:77, where bp 1-1218 is the coding sequence (cds) of EgTER(opt). EgTER (opt) is a codon optimized TER gene, lacking the normal mitochondrial presequence so as to be functional in *E. coli* (Hoffmeister et al., *J. Biol. Chem.* 280:4329 (2005)).

EgTER(opt) was cloned into pCR4Blunt-TOPO and its sequence was confirmed with primers M13 Forward (SEQ ID NO:45) and M13 Reverse (SEQ ID NO:46). Additional sequencing primers N62SeqF2 (SEQ ID NO:114), N62SeqF3 (SEQ ID NO:115), N62SeqF4 (SEQ ID NO:116), N63SeqR1 (SEQ ID NO:117), N63SeqR2 (SEQ ID NO:118), N63SeqR3 (SEQ ID NO:119) and N63SeqR4 (SEQ ID NO:120) were needed to completely sequence the PCR product. The 1.2 kbp EgTER(opt) sequence was then excised with HincII and PmeI and cloned into pET23+(Novagen) linearized with HincII. Orientation of the EgTER(opt) gene to the promoter was confirmed by colony PCR screening with primers T7Primer and N63SeqR2 (SEQ ID NOs:82 and 118 respectively). The resulting plasmid, pET23+::EgTER(opt), was transformed into BL21 (DE3) (Novagen) for expression studies.

Trans-2-enoyl-CoA reductase activity was assayed as described by Hoffmeister et al., *J. Biol. Chem.* 280:4329 (2005). In a typical assay, the specific activity of the EgTER (opt) protein in the induced BL21 (DE3)/pET23+::EgTER (opt) culture was determined to be 1.9 μmol $mg^{-1}$ $min^{-1}$ compared to 0.547 μmol $mg^{-1}$ $min^{-1}$ in the uninduced culture.

The EgTER(opt) gene was then cloned into the pTrc99a vector under the control of the trc promoter. The EgTER(opt) gene was isolated as a 1287-bp BamHI/SalI fragment from $pET23^{+}$::EgTER(opt). The 4.2 kbp vector pTrc99a was linearized with BamHI/SalI. The vector and fragment were ligated creating the 5.4 kbp pTrc99a-EgTER(opt). Positive clones were confirmed by colony PCR with primers Trc99aF and N63SeqR3 (SEQ ID NOs:83 and 119 respectively) producing a 0.5 kb product.

Construction of plasmid pTrc99a-E-C-H-T comprising genes encoding acetyl-CoA acetyltransferase (thlA), 3-hydroxybutyryl-CoA dehydrogenase (hbd), crotonase (crt) and butyryl-CoA dehydrogenase (trans-2-enoyl-CoA reductase, EgTER(opt)). To initiate the construction of a four gene operon comprising the upper pathway (EgTER(opt), crt, hbd and thlA), pCR4Blunt-TOPO-crt was digested with EcoRI and BamHI releasing a 0.8 kbp crt fragment. The pUC19dSS vector (described in Example 14) was also digested with EcoRI and BamHI releasing a 2.0 kbp vector fragment. The crt fragment and the vector fragment were ligated together using T4 DNA ligase (New England Biolabs) to form pUC19dSS-crt. The CaTER gene was inserted into pUC19dSS-crt by digesting pUC57-CaTER with BamHI and SalI, releasing a 1.2 kbp CaTER fragment. The pUC19dSS-crt was digested with BamHI and SalI and the large vector fragment was ligated with the CaTER fragment, creating pUC19dSS-crt-CaTER. To complete the operon a 884 bp SalI and SphI fragment from pCR4Blunt-TOPO-hbd, a 1.2 kb SphI and PstI thlA fragment from pCR4Blunt-TOPO-thlA and the large fragment from a SalI and PstI digest of pUC19dSS-crt-CaTER were ligated. The product of the 3-way ligation was named pUC19dSS-crt-CaTER-hbd-thlA or pUC19dss::Operon1.

Higher butyryl-CoA dehydrogenase activity was obtained from pTrc99a-EgTER(opt) than from CaTER constructs, thus, an operon derived from pTrc99a-EgTER(opt) was constructed. The CaTER gene was removed from pUC19dss::Operon1 by digesting with BamHI/Sal I and gel purifying the 5327-bp vector fragment. The vector was treated with Klenow and religated creating pUC19dss::Operon 1 ΔCaTer. The 2934-bp crt-hbd-thlA (C-H-T) fragment was then isolated as a EcoRI/PstI fragment from pUC19dss:Operon 1 ΔCaTer. The C-H-T fragment was treated with Klenow to blunt the ends. The vector pTrc99a-EgTER(opt) was digested with SalI and the ends treated with Klenow. The blunt-ended vector and the blunt-ended C-H-T fragment were ligated to create pTrc99a-E-C-H-T. Colony PCR reactions were performed with primers N62SeqF4 and N5SeqF4 (SEQ ID NOs: 116 and 84 respectively) to confirm the orientation of the insert.

Construction of plasmids pBHR T7-ald and pBHR-Ptrc-ald(opt) comprising genes encoding butyraldehyde dehydrogenase (ald and ald(opt)). The PT7-ald operon was subcloned from pDEST14ald (Example 10) into the broad host range plasmid pBHR1 (MoBitec, Goettingen, Germany) to create pBHR1PT7-ald. The pBHR1 plasmid is compatible with pUC19 or pBR322 plasmids so pBHR1 PT7-ald can be used in combination with pUC19 or pBR322 derivatives carrying the upper pathway operon for 1-butanol production in

*E. coli*. The pDEST14-ald plasmid was digested with Bgl II and treated with the Klenow fragment of DNA polymerase to make blunt ends. The plasmid was then digested with EcoRI and the 2,245 bp PT7-ald fragment was gel-purified. Plasmid pBHR1 was digested with ScaI and EcoRI and the 4,883 bp fragment was gel-purified. The PT7-ald fragment was ligated with the pBHR1 vector, creating PBHR T7-ald. Colony PCR amplification of transformants with primers T-ald(BamHI) and B-ald(EgTER) (SEQ ID NOs:85 and 86 respectively) confirmed the expected 1.4 kb PCR product. Restriction mapping of PBHR T7-ald clones with EcoRI and DrdI confirmed the expected 4,757 and 2,405 bp fragments.

For butyraldehyde dehydrogenase activity assays, the plasmid PBHR T7-ald was transformed into BL21 Star™ (DE3) cells (Invitrogen) and expression from the T7 promoter was induced by addition of L-arabinose as described in Example 5. Acylating aldehyde dehydrogenase activity was determined by monitoring the formation of NADH, as measured by the increase in absorbance at 340 nm, as described in Example 10.

An alternative DNA sequence for the ald gene from *Clostridium beijerinckii* ATCC 35702 was synthesized (optimizing for codon usage in *E. coli* and *Bacillus subtilis*) and cloned into pUC57 by GenScript Corporation (Piscataway, N.J.), creating the plasmid pUC57-ald(opt). pUC57-ald(opt) was digested with SacI and SalI to release a 1498 bp fragment comprising the condon optimized gene, ald(opt) and a RBS already for *E. coli*. The sequence of the 1498 bp fragment is given as SEQ ID NO:78.

pTrc99a was digested with SacI and SalI giving a 4153 bp vector fragment, which was ligated with the 1498 bp ald(opt) fragment to create pTrc-ald(opt). Expression of the synthetic gene, ald(opt), is under the control of the IPTG-inducible Ptrc promoter.

The Ptrc-ald(opt) operon was subcloned into the broad host range plasmid pBHR1 (MoBitec) in order to be compatible with the upper pathway plasmid described above. The Ptrc-ald(opt) fragment was PCR-amplified from pTrc99A::ald (opt) with T-Ptrc(BspEI) and B-aldopt(ScaI), (SEQ ID NOs: 87 and 88 respectively) incorporating BspEI and ScaI restriction sites within the corresponding primers. The PCR product was digested with BspEI and ScaI. The plasmid pBHR1 was digested with ScaI and BspEI and the 4,883 bp fragment was gel-purified. The Ptrc-ald(opt) fragment was ligated with the pBHR1 vector, creating pBHR-PcatPtrc-ald (opt). Restriction mapping of the pBHR-PcatPtrc-ald(opt) clones with ScaI and BspEI confirmed the expected 4,883 and 1,704 bp fragments. To remove the plasmid-born cat promoter (Pcat) region, plasmid PBHR-PcatPtrc-ald(opt) was digested with BspEI and AatII and the 6,172 bp fragment was gel-purified. T-BspEIAatII and B-BspEIAatII (SEQ ID NOs: 89 and 90 respectively) were mixed in a solution containing 50 mM NaCl, 10 mM Tris-HCl, and 10 mM $MgCl_2$ (pH7.9) to a final concentration of 100 μM and hybridized by incubating at 75° C. for 5 min and slowly cooling to room temperature. The hybridized oligonucleotides were ligated with the 6,172 bp fragment, creating pBHR-Ptrc-ald(opt).

Construction of *E. coli* strains expressing butanol dehydrogenase (yghD). *E. coli* contains a native gene (yqhD) that was identified as a 1,3-propanediol dehydrogenase (U.S. Pat. No. 6,514,733). The yqhD gene has 40% identity to the gene adhB in *Clostridium*, a probable NADH-dependent butanol dehydrogenase. The yqhD gene was placed under the constitutive expression of a variant of the glucose isomerase promoter 1.6GI (SEQ ID NO:91) in *E. coli* strain MG1655 1.6yqhD:: Cm (WO 2004/033646) using λ Red technology (Datsenko and Wanner, *Proc. Natl. Acad. Sci. U.S.A.* 97:6640 (2000)). Similarly, the native promoter was replaced by the 1.5GI promoter (WO 2003/089621) (SEQ ID NO:92), creating strain MG1655 1.5GI-yqhD::Cm, thus, replacing the 1.6GI promoter of MG1655 1.6yqhD::Cm with the 1.5GI promoter.

A P1 lysate was prepared from MG1655 1.5GI yqhD::Cm and the cassette moved to expression strains, MG1655 (DE3), prepared from *E. coli* strain MG1 655 and a lambda DE3 lysogenization kit (Invitrogen), and BL21 (DE3) (Invitrogen) creating MG1655 (DE3) 1.5GI-yqhD::Cm and BL21 (DE3) 1.5GI-yqhD::Cm, respectively.

Demonstration of 1-butanol production from recombinant *E. coli*. *E. coli* strain MG1655 (DE3) 1.5GI-yqhD::Cm was transformed with plasmids pTrc99a-E-C-H-T and PBHR T7-ald to produce the strain, MG1655 (DE3) 1.5GI-yqhD:: Cm/pTrc99a-E-C-H-T/PBHR T7-ald. Two independent isolates were initially grown in LB medium containing 50 μg/mL kanamycin and 100 μg/mL carbenicillin. The cells were used to inoculate shake flasks (approximately 175 mL total volume) containing 15, 50 and 150 mL of TM3a/glucose medium (with appropriate antibiotics) to represent high, medium and low oxygen conditions, respectively. TM3a/glucose medium contained (per liter): 10 g glucose, 13.6 g $KH_2PO_4$, 2.0 g citric acid monohydrate, 3.0 g $(NH_4)_2SO_4$, 2.0 g $MgSO_4.7H_2O$, 0.2 g $CaCl_2.2H_2O$, 0.33 g ferric ammonium citrate, 1.0 mg thiamine HCl, 0.50 g yeast extract, and 10 mL trace elements solution, adjusted to pH 6.8 with $NH_4OH$. The solution of trace elements contained: citric acid $H_2O$ (4.0 g/L), $MnSO_4.H_2O$ (3.0 g/L), NaCl (1.0 g/L), $FeSO_4.7H_2O$ (0.10 g/L), $COCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L). The flasks were inoculated at a starting $OD_{600}$ of ≦0.01 units and incubated at 34° C. with shaking at 300 rpm. The flasks containing 15 and 50 mL of medium were capped with vented caps; the flasks containing 150 mL, were capped with non-vented caps to minimize air exchange. IPTG was added to a final concentration of 0.04 mM; the $OD_{600}$ of the flasks at the time of addition was ≧0.4 units.

Approximately 15 h after induction, an aliquot of the broth was analyzed by HPLC (Shodex Sugar SH1011 column) with refractive index (RI) detection and GC (Varian CP-WAX 58(FFAP) CB column, 25 m×0.25 mm id×0.2 μm film thickness) with flame ionization detection (FID) for 1-butanol content, as described in the General Methods section. The results of the 1-butanol determinations are given in Table 14.

TABLE 14

Production of 1-butanol by *E. coli* strain MG1655 (DE3) 1.5GI-yqhD::Cm/pTrc99a-E-C-H-T/pBHR T7-ald.

| Strain | $O_2$ Level | 1-butanol, mM | molar yield, % |
|---|---|---|---|
| MG1655 a | high | 0.11 | 0.2 |
| MG1655 b | high | 0.12 | 0.2 |
| MG1655 a | medium | 0.13 | 0.3 |
| MG1655 b | medium | 0.13 | 0.2 |
| MG1655 a | low | 0.15 | 0.4 |
| MG1655 b | low | 0.18 | 0.5 |

Values were determined from HPLC analysis.
Strain suffixes "a" and "b" indicate independent isolates.

The two independent isolates of MG1655 (DE3) 1.5GI-yqhD::Cm/pTrc99a-E-C-H-T/PBHR T7-ald were tested for 1-butanol production in an identical manner except that the medium contained 5 g/L yeast extract. The results are shown in Table 15.

TABLE 15

Production of 1-butanol by *E. coli* strain MG1655 (DE3) 1.5GI-yqhD::Cm/pTrc99a-E-C-H-T/pBHR T7-ald.

| Strain | $O_2$ Level | 1-butanol, mM | molar yield, % |
|---|---|---|---|
| MG1655 a | high | – | – |
| MG1655 b | high | – | – |
| MG1655 a | medium | 0.08 | 0.1 |
| MG1655 b | medium | 0.06 | 0.1 |
| MG1655 a | low | 0.14 | 0.3 |
| MG1655 b | low | 0.14 | 0.3 |

Quantitative values were determined from HPLC analysis.
"–" = not detected.
Strain suffixes "a" and "b" indicate independent isolates.

*E. coli* strain BL21 (DE3) 1.5GI-yqhD::Cm was transformed with plasmids pTrc99a-E-C-H-T and PBHR T7-ald to produce the strain, BL21 (DE3) 1.5GI-yqhD::Cm/pTrc99a-E-C-H-T/PBHR T7-ald. Two independent isolates were tested for 1-butanol production exactly as described above. The results are given in Tables 16 and 17.

TABLE 16

Production of 1-butanol by *E. coli* strain BL21 (DE3) 1.5GI-yqhD::Cm/pTrc99a-E-C-H-T/pBHR T7-ald.

| Strain | $O_2$ Level | 1-butanol, mM | molar yield, % |
|---|---|---|---|
| DE a | high | + | + |
| DE b | high | – | – |
| DE a | medium | 0.80 | 1.4 |
| DE b | medium | 0.77 | 1.4 |
| DE a | low | 0.06 | 0.2 |
| DE b | low | 0.07 | 0.2 |

Quantitative values were determined from HPLC analysis.
"–" indicates not detected.
"+" indicates positive, qualitative identification by GC with a lower detection limit than with HPLC.
Strain suffixes "a" and "b" indicate independent isolates.

TABLE 17

Production of 1-butanol by *E. coli* strain BL21 (DE3) 1.5GI-yqhD::Cm/pTrc99a-E-C-H-T/pBHR T7-ald.

| Strain | $O_2$ Level | 1-butanol, mM | molar yield, % |
|---|---|---|---|
| DE a | high | + | + |
| DE b | high | + | + |
| DE a | medium | 0.92 | 1.7 |
| DE b | medium | 1.03 | 1.9 |
| DE a | low | + | + |
| DE b | low | + | + |

Quantitative values were determined from HPLC analysis.
"–" indicates not detected.
"+" indicates positive, qualitative identification by GC with a lower detection limit than with HPLC.
Strain suffixes "a" and "b" indicate independent isolates.

*E. coli* strain MG1655 1.5GI-yqhD::Cm was transformed with plasmids pTrc99a-E-C-H-T and pBHR-Ptrc-ald(opt) to produce the strain, MG1655 1.5GI-yqhD::Cm/pTrc99a-E-C-H-T/pBHR-Ptrc-ald(opt). Two isolates were initially grown in LB medium containing 50 μg/mL kanamycin and 100 μg/mL carbenicillin. The cells were used to inoculate shake flasks (approximately 175 mL total volume) containing 50 and 150 mL of TM3a/glucose medium (with appropriate antibiotics). The flasks were inoculated at a starting $OD_{550}$ of ≦0.04 units and incubated as described above, with and without induction. IPTG was added to a final concentration of 0.4 mM; the $OD_{550}$ of the flasks at the time of addition was between 0.6 and 1.2 units. In this case, induction was not necessary for 1-butanol pathway gene expression because of the leakiness of the IPTG inducible promoters and the constitutive nature of the 1.5GI promoter; however, induction provided a wider range of expression.

Approximately 15 h after induction, an aliquot of the broth was analyzed by GC with flame ionization detection for 1-butanol content, as described above. The results are given in Table 18. For the recombinant *E. Coli* strains, 1-butanol was produced in all cases; in separate experiments, wild type *E. Coli* strains were shown to produce no detectable 1-butanol (data not shown).

TABLE 18

Production of 1-butanol by *E. coli* strain MG1655 1.5GI-yqhD::Cm/pTrc99a-E-C-H-T/pBHR-Ptrc-ald(opt).

| Strain | $O_2$ Level | 1-butanol, mM | IPTG Induction |
|---|---|---|---|
| MG1655 a | medium | 0.14 | No |
| MG 1655 b | medium | 0.14 | No |
| MG1655 a | medium | 0.03 | Yes |
| MG 1655 b | medium | 0.07 | Yes |
| MG1655 a | low | 0.04 | No |
| MG 1655 b | low | 0.04 | No |
| MG1655 a | low | 0.02 | Yes |
| MG 1655 b | low | 0.03 | Yes |

Strain suffixes "a" and "b" indicate separate isolates.

Example 18

Production of 1-Butanol from Glucose Using Recombinant *B. Subtilis*

This Example describes the production of 1-butanol in *Bacillus subtilis*. The six genes of the 1-biosynthetic pathway, encoding six enzyme activities, were split into two operons for expression. The first three genes of the pathway (thl, hbd, and crt) were integrated into the chromosome of *Bacillus subtilis* BE1010 (Payne and Jackson, *J. Bacteriol.* 173:2278-2282 (1991)). The last three genes (EgTER, ald, and bdhB) were cloned into an expression plasmid and transformed into the *Bacillus* strain carrying the integrated 1-butanol genes.

Unless otherwise indicated in the text, cloning primers described in this Example are referenced by their SEQ ID NO in Table 4, and sequencing and PCR screening primers are referenced by their SEQ ID NO in Table 5.

Integration Plasmid. Plasmid pFP988 is a *Bacillus* integration vector that contains an *E. coli* replicon from pBR322, an ampicillin antibiotic marker for selection in *E. coli* and two sections of homology to the sacB gene in the *Bacillus* chromosome that directs integration of the vector and intervening sequence by homologous recombination. Between the sacB homology regions is the Pamy promoter and signal sequence that can direct the synthesis and secretion of a cloned gene, a His-Tag and erythromycin as a selectable marker for *Bacillus*. The Pamy promoter and signal sequence is from *Bacillus amyloliquefaciens* alpha-amylase. The promoter region also contains the lacO sequence for regulation of expression by a lacI repressor protein. The sequence of pFP988 (6509 bp) is given as SEQ ID NO:79.

Since the 1-butanol pathway genes were to be expressed in the cytoplasm, the amylase signal sequence was deleted. Plasmid pFP988 was amplified with primers Pamy/lacO F and Pamy/lacO R creating a 317 bp (0.3 kbp) product that contained the Pamy/lacO promoter. The 5' end of the Pamy/lacO F primer incorporated a BsrGI restriction site followed by an EcoRI site. The 5' end of the Pamy/lacO R primer incorporated a BsrGI restriction site followed by a PmeI restriction site. The PCR product was TOPO cloned into pCR4Blunt-TOPO creating pCR4Blunt-TOPO-Pamy/lacO. Plasmid DNA was prepared from overnight cultures and submitted for sequencing with M13 Forward and M13 Reverse primers (SEQ ID NO:45 and SEQ ID NO:46, respectively) to ensure no mutation had been introduced into the promoter. A clone of pCR4Blunt-TOPO-Pamy/lacO was digested with BsrGI and the 0.3 kbp fragment was gel-purified. The vector pFP988 was digested with BsrGI resulting in deletion of 11 bp from the 5' sacB homology region and the removal of the Pamy/lacO promoter and signal sequence and His-tag. The 6 kbp BsrGI digested vector was gel-purified and ligated with Pamy/lacO BsrGI insert. The resulting plasmids were screened with primers Pamy SeqF2 and Pamy SeqR to determine orientation of the promoter. The correct clone restored the Pamy/lacO promoter to its original orientation and was named pFP988Dss.

The cassette with genes thl-crt was constructed by SOE (splicing by overlap extension). The genes were amplified using as template pUC19dss::Operon1. The thl primers were Top TF and Bot TR amplifying a 0.9 kbp product. The crt primers were Top CF and Bot CR amplifying a 1.3 kbp product. The two genes were joined by SOE with PCR amplification using primers Top TF and Bot CR generating a 2.1 kbp product that was TOPO cloned into pCR4Blunt-TOPO creating pCR4Blunt-TOPO-T-C. Clones were submitted for sequencing to confirm the sequence. The plasmid pCR4Blunt-TOPO-T-C was digested with BstEII and PmeI releasing a 2.1 kbp fragment that was gel-purified. The insert was treated with Klenow polymerase to blunt the BstEII site. Vector pFP988Dss was digested with PmeI and treated with calf intestinal alkaline phosphatase (New England BioLabs) to prevent self-ligation. The 2.1 kbp thl-crt fragment and the digested pFP988Dss were ligated and transformed into *E. coli* Top10 cells. Transformants were screened by PCR amplification with Pamy SeqF2 and N7SeqR2 for a 0.7 kbp product, the correct product was called pFP988Dss-T-C.

Construction of the thl-crt cassette created unique SalI and SpeI sites between the two genes. To add the hbd gene to the cassette, the hbd gene was subcloned from pCR4Blunt-TOPO-hbd as a 0.9 kbp SalI/SpeI fragment. Vector pFP988Dss-T-C was digested with SalI and SpeI and the 8 kbp vector fragment was gel-purified. The vector and hbd insert were ligated and transformed into *E. coli* Top10 cells. Transformants were screened by PCR amplification with primers Pamy SeqF and N3SeqF3 for a 3.0 kbp fragment. The resulting plasmid was named pFP988Dss-T-H-C.

The Pamy promoter subsequently was replaced with the Pspac promoter from plasmid pMUTIN4 (Vagner et al., Microbiol. 144:3097-3104 (1998)). The Pspac promoter was amplified from pMUTIN4 with primers Spac F and Spac R as a 0.4 kbp product and TOPO cloned into pCR4Blunt-TOPO. Transformants were screened by PCR amplification with M13 Forward and M13 Reverse primers for the presence of a 0.5 kbp insert. Positive clones were submitted for sequencing with the same primers. Plasmid pCR4Blunt-TOPO-Pspac was digested with SmaI and XhoI and the 0.3 kbp fragment was gel-purified. Vector pFP988Dss-T-H-C was digested with SmaI and XhoI and the 9 kbp vector was isolated by gel purification. The digested vector and Pspac insert were ligated and transformed into *E. coli* Top10 cells. Transformants were screened by PCR amplification with primers SpacF Seq and N7SeqR2. Positive clones gave a 0.7 kbp product. Plasmid DNA was prepared from positive clones and further screened by PCR amplification with primers SpacF Seq and N3SeqF2. Positive clones gave a 3 kbp PCR product and were named pFP988DssPspac-T-H-C.

Integration into *B. subtilis* BE1010 to form *B. subtilis* ΔsacB::T-H-C::erm #28 comprising exogenous thl, hbd, and crt genes. Competent cells of *B. subtilis* BE1010 were prepared as described in Doyle et al., *J. Bacteriol.* 144:957-966 (1980). Competent cells were harvested by centrifugation and the cell pellets were resuspended in a small volume of the cell supernatant. To 1 volume of competent cells, 2 volumes of SPII-EGTA medium (*Methods for General and Molecular Bacteriology*, P. Gerhardt et al., Eds, American Society for Microbiology, Washington, D.C. (1994)) was added. Aliquots of 0.3 mL of cells were dispensed into test tubes and the plasmid pFP988DssPspac-T-H-C was added to the tubes. Cells were incubated for 30 minutes at 37° C. with shaking, after which 0.1 mL of 10% yeast extract was added to each tube and the cells were further incubated for 60 min. Transformants were plated for selection on LB erythromycin plates using the double agar overlay method (*Methods for General and Molecular Bacteriology*, supra). Transformants were initially screened by PCR amplification with primers Pamy SeqF and N5SeqF3. Positive clones that amplified the expected 2 kbp PCR product were further screened by PCR amplification. If insertion of the cassette into the chromosome had occurred via a double crossover event then primer set sacB Up and N7SeqR2 and primer set sacB Dn and N4SeqR3 would amplify a 1.7 kbp and a 2.7 kbp product respectively. A positive clone was identified and named *B. subtilis* ΔsacB::T-H-C::erm #28.

Plasmid Expression of EgTER, ald, and bdhB genes. The three remaining 1-butanol genes were expressed from plasmid pHT01 (MoBitec). Plasmid pHT01 is a *Bacillus-E. coli* shuttle vector that replicates via a theta mechanism. Cloned proteins are expressed from the GroEL promoter fused to a lacO sequence. Downstream of the lacO is the efficient RBS from the gsiB gene followed by a MCS. The ald gene was amplified by PCR with primers AF BamHI and AR Aat2 using pUC19dHS-ald-bdhB (described in Example 13) as template, creating a 1.4 kbp product. The product was TOPO cloned into pCR4-TOPO and transformed into *E. coli* Top10 cells. Transformants were screened with M13 Forward and M13 Reverse primers. Positive clones amplified a 1.6 kbp product. Clones were submitted for sequencing with primers M13 forward and M13 reverse, N31SeqF2, N31SeqF3, N32SeqR2, N32SeqR3 and N32SeqR4. The plasmid was named pCR4TOPO-B/A-ald.

Vector pHT01 and plasmid pCR4TOPO-B/A-ald were both digested with BamHI and AatII. The 7.9 kbp vector fragment and the 1.4 kbp ald fragment were ligated together to create pHT01-ald. The ligation was transformed into *E. coli* Top10 cells and transformants were screened by PCR amplification with primers N31 SeqF1 and HT R for a 1.3 kbp product.

To add the last two steps of the pathway to the pHT01 vector, two cloning schemes were designed. For both schemes, EgTER and bdhB were amplified together by SOE. Subsequently, the EgTER-bdh fragment was either cloned into pHT01-ald creating pHT01-ald-EB or cloned into pCR4-TOPO-B/A-ald creating pCR4-TOPO-ald-EB. The ald-EgTer-bdhB fragment from the TOPO vector was then cloned into pHT01 creating pHT01-AEB.

An EgTER-bdhB fragment was PCR amplified using primers Forward 1 (E) and Reverse 2 (B), using template DNA given as SEQ ID NO:208. The resulting 2.5 kbp PCR product was TOPO cloned into pCR4Blunt-TOPO, creating pCR4Blunt-TOPO-E-B. The TOPO reaction was transformed into *E. coli* Top10 cells. Colonies were screened with M13 Forward and M13 Reverse primers by PCR amplification. Positive clones generated a 2.6 kbp product. Clones of pCR4Blunt-TOPO-E-B were submitted for sequencing with primers M13 Forward and Reverse, N62SeqF2, N62SeqF3, N62SeqF4, N63SeqR1, N63SeqR2, N63SeqR3, N11Seq F1 and N11Seq F2, N12SeqR1 and N12SeqR2.

Plasmid pCR4Blunt-TOPO-E-B was digested with HpaI and AatII to release a 2.4 kbp fragment. The E-B fragment was treated with Klenow polymerase to blunt the end and then was gel-purified. Plasmid pHT01-ald was digested with AatII and treated with Klenow polymerase to blunt the ends. The vector was then treated with calf intestinal alkaline phosphatase and was gel-purified. The E-B fragment was ligated to the linearized vector pHT01-ald, transformed into *E. coli* Top10 cells, and selected on LB plates containing 100 μg/mL ampicillin. Transformants were screened by PCR amplification with primers N3SeqF1 and N63SeqR1 to give a 2.4 kbp product. The resulting plasmid, pHT01-ald-EB, was transformed into JM103 cells, a $recA^+$ *E. coli* strain. Plasmids prepared from $recA^+$ strains form more multimers than $recA^-$ strains. *Bacillus subtilis* transforms more efficiently with plasmid multimers rather than monomers (*Methods for General and Molecular Bacteriology*, supra). Plasmid DNA was prepared from JM103 and transformed into competent *B. subtilis* ΔsacB::T-H-C::erm #28 forming strain *B. subtilis* ΔsacB::T-H-C::erm #28/pHT01-ald-EB. Competent cells were prepared and transformed as previously described. Transformants were selected on LB plates containing 5 μg/mL chloramphenicol and screened by colony PCR with the primers N31 SeqF1 and N63SeqR4 for a 1.3 kbp product.

In the alternate cloning strategy, pCR4Blunt-TOPO-E-B was digested with HpaI and AatII releasing a 2.4 kbp fragment that was gel-purified. Plasmid pCR4-TOPO-B/A-ald was digested with HpaI and AatII and the 5.4 kbp vector fragment was gel-purified. The vector fragment from pCR4-TOPO-B/A-ald was ligated with the HpaI-AatII E-B fragment creating pCR4-TOPO-ald-EB. The ligation was transformed into *E. coli* Top10 cells and the resulting transformants were screened by PCR amplification with primers N11 SeqF2 and N63SeqR4 for a 2.1 kbp product. Plasmid pCR4-TOPO-ald-EB was digested with BamHI and AatII and SphI. The BamHI/AatII digest releases a 3.9 kbp ald-EB fragment that was gel-purified. The purpose of the SphI digest was to cut the remaining vector into smaller fragments so that it would not co-migrate on a gel with the ald-EB insert. Vector pHT01 was digested with BamHI and AatII and the 7.9 kbp vector fragment was gel-purified. The vector and ald-EB insert fragments were ligated to form plasmid pHT01-AEB and transformed into *E. coli* Top10 cells. Colonies were screened by PCR amplification with primers N62SeqF4 and HT R for a 1.5 kbp product. Plasmid was prepared and transformed into JM103. Plasmid DNA was prepared from JM103 and transformed into competent *B. subtilis* ΔsacB::T-H-C::erm #28 forming strain *B. subtilis* ΔsacB::T-H-C::erm #28/pHT01-AEB. Competent BE1010 cells were prepared and transformed as previously described. *Bacillus* transformants were screened by PCR amplification with primers N31 SeqF1 and N63SeqR4 for a 1.3 kbp product.

Demonstration of 1-Butanol Production from Recombinant *B. subtilis*.

Three independent isolates of each strain of *B. subtilis* ΔsacB::T-H-C::erm #28/pHT01-ald-EB and *B. subtilis* ΔsacB::T-H-C::erm #28/pHT01-AEB were inoculated into shake flasks (approximately 175 mL total volume) containing 15 mL of medium. A *B. subtilis* BE1010 strain lacking the exogenous 1-butanol, six gene pathway was also included as a negative control. The medium contained (per liter): 10 mL of 1 M $(NH_4)_2SO_4$; 5 mL of 1 M potassium phosphate buffer, pH 7.0; 100 mL of 1 M MOPS/KOH buffer, pH 7.0; 20 mL of 1 M L-glutamic acid, potassium salt; 10 g glucose; 10 mL of 5 g/L each of L-methionine, L-tryptophan, and L-lysine; 0.1 g each of yeast extract and casamino acids; 20 mL of metal mix; and appropriate antibiotics (5 mg chloramphenicol and erythromycin for the recombinant strains). The metal mix contained 200 mM $MgCl_2$, 70 mM $CaCl_2$, 5 mM $MnCl_2$, 0.1 mM $FeCl_3$, 0.1 mM $ZnCl_2$, 0.2 mM thiamine hydrochloride, 172 μM $CuSO_4$, 253 μM $COCl_2$, and 242 μM $Na_2MoO_4$. The flasks were inoculated at a starting $OD_{600}$ of ≦0.1 units, sealed with non-vented caps, and incubated at 37° C. with shaking at approximately 200 rpm.

Approximately 24 h after inoculation, an aliquot of the broth was analyzed by HPLC (Shodex Sugar SH1011 column) with refractive index (RI) detection and GC (Varian CP-WAX 58(FFAP) CB column, 0.25 mm×0.2 μm×25 m) with flame ionization detection (FID) for 1-butanol content, as described in the General Methods section. The results of the 1-butanol determinations are given in Table 19.

TABLE 19

Production of 1-butanol by strains *B. subtilis* ΔsacB::T-H-C::erm #28/pHT01-ald-EB and *B. subtilis* ΔsacB::T-H-C::erm #28/pHT01-AEB

| Strain | 1-butanol, HPLC RI peak area | 1-butanol, mM* |
|---|---|---|
| BE1010 control | Not detected | Not detected |
| pHT01-ald-EB a | 4629 | 0.19 |
| pHT01-ald-EB b | 3969 | Not determined |
| pHT01-ald-EB c | 4306 | Not determined |
| pHT01-AEB a | 4926 | 0.16 |
| pHT01-AEB b | 3984 | Not determined |
| pHT01-AEB c | 3970 | Not determined |

*Concentration determined by GC.
Strain suffixes "a", "b", and "c" indicate separate isolates.

Example 19

Production of 1-Butanol from Glucose or Sucrose by Recombinant *E. coli*

To endow *E. coli* MG1655 with the ability to use sucrose as the carbon and energy source for 1-butanol production, a sucrose utilization gene cluster (cscBKA) from plasmid pScrI (described below) was subcloned into pBHR-Ptrc-ald(opt) (described in Example 17) in this organism. The sucrose utilization genes (cscA, cscK, and cscB) encode a sucrose hydrolase (CscA), given as SEQ ID NO:157, D-fructokinase (CscK), given as SEQ ID NO:158, and sucrose permease (CscB), given as SEQ ID NO:159. To allow constitutive expression of the three genes from their natural promoter, the sucrose-specific repressor gene, cscR, that regulates the gene cluster is not present in the construct.

Cloning and expression of the sucrose utilization gene cluster cscBKA in plasmid pBHR-Ptrc-ald(opt). The sucrose utilization gene cluster cscBKA, given as SEQ ID NO:156, was isolated from genomic DNA of a sucrose-utilizing *E. coli* strain derived from *E. coli* strain ATCC 13281. The genomic DNA was digested to completion with BamHI and EcoRI. Fragments having an average size of about 4 kbp were isolated from an agarose gel, ligated to plasmid pLitmus28 (New England Biolabs, Beverly, Mass.), which was then digested with BamHI and EcoRI. The resulting DNA was transformed into ultracompetent *E. coli* TOP10F' (Invitrogen, Carlsbad, Calif.). The transformants were plated on MacConkey agar plates containing 1% sucrose and 100 μg/mL ampicillin and screened for purple colonies. Plasmid DNA was isolated from the purple transformants and sequenced using primers M13 Forward (SEQ ID NO:45), M13 Reverse (SEQ ID NO:46), scr1 (SEQ ID NO:160), scr2 (SEQ ID NO:161), scr3 (SEQ ID NO:162), and scr4 (SEQ ID NO:163). The plasmid containing cscB, csck, and cscA (cscBKA) genes was designated pScr1.

Plasmid pScrI was digested with XhoI and treated with the Klenow fragment of DNA polymerase to make blunt ends. The plasmid was then digested with AgeI, and the 4,179 bp cscBKA gene cluster fragment was gel-purified. Plasmid pBHR-Ptrc-ald(opt) was prepared as described in Example 17 and was digested with AgeI and NaeI. The resulting 6,003 bp pBHR-Ptrc-ald(opt) fragment was gel-purified. The cscBKA fragment was ligated with the pBHR-Ptrc-ald(opt), yielding pBHR-Ptrc-ald(opt)-cscAKB. Plasmid pBHR-Ptrc-ald(opt)-cscAKB was transformed into *E. coli* NovaXG electrocompetent cells (Novagen, Madison, Wis.) and sucrose utilization was confirmed by plating the transformants on McConkey agar plates containing 2% sucrose and 25 μg/mL kanamycin. In the pBHR-Ptrc-ald(opt)-cscAKB construct, the sucrose utilization genes were cloned downstream of Ptrc-ald(opt) as a separate fragment in the order cscA, csck, and cscB.

Alternatively, the sucrose utilization genes were cloned in the opposite direction in pBHR-Ptrc-ald(opt). Plasmid pBHR-Ptrc-ald(opt) was digested with ScaI and AgeI, and the 5,971 bp pBHR-Ptrc-ald(opt) fragment was gel-purified. The 4,179 bp cscBKA fragment, prepared as described above, was ligated with the pBHR-Ptrc-ald(opt) fragment, yielding pBHR-Ptrc-ald(opt)-cscBKA. Plasmid pBHR-Ptrc-ald(opt)-cscBKA was transformed into *E. coli* NovaXG electrocompetent cells (Novagen, Madison, Wis.) and sucrose utilization was confirmed by plating the transformants on McConkey agar plates containing 2% sucrose and 25 μg/mL kanamycin. In the pBHR-Ptrc-ald(opt)-cscBKA construct, the sucrose utilization genes were cloned as a separate fragment downstream of Ptrc-ald(opt) in the order cscB, csck, and cscA.

Demonstration of 1-butanol production from glucose or sucrose using recombinant *E. coli. E. coli* strain MG1655 1.5GI-yqhD::Cm (described in Example 17) was transformed with plasmids pTrc99a-E-C-H-T (prepared as described in Example 17) and pBHR-Ptrc-ald(opt)-cscAKB or pBHR-Ptrc-ald(opt)-cscBKA to produce two strains, MG1655 1.5GI-yqhD::Cm/pTrc99a-E-C-H-T/pBHR-Ptrc-ald(opt)-cscAKB #9 and MG1655 1.5GI-yqhD::Cm/pTrc99a-E-C-H-T/pBHR-Ptrc-ald(opt)-cscBKA #1. Starter cultures of the two strains were prepared by growing the cells in LB medium containing 25 μg/mL of kanamycin and 100 μg/mL of carbenicillin. These cells were then used to inoculate shake flasks (approximately 175 mL total volume) containing 50, 70 and 150 mL of TM3a/glucose medium (with appropriate antibiotics) to represent high, medium and low oxygen conditions, respectively, as described in Example 17. A third strain, *E. coli* MG1655/pScrI, grown in TM3a/glucose medium containing 100 μg/mL carbenicillin, was used as a negative control. For each of the strains, an identical set of flasks was prepared with TM3a/sucrose medium (with appropriate antibiotics). TM3a/sucrose medium is identical to TM3a/glucose medium except that sucrose (10 g/L) replaces glucose. The flasks were inoculated at a starting $OD_{550}$ of ≦0.03 units and incubated as described in Example 17. With the exception of the negative control flasks, IPTG was added to the flasks (final concentration of 0.04 mM) when the cultures reached an $OD_{550}$ between 0.2 and 1.8 units. The cells were harvested when the $OD_{550}$ of the cultures increased at least 3-fold.

Approximately 24 h after inoculation, an aliquot of the broth was analyzed by HPLC (Shodex Sugar SH1011 column) with refractive index (RI) detection and GC (HP-INNOWax column, 30 m×0.53 mm id, 1 μm film thickness) with flame ionization detection (FID) for 1-butanol content, as described in the General Methods section.

The concentrations of 1-butanol in cultures following growth in the glucose and sucrose-containing media are given in Table 20 and Table 21, respectively. Both recombinant *E. Coli* strains containing the 1-butanol biosynthetic pathway produced 1-butanol from glucose and sucrose under all oxygen conditions, while the negative control strain produced no detectable 1-butanol.

TABLE 20

Production of 1-butanol from glucose by recombinant *E. coli* strains MG1655 1.5GI-yqhD::Cm/pTrc99a-E-C-H-T/pBHR-Ptrc-ald(opt)-cscAKB #9 and MG1655 1.5GI-yqhD::Cm/pTrc99a-E-C-H-T/pBHR-Ptrc-ald(opt)-cscBKA #1

| Strain | $O_2$ Level | 1-butanol, mM | molar yield, % |
|---|---|---|---|
| cscBKA #1 | high | 0.01 | 0.03 |
| cscBKA #1 | medium | 0.20 | 0.43 |
| cscBKA #1 | low | 0.07 | 0.21 |
| cscAKB #9 | high | 0.01 | 0.02 |
| cscAKB #9 | medium | 0.17 | 0.35 |
| cscAKB #9 | low | 0.04 | 0.12 |
| pScr1 | high | Not detected | Not detected |
| pScr1 | medium | Not detected | Not detected |
| pScr1 | low | Not detected | Not detected |

TABLE 21

Production of 1-butanol from sucrose by recombinant *E. coli* strains.

| Strain | $O_2$ Level | 1-butanol, mM | molar yield, % |
|---|---|---|---|
| cscBKA #1 | high | 0.02 | 0.10 |
| cscBKA #1 | medium | 0.02 | 0.11 |
| cscBKA #1 | low | 0.01 | 0.09 |
| cscAKB #9 | high | 0.03 | 0.11 |
| cscAKB #9 | medium | 0.03 | 0.15 |
| cscAKB #9 | low | 0.02 | 0.10 |
| pScr1 | high | Not detected | Not detected |
| pScr1 | medium | Not detected | Not detected |
| pScr1 | low | Not detected | Not detected |

Example 20

Production of 1-Butanol from Sucrose using Recombinant *B. subtilis*

This example describes the production of 1-butanol from sucrose using recombinant *Bacillus subtilis*. Two independent isolates of *B. subtilis* strain ΔsacB::T-H-C::erm #28/pHT01-ald-EB (Example 18) were examined for 1-butanol production essentially as described in Example 18. The strains were inoculated into shake flasks (approximately 175 mL total volume) containing either 20 mL or 100 mL of medium to simulate high and low oxygen conditions, respectively. Medium A was exactly as described in Example 18, except that glucose was replaced with 5 g/L of sucrose. Medium B was identical to the TM3a/glucose medium described in Example 17, except that glucose was replaced with 10 g/L sucrose and the medium was supplemented with (per L) 10 mL of a 5 g/L solution of each of L-methionine, L-tryptophan, and L-lysine. The flasks were inoculated at a starting $OD_{550}$ of ≦0.1 units, capped with vented caps, and incubated at 34° C. with shaking at 300 rpm.

Approximately 24 h after inoculation, an aliquot of the broth was analyzed by GC (HP-INNOWax column, 30 m×0.53 mm id, 1.0 μm film thickness) with FID detection for 1-butanol content, as described in the General Methods section. The results of the 1-butanol determinations are given in Table 22. The recombinant *Bacillus* strain containing the 1-butanol biosynthetic pathway produced detectable levels of 1-butanol under high and low oxygen conditions in both media.

TABLE 22

Production of 1-butanol from sucrose by *B. subtilis* strain ΔsacB::T-H-C::erm #28/pHT01-ald-EB

| Strain | Medium | $O_2$ Level | 1-BuOH, mM[1,2] |
|---|---|---|---|
| none | A | Not applicable | Not detected |
| pHT01-ald-EB a | A | high | + |
| pHT01-ald-EB b | A | high | + |
| pHT01-ald-EB a | A | low | 0.01 |
| pHT01-ald-EB b | A | low | 0.01 |
| none | B | Not applicable | Not detected |
| pHT01-ald-EB a | B | high | + |
| pHT01-ald-EB b | B | high | + |
| pHT01-ald-EB a | B | low | 0.04 |
| pHT01-ald-EB b | B | low | 0.03 |

[1]Concentration determined by GC.

[2]"+" indicates qualitative presence of 1-butanol.

Strain suffixes "a" and "b" indicate separate isolates.

Example 21

Production of 1-Butanol from Glucose and Sucrose Using Recombinant *Saccharomyces cerevisiae*

This Example describes the production of 1-butanol in the yeast *Saccharomyces cerevisiae*. Of the six genes encoding enzymes catalyzing the steps in the 1-butanol biosynthetic pathway, five were cloned into three compatible yeast 2 micron (2μ) plasmids and co-expressed in *Saccharomyces cerevisiae*. The "upper pathway" is defined as the first three enzymatic steps, catalyzed by acetyl-CoA acetyltransferase (thlA, thiolase), 3-hydroxybutyryl-CoA dehydrogenase (hbd), and crotonase (crt). The lower pathway is defined as the fourth (butyl-CoA dehydrogenase, ter) and the fifth (butyraldehyde dehydrogenase, ald) enzymatic steps of the pathway. The last enzymatic step of the 1-butanol pathway is catalyzed by alcohol dehydrogenase, which may be encoded by endogenous yeast genes, e.g., adhI and adhII.

Expression of genes in yeast typically requires a promoter, followed by the gene of interest, and a transcriptional terminator. A number of constitutive yeast promoters were used in constructing expression cassettes for genes encoding the 1-butanol biosynthetic pathway, including FBA, GPD, and GPM promoters. Some inducible promoters, e.g. GAL1, GAL10, CUP1 were also used in intermediate plasmid construction, but not in the final demonstration strain. Several transcriptional terminators were used, including FBAt, GPDt, GPMt, ERG10t, and GAL1t. Genes encoding the 1-butanol biosynthetic pathway were first subcloned into a yeast plasmid flanked by a promoter and a terminator, which yielded expression cassettes for each gene. Expression cassettes were optionally combined in a single vector by gap repair cloning, as described below. For example, the three gene cassettes encoding the upper pathway were subcloned into a yeast 2μ plasmid. The ter and ald genes were each expressed individually in the 2μ plasmids. Co-transformation of all three plasmids in a single yeast strain resulted in a functional 1-butanol biosynthetic pathway. Alternatively, several DNA fragments encoding promoters, genes, and terminators were directly combined in a single vector by gap repair cloning.

Methods for constructing plasmids and strains in yeast *Saccharomyces cerevisiae*. Basic yeast molecular biology protocols including transformation, cell growth, gene expression, gap repair recombination, etc. are described in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

The plasmids used in this Example were *E. coli-S. cerevisiae* shuttle vectors, pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). These vectors allow strain propagation in both *E. coli* and yeast strains. A yeast haploid strain BY4741 (MATa his3Δ1 leu2Δ0 met15Δ0 ura3Δ0) (Research Genetics, Huntsville, Ala., also available from ATCC 201388) and a diploid strain BY4743 (MATa/alpha his3Δ1/his3Δ1 leu2Δ0/leu2Δ0 lys2Δ0/LYS2 MET15/met15Δ0 ura3Δ0/ura3Δ0) (Research Genetics, Huntsville, Ala., also available from ATCC 201390) were used as hosts for gene cloning and expression. Construction of expression vectors for genes encoding 1-butanol biosynthetic pathway enzymes were performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a ≧21 bp sequence at both the 5' and the 3' ends that sequentially overlap with each other, and with the 5' and 3' terminus of the vector DNA. For example, to construct a yeast expression vector for "Gene X', a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the SD minimal dropout medium, and colonies are selected for growth of cultures and mini preps for plasmid DNAs. The presence of correct insert combinations can be confirmed by PCR mapping. The plasmid DNA isolated from yeast (usually low in concentration) can then be transformed into an *E. coli* strain, e.g. TOP10, followed by mini preps and restriction mapping to further verify the plasmid construct. Finally the construct can be verified by sequence analysis. Yeast transformants of positive plasmids are grown in SD medium for performing enzyme assays to characterize the activities of the enzymes expressed by the genes of interest.

Yeast cultures were grown in YPD complex medium or Synthetic Minimal dropout medium containing glucose (SD medium) and the appropriate compound mixtures that allow complementation of the nutritional selection markers on the plasmids (*Methods in Enzymology*, Volume 194*, Guide to Yeast Genetics and Molecular and Cell Biology,* 2004, Part A, pp. 13-15). The sugar component in the SD drop out medium was 2% glucose. For 1-Butanol production, yeast cultures were also grown in Synthetic Minimal dropout medium with 2% sucrose (SS medium).

For enzyme activity analysis, a single colony of each strain was streaked onto a fresh plate containing SD minimal drop out medium and incubated at 30° C. for 2 days. The cells on this plate were used to inoculate 20 mL of SD drop out medium and in a 125 mL shake flask and grown overnight at 30° C., with shaking at 250 rpm. The optical density ($OD_{600}$) of the overnight culture was measured, and the culture was diluted to an $OD_{600}$=0.1 in 250 mL of the same medium in a 1.0 L shake flask, and grown at 30° C. with shaking at 250 rpm to an $OD_{600}$ of between 0.8 to 1.0. The cells were then harvested by centrifugation at 2000×g for 10 min, and resuspended in 20 mL of 50 mM Tris-HCl buffer, pH 8.5. Enzyme assays were performed as described above.

Construction of plasmid pNY102 for thlA and hbd co-expression. A number of dual expression vectors were constructed for the co-expression of thlA and hbd genes. The *Saccharomyces cerevisiae* ERG10 gene is a functional ortholog of the thlA gene. Initially, a dual vector of ERG10 and hbd was constructed using the yeast GAL1-GAL10 divergent dual promoter, the GAL1 terminator (GAL1t) and the ERG10 terminator (ERG10t). The ERG10 gene-ERG10t DNA fragment was PCR amplified from genomic DNA of *Saccharomyces cerevisiae* strain BY4743, using primers OT731 (SEQ ID NO:164) and OT732 (SEQ ID NO:165). The yeast GAL1-GAL10 divergent promoter was also amplified by PCR from BY4743 genomic DNA using primers OT733 (SEQ ID NO:166) and OT734 (SEQ ID NO:167). The hbd gene was amplified from *E. coli* plasmid pTrc99a-E-C-H-T (described in Example 17) using PCR primers OT735 (SEQ ID NO:168) and OT736 (SEQ ID NO:169). GAL1t was amplified from BY4743 genomic DNA using primers OT737 (SEQ ID NO:170) and OT738 (SEQ ID NO:171). Four PCR fragments, erg10-ERG10t, GAL1-GAL10 promoters, hbd, and GAL1t, were thus obtained with approximately 25 bp overlapping sequences between each adjacent PCR fragment. GAL1t and ERG10-ERG10t fragments each contain approximately 25 bp overlapping sequences with the yeast vector pRS425. To assemble these sequences by gap repair recombination, the DNA fragments were co-transformed into the yeast strain BY4741 together with vector pRS425 which was digested with BamHI and HindIII enzymes. Colonies were selected from SD-Leu minimal plates, and clones with inserts were identified by PCR amplification. The new plasmid was named pNY6 (pRS425.ERG10t-erg10-GAL10-GAL1-hbd-GAL1t). Further confirmation was performed by restriction mapping.

The yeast strain BY4741 (pNY6), prepared by transforming plasmid pNY6 into *S. cerevisiae* BY4741, showed good Hbd activity but no thiolase activity. Due to the lack of thiolase activity, the ERG10 gene was replaced with the thlA gene by gap repair recombination. The thlA gene was amplified from *E. coli* vector pTrc99a-E-C-H-T by PCR using primers OT797 (SEQ ID NO:172) which adds a SphI restriction site, and OT798 (SEQ ID NO:173) which adds an AscI restriction site. Plasmid pNY6 was digested with SphI and PstI restriction enzymes, gel-purified, and co-transformed into yeast BY4741 along with the PCR product of thlA. Due to the 30 bp overlapping sequences between the PCR product of thlA and the digested pNY6, the thlA gene was recombined into pNY6 between the GAL10 promoter and the ERG10t terminator. This yielded plasmid pNY7 (pRS425.ERG10t-thlA-GAL10-GAL1-hbd-GAL1t), which was verified by PCR and restriction mapping.

In a subsequent cloning step based on gap repair recombination, the GAL10 promoter in pNY7 was replaced with the CUP1 promoter, and the GAL1 promoter was replaced with the strong GPD promoter. This plasmid, pNY10 (pRS425. ERG10t-thlA-CUP1-GPD-hbd-GAL1t) allows for the expression of the thlA gene under CUP1, a copper inducible promoter, and the expression of the hbd gene under the GPD promoter. The CUP1 promoter sequence was PCR amplified from yeast BY4743 genomic DNA using primers OT806 (SEQ ID NO:174), and OT807 (SEQ ID NO:175). The GPD promoter was amplified from BY4743 genomic DNA using primers OT808 (SEQ ID NO:176) and OT809 (SEQ ID NO:177). PCR products of the CUP1 and the GPD promoters were combined with pNY7 plasmid digested with NcoI and SphI restriction enzymes. From this gap repair cloning step, plasmid pNY10 was constructed, which was verified by PCR and restriction mapping. Yeast BY4741 strain containing pNY10 had Hbd activity, but no ThlA activity. The Hbd activity under GPD promoter was significantly improved compared to the GAL1 promoter controlled Hbd activity (1.8 U/mg vs. 0.40 U/mg). Sequencing analysis revealed that the thlA gene in pNY10 had a one base deletion near the 3' end, which resulted in a truncated protein. This explains the lack of thiolase activity in the strain.

Plasmid pNY12 was constructed with the correct thlA gene sequence. The thlA gene was cut from the vector pTrc99a-E-C-H-T by digestion with SphI and AscI. The FBA1 promoter was PCR amplified from BY4743 genomic DNA using primers OT799 (SEQ ID NO:178) and OT761 (SEQ ID NO:179), and digested with SalI and SphI restriction enzymes. The thlA gene fragment and FBA1 promoter fragment were ligated into plasmid pNY10 at AscI and SalI sites, generating plasmid pNY12 (pRS425.ERG10t-thlA-FBA1), which was confirmed by restriction mapping. pNY12 was transformed into yeast strain BY4741 and the resulting transformant showed a ThlA activity of 1.66 U/mg.

The FBA1 promoter-thlA gene fragment from pNY12 was re-subcloned into pNY10. The pNY10 vector was cut with the AscI restriction enzyme and ligated with the AscI digested FBA1 promoter-thlA gene fragment isolated from plasmid pNY12. This created a new plasmid with two possible insert orientations. The clones with FBA1 and GPD promoters located adjacent to each other in opposite orientation were chosen and this plasmid was named pNY102. pNY102 (pRS425. ERG10t-thlA-FBA1-GPD-hbd-GAL1t) was verified by restriction mapping. Strain DPD5206 was made by transforming pNY102 into yeast strain BY4741. The ThlA activity of DPD5206 was 1.24 U/mg and the Hbd activity was 0.76 U/mg.

Construction of plasmid pNY11 for crt expression. The crt gene expression cassette was constructed by combining the GPM1 promoter, the crt gene, and the GPM1t terminator into vector pRS426 using gap repair recombination in yeast. The GPM1 promoter was PCR amplified from yeast BY4743 genomic DNA using primers OT803 (SEQ ID NO:180) and OT804 (SEQ ID NO:181). The crt gene was amplified using PCR primers OT785 (SEQ ID NO:182) and OT786 (SEQ ID NO:183) from *E. Coli* plasmid pTrc99a-E-C-H-T. The GPM1t terminator was PCR amplified from yeast BY4743 genomic DNA using OT787 (SEQ ID NO:184) and OT805 (SEQ ID NO:185). Yeast vector pRS426 was digested with BamHI and HindIII and was gel-purified. This DNA was co-transformed with the PCR products of the GPM1 promoter, the crt gene and the GPM1 terminator into yeast BY4741 competent cells. Clones with the correct inserts were verified by PCR and restriction mapping and the resulting yeast strain BY4741 (pNY11: pRS426-GPM1-crt-GPM1t) had a Crt activity of 85 U/mg.

Construction of plasmid pNY103 for thlA, hbd and crt co-expression. For the co-expression of the upper 1-butanol pathway enzymes, the crt gene cassette from pNY11 was subcloned into plasmid pNY102 to create an hbd, thlA, and crt expression vector. A 2,347 bp DNA fragment containing the GPM1 promoter, the crt gene, and the GPM1 terminator was cut from plasmid pNY11 with SacI and NotI restriction enzymes and cloned into vector pNY102, which was digested with NotI and partially digested with SacI, producing the expression vector pNY103 (pRS425. ERG10t-thlA-FBA1-GPD-hbd-GAL1t-GPM1 t-crt-GPM1). Following confirmation of the presence of all three cassettes in pNY103 by digestion with HindIII, the plasmid was transformed into yeast BY4743 cells and the transformed yeast strain was named DPD5200. When grown under standard conditions, DPD5200 showed ThlA, Hbd, and Crt enzyme activities of 0.49 U/mg, 0.21 U/mg and 23.0 U/mg, respectively.

Construction of plasmid pNY8 for ald expression. A codon optimized gene named tery (SEQ ID NO:186), encoding the Ter protein (SEQ ID NO:187), and a codon optimized gene named aldy (SEQ ID NO:188), encoding the Ald protein (SEQ ID NO:189) were synthesized using preferred codons of *Saccharomyces cerevisiae*. Plasmid pTERy containing the codon optimized ter gene and pALDy containing the codon optimized ald gene were made by DNA2.0 (Palo Alto, Calif.).

To assemble pNY8 (pRS426.GPD-ald-GPDt), three insert fragments including a PCR product of the GPD promoter (synthesized from primers OT800 (SEQ ID NO:190) and OT758, (SEQ ID NO:191), and BY4743 genomic DNA), an aldy gene fragment excised from pALDy by digestion with NcoI and SfiI (SEQ ID NO:188), and a PCR product of the GPD terminator (synthesized from primers OT754 (SEQ ID NO:192) and OT755 (SEQ ID NO:193), and BY4743 genomic DNA) were recombined with the BamHI, HindIII digested pRS426 vector via gap repair recombination cloning. Yeast BY4741 transformation clones were analyzed by PCR mapping. The new plasmid thus constructed, pNY8, was further confirmed by restriction mapping. The yeast BY4741 transformants containing pNY8 were analyzed for Ald activity and the specific activity towards butyryl-CoA was approximately 0.07 U/mg.

Construction of plasmids pNY9 and pNY13 for ter expression. The codon optimized tery gene was cloned into vector pRS426 under control of the FBA1 promoter by gap repair cloning. The FBA1 promoter was PCR amplified from yeast BY4743 genomic DNA using primers OT760 (SEQ ID NO:194) and OT792 (SEQ ID NO:195). The tery gene was obtained by digestion of plasmid pTERy by SphI and NotI restriction enzymes that resulted in the fragment given as SEQ ID NO:186. The PCR fragment of FBA1 terminator was generated by PCR from yeast BY4743 genomic DNA using primers OT791 (SEQ ID NO:196) and OT765 (SEQ ID NO:197). Three DNA fragments, the FBA1 promoter, the ter gene and the FBA1 terminator, were combined with the BamHI, HindIII digested pRS426 vector and transformed into yeast BY4741 by gap repair recombination. The resulting plasmid, pNY9 (pRS426-FBA1-tery-FBA1t) was confirmed by PCR mapping, as well as restriction digestion. The yeast BY4741 transformant of pNY9 produced a Ter activity of 0.26 U/mg.

To make the final 1-butanol biosynthetic pathway strain, it was necessary to construct a yeast expression strain that contained several plasmids, each with a unique nutritional selection marker. Since the parent vector pRS426 contained a Ura selection marker, the ter expression cassette was subcloned into vector pRS423, which contained a His3 marker. A 3.2 kb fragment containing the FBA1-tery-FBA1t cassette was isolated from plasmid pNY9 by digestion with SacI and XhoI restriction enzymes, and ligated into vector pRS423 that was cut with these same two enzymes. The new plasmid, pNY13 (pRS423-FBA1-tery-FBA1t) was mapped by restriction digestion. pNY13 was transformed into BY4741 strain and the transformant was cultured in SD-His medium, yielding a strain with a Ter activity of 0.19 U/mg.

Construction of a yeast strain containing 1-butanol biosynthetic pathway genes for demonstration of 1-butanol production. As described above, yeast strain DPD5200 was constructed by transformation of plasmid pNY103 into *S. cerevisiae* strain BY4743, which allows co-expression of thlA, hbd and crt genes. Yeast competent cells of DPD5200 were prepared as described above, and plasmids pNY8 and pNY13 were co-transformed into DPD5200, generating strain DPD5213. DPD5213 allows for the simultaneous constitutive expression of five genes in the 1-butanol biosynthetic pathway, thlA, hbd, crt, ter and ald. Strain DPD5212 (*S. cerevisiae* strain BY4743 transformed with empty plasmids, pRS425 and pRS426) was used as a negative control. Four independent isolates of strain DPD5213 were grown on SD-Ura, -Leu, -His dropout minimal medium in the presence of either 2% glucose or 2% sucrose to allow the growth complementation of all three plasmids. A single isolate of DPD5212 was similarly grown in appropriate medium.

To demonstrate 1-butanol production by aerobic cultures, a single colony of each strain was streaked onto a fresh agar plate containing SD minimal drop out growth medium (containing 2% glucose) or SS minimal drop out growth medium (containing 2% sucrose) and incubated at 30° C. for 2 days. Cells from these plates were used to inoculate 20 mL of the minimal drop out medium (either SD or SS) in 125 mL plastic shake flasks and were grown overnight at 30° C. with shaking at 250 rpm. The optical density ($OD_{600}$) of the overnight culture was measured, the culture was diluted to $OD_{600}$ of 0.1 in 25 mL of the same medium in a 125 mL shake flask, and grown at 30° C. with shaking at 250 rpm.

Aliquots of the culture were removed at 24 h and 48 h for GC analysis of 1-butanol production (HP-INNOWax column, 30 m×0.53 mm id, 1 μm film thickness) with FID detection, as described in the General Methods section. The results of the GC analysis are given in Table 23.

TABLE 23

Production of 1-butanol from glucose and sucrose by *S. cerevisiae* strain DPD5213

| Strain[1] | Sugar | 1-butanol at 24 h, mg/L[2] | 1-butanol at 48 h, mg/L[2] |
|---|---|---|---|
| DPD5212 | Glucose | Not detected | Not detected |
| DPD5213 a | Glucose | 0.4 | 0.5 |
| DPD5213 b | Glucose | 0.9 | 0.2 |
| DPD5213 c | Glucose | 1.0 | 0.6 |

TABLE 23-continued

Production of 1-butanol from glucose and sucrose by *S. cerevisiae* strain DPD5213

| Strain[1] | Sugar | 1-butanol at 24 h, mg/L[2] | 1-butanol at 48 h, mg/L[2] |
|---|---|---|---|
| DPD5213 d | Glucose | 0.8 | 0.3 |
| DPD5212 | Sucrose | Not detected | Not detected |
| DPD5213 a | Sucrose | Not detected | 1.7 |
| DPD5213 b | Sucrose | Not detected | 1.3 |
| DPD5213 c | Sucrose | 0.2 | 1.5 |
| DPD5213 d | Sucrose | 0.6 | 0.9 |

[1]Independent isolates are indicated by a-d.

[2]Concentration determined by GC.

Example 22 (Prophetic)

Expression of the 1-Butanol Biosynthetic Pathway in *Lactobacillus plantarum*

The purpose of this prophetic Example is to describe how to express the 1-butanol biosynthetic pathway in *Lactobacillus plantarum*. The six genes of the 1-butanol pathway, encoding six enzyme activities, are divided into two operons for expression. The first three genes of the pathway (thl, hbd, and crt, encoding the enzymes acetyl-CoA acetyltransferase, 3-hydroxybutyryl-CoA dehydrogenase, and crotonase, respectively) are integrated into the chromosome of *Lactobacillus plantarum* by homologous recombination using the method described by Hols et al. (*Appl. Environ. Microbiol.* 60:1401-1413 (1994)). The last three genes (EgTER, ald, and bdhB, encoding the enzymes butyryl-CoA dehydrogenase, butyraldehyde dehydrogenase and butanol dehydrogenase, respectively) are cloned into an expression plasmid and transformed into the *Lactobacillus* strain carrying the integrated upper pathway 1-butanol genes. *Lactobacillus* is grown in MRS medium (Difco Laboratories, Detroit, Mich.) at 37° C. Chromosomal DNA is isolated from *Lactobacillus plantarum* as described by Moreira et al. (*BMC Microbiol.* 5:15 (2005)).

Integration. The thl-hbd-crt cassette under the control of the synthetic P11 promoter (Rud et al., *Microbiology* 152: 1011-1019 (2006)) is integrated into the chromosome of *Lactobacillus plantarum* ATCC BAA-793 (NCIMB 8826) at the ldhL1 locus by homologous recombination. To build the ldhL integration targeting vector, a DNA fragment from *Lactobacillus plantarum* (Genbank NC_004567) with homology to ldhL is PCR amplified with primers LDH EcoRV F (SEQ ID NO:198) and LDH AatIIR (SEQ ID NO:199). The 1986 bp PCR fragment is cloned into pCR4Blunt-TOPO and sequenced. The pCR4Blunt-TOPO-ldhL1 clone is digested with EcoRV and AatII releasing a 1982 bp ldhL1 fragment that is gel-purified. The integration vector pFP988, described in Example 18, is digested with HindIII and treated with Klenow DNA polymerase to blunt the ends. The linearized plasmid is then digested with AatII and the 2931 bp vector fragment is gel-purified. The EcoRV/AatII ldhL1 fragment is ligated with the pFP988 vector fragment and transformed into *E. coli* Top10 cells. Transformants are selected on LB agar plates containing ampicillin (100 μg/mL) and are screened by colony PCR to confirm construction of pFP988-ldhL.

To add a selectable marker to the integrating DNA, the Cm gene with its promoter is PCR amplified from pC194 (Genbank NC_002013) with primers Cm F (SEQ ID NO:200) and Cm R (SEQ ID NO:201), amplifying a 836 bp PCR product. The amplicon is cloned into pCR4Blunt-TOPO and transformed into *E. coli* Top10 cells, creating pCR4Blunt-TOPO-Cm. After sequencing to confirm that no errors are introduced by PCR, the Cm cassette is digested from pCR4Blunt-TOPO-Cm as an 828 bp MluI/SwaI fragment and is gel-purified. The ldhL-homology containing integration vector pFP988-ldhL is digested with MluI and SwaI and the 4740 bp vector fragment is gel-purified. The Cm cassette fragment is ligated with the pFP988-ldhL vector creating pFP988-DldhL::Cm.

Finally the thl-hbd-crt cassette from pFP988Dss-T-H-C, described in Example 18, is modified to replace the amylase promoter with the synthetic P11 promoter. Then, the whole operon is moved into pFP988-DldhL::Cm. The P11 promoter is built by oligonucleotide annealing with primer P11 F (SEQ ID NO:202) and P11 R (SEQ ID NO:203). The annealed oligonucleotide is gel-purified on a 6% Ultra PAGE gel (Embi Tec, San Diego, Calif.). The plasmid pFP988Dss-T-H-C is digested with XhoI and SmaI and the 9 kbp vector fragment is gel-purified. The isolated P11 fragment is ligated with the digested pFP988Dss-T-H-C to create pFP988-P11-T-H-C. Plasmid pFP988-P11-T-H-C is digested with XhoI and BamHI and the 3034 bp P11-T-H-C fragment is gel-purified. pFP988-DldhL::Cm is digested with XhoI and BamHI and the 5558 bp vector fragment isolated. The upper pathway operon is ligated with the integration vector to create pFP988-DldhL-P11-THC::Cm.

Integration of pFP988-DldhL-P11-THC::Cm into *L. plantarum* BAA-793 to form *L. plantarum* ΔldhL1::T-H-C::Cm comprising exogenous thl, hbd, and crt genes. Electrocompetent cells of *L. plantarum* are prepared as described by Aukrust, T. W., et al. (In: *Electroporation Protocols for Microorganisms*; Nickoloff, J. A., Ed.; *Methods in Molecular Biology*, Vol. 47; Humana Press, Inc., Totowa, N.J., 1995, pp 201-208). After electroporation, cells are outgrown in MRSSM medium (MRS medium supplemented with 0.5 M sucrose and 0.1 M $MgCl_2$) as described by Aukrust et al. supra for 2 h at 37° C. without shaking. Electroporated cells are plated for selection on MRS plates containing chloramphenicol (10 μg/mL) and incubated at 37° C. Transformants are initially screened by colony PCR amplification to confirm integration, and initial positive clones are then more rigorously screened by PCR amplification with a battery of primers.

Plasmid Expression of EgTER, ald, and bdhB genes. The three remaining 1-butanol genes are expressed from plasmid pTRKH3 (O'Sullivan D J and Klaenhammer T R, *Gene* 137: 227-231 (1993)) under the control of the *L. plantarum* ldhL promoter (Ferain et al., *J. Bacteriol.* 176:596-601 (1994)). The ldhL promoter is PCR amplified from the genome of *L. plantarum* ATCC BAA-793 with primers PldhL F (SEQ ID NO:204) and PldhL R (SEQ ID NO:205). The 369 bp PCR product is cloned into pCR4Blunt-TOPO and sequenced. The resulting plasmid, pCR4Blunt-TOPO-PldhL is digested with SacI and BamHI releasing the 359 bp PldhL fragment.

pHT01-ald-EB, described in Example 18, is digested with SacI and BamHI and the 10503 bp vector fragment is recovered by gel purification. The PldhL fragment and vector are ligated creating pHT01-Pldhl-ald-EB.

To subclone the ldhL promoter-ald-EgTER-bdh cassette, pHT01-Pldhl-ald-EB is digested with MluI and the ends are treated with Klenow DNA polymerase. The linearized vector is digested with SalI and the 4270 bp fragment containing the PldhL-AEB fragment is gel-purified. Plasmid pTRKH3 is digested with SalI and EcoRV and the gel-purified vector fragment is ligated with the PldhL-AEB fragment. The ligation mixture is transformed into *E. coli* Top 10 cells and transformants are plated on Brain Heart Infusion (BHI, Difco Laboratories, Detroit, Mich.) plates containing erythromycin (150 mg/L). Transformants are screened by PCR to confirm construction of pTRKH3-ald-E-B. The expression plasmid, pTRKH3-ald-E-B is transformed into *L. plantarum* ΔldhL1::T-H-C::Cm by electroporation, as described above.

*L. plantarum* ΔldhL1::T-H-C::Cm containing pTRKH3-ald-E-B is inoculated into a 250 mL shake flask containing 50 mL of MRS medium plus erythromycin (10 μg/mL) and grown at 37° C. for 18 to 24 h without shaking. After 18 h to 24, 1-butanol is detected by HPLC or GC analysis, as described in the General Methods section.

Example 23 (Prophetic)

Expression of the 1-Butanol Biosynthetic Pathway in *Enterococcus faecalis*

The purpose of this prophetic Example is to describe how to express the 1-butanol biosynthetic pathway in *Enterococcus faecalis*. The complete genome sequence of *Enterococcus faecalis* strain V583, which is used as the host strain for the expression of the 1-butanol biosynthetic pathway in this Example, has been published (Paulsen et al., *Science* 299: 2071-2074 (2003)). Plasmid pTRKH3 (O'Sullivan D J and Klaenhammer T R, *Gene* 137:227-231 (1993)), an *E. coli*/Gram-positive shuttle vector, is used for expression of the six genes (thlA, hbd, crt, EgTER, ald, bdhB) of the 1-butanol pathway in one operon. pTRKH3 contains an *E. coli* plasmid p15A replication origin and the pAMβ1 replicon, and two antibiotic resistance selection markers, tetracycline resistance and erythromycin resistance. Tetracycline resistance is only expressed in *E. coli*, and erythromycin resistance is expressed in both *E. coli* and Gram-positive bacteria. Plasmid pAMβ1 derivatives can replicate in *E. faecalis* (Poyart et al., *FEMS Microbiol. Lett.* 156:193-198 (1997)). The inducible nisA promoter (PnisA), which has been used for efficient control of gene expression by nisin in a variety of Gram-positive bacteria including *Enterococcus faecalis* (Eichenbaum et al., *Appl. Environ. Microbiol.* 64:2763-2769 (1998)), is used to control expression of the six desired genes encoding the enzymes of the 1-butanol biosynthetic pathway.

The linear DNA fragment (215 bp) containing the nisA promoter (Chandrapati et al., *Mol. Microbiol.* 46(2):467-477 (2002)) is PCR-amplified from *Lactococcus* lactis genomic DNA with primers F-PnisA(EcoRV) (SEQ ID NO:206) and R-PnisA(PmeI BamHI) (SEQ ID NO:207). The 215 bp PCR fragment is digested with EcoRV and BamHI, and the resulting PnisA fragment is gel-purified. Plasmid pTRKH3 is digested with EcoRV and BamHI and the vector fragment is gel-purified. The linearised pTRKH3 is ligated with the PnisA fragment. The ligation mixture is transformed into *E. coli* Top10 cells by electroporation and transformants are selected following overnight growth at 37° C. on LB agar plates containing erythromycin (25 μg/mL). The transformants are then screened by colony PCR with primers F-PnisA (EcoRV) and R-PnisA(BamHI) to confirm the correct clone of pTRKH3-PnisA.

Plasmid pTRKH3-PnisA is digested with PmeI and BamHI, and the vector is gel-purified. Plasmid pHT01-ald-EgTER-bdhB is constructed as described in Example 18 and is digested with SmaI and BamHI, and the 2,973 bp ald-EgTER-bdhB fragment is gel-purified. The 2,973 bp ald-EgTER-bdhB fragment is ligated into the pTRKH3-PnisA vector at the PmeI and BamHI sites. The ligation mixture is transformed into *E. coli* Top10 cells by electroporation and transformants are selected following incubation at 37° C. overnight on LB agar plates containing erythromycin (25 μg/mL). The transformants are then screened by colony PCR with primers ald forward primer N27F1 (SEQ ID NO: 31) and bdhB reverse primer N65 (SEQ ID NO: 44). The resulting plasmid is named pTRKH3-PnisA-ald-EgTER-bdhB (=pTRKH3-A-E-B).

Plasmid pTRKH3-A-E-B is purified from the transformant and used for further cloning of the remaining genes (thlA, hbd, crt) into the BamHI site located downstream of the bdhB gene. Plasmid pTRKH3-A-E-B is digested with BamHI and treated with the Klenow fragment of DNA polymerase to make blunt ends. Plasmid pFP988Dss-thlA-hbd-crt (=pFP988Dss-T-H-C) is constructed as described in Example 18 and is digested with SmaI and BamHI. The resulting 2,973 bp thlA-hbd-crt fragment is treated with the Klenow fragment of DNA polymerase to make blunt ends and is gel-purified. The 2,973 bp thlA-hbd-crt fragment is ligated with the linearised pTRKH3-A-E-B. The ligation mixture is transformed into *E. coli* Top10 cells by electroporation and transformants are selected following overnight growth at 37° C. on LB agar plates containing erythromycin (25 μg/mL). The transformants are then screened by colony PCR with primers thlA forward primer N7 (SEQ ID NO: 21) and crt reverse primer N4 (SEQ ID NO: 18). The resulting plasmid is named pTRKH3-PnisA-ald-EgTER-bdhB-thlA-hbd-crt (=pTRKH3-A-E-B-T-H-C). Plasmid pTRKH3-A-E-B-T-H-C is prepared from the *E. coli* transformants and transformed into electro-competent *E. faecalis* V583 cells by electroporation using methods known in the art (Aukrust, T. W., et al. In: *Electroporation Protocols for Microorganisms*; Nickoloff, J. A., Ed.; *Methods in Molecular Biology*, Vol. 47; Humana Press, Inc., Totowa, N.J., 1995, pp 217-226), resulting in *E. faecalis* V583/pTRKH3-A-E-B-T-H-C.

The second plasmid containing nisA regulatory genes, nisR and nisK, the add9 spectinomycin resistance gene, and the pSH71 origin of replication is transformed into *E. faecalis* V583/pTRKH3-A-E-B-T-H-C by electroporation. The plasmid containing pSH71 origin of replication is compatible with pAMβ1 derivatives in *E. faecalis* (Eichenbaum et al., supra). Double drug resistant transformants are selected on LB agar plates containing erythromycin (25 μg/mL) and spectinomycin (100 μg/mL).

The resulting *E. faecalis* strain V583B harboring two plasmids, i.e., an expression plasmid (pTRKH3-A-E-B-T-H-C) and a regulatory plasmid (pSH71-nisRK), is inoculated into a 250 mL shake flask containing 50 mL of Todd-Hewitt broth supplemented with yeast extract (0.2%) (Fischetti et al., *J. Exp. Med.* 161:1384-1401 (1985)), nisin (20 μg/mL) (Eichenbaum et al., supra), erythromycin (25 μg/mL), and spectinomycin (100 μg/mL). The flask is incubated without shaking at 37° C. for 18 to 24 h, after which time, 1-butanol production is measured by HPLC or GC analysis, as described in the General Methods section.

Example 24

Increased Tolerance of *Saccharomyces cerevisiae* to 1-Butanol at Decreased Growth Temperatures Tolerance levels were determined for yeast strain *Saccharomyces cerevisiae* BY4741 (described in Example 21) at 25° C. and 30° C. as follows. The strain was cultured in YPD medium. Overnight cultures in the absence of any test compound were started in 25 mL of YPD medium in 150 mL flasks with incubation at 30° C. or at 25° C. in shaking water baths. The next morning, each overnight culture was diluted into a 500 mL flask-containing 300 mL of fresh medium to an initial $OD_{600}$ of about 0.1. The flasks were incubated in shaking water baths at 30° C. or 25° C., using the same temperature as used for each overnight culture. The large cultures were incubated for 3 hours and then were split into flasks in the absence (control) and in the presence of 1% or 2% of 1-butanol. Growth was followed by measuring $OD_{600}$ for six hours after addition of the 1-butanol. The $\Delta OD_{600}$ was calculated by subtracting the initial $OD_{600}$ from the final $OD_{600}$ at 6 hours. The percent growth inhibition relative to the control culture was calculated as follows: % Growth Inhibition=100−[100(Sample $\Delta OD_{600}$/Control $\Delta OD_{600}$)]. The results are summarized in Table 24 below and indicate that growth of strain BY4741 was less inhibited by 1% 1-butanol at 25° C. than by 1% 1-butanol at 30° C.

TABLE 24

Growth of *Saccharomyces cerevisiae* Strain BY4741 at 25° C. and 30° C. with 1-Butanol.

| % 1-Butanol | Temperature ° C. | % Growth Inhibition |
|---|---|---|
| 1 | 30 | 64 |
| 1 | 25 | 43 |
| 2 | 30 | No growth |
| 2 | 25 | No growth |

What is claimed is:

1. A method for the production of 1-butanol comprising:

a) providing a recombinant microbial production host cell which is tolerant to 1-butanol, and wherein the recombinant microbial host cell comprises heterologous DNA molecules encoding polypeptides that catalyze each of the following substrate to product conversions:
   i) acetyl-CoA to acetoacetyl-CoA;
   ii) acetoacetyl-CoA to 3-hydroxybutyryl-CoA;
   iii) 3-hydroxybutyryl-CoA to crotonyl-CoA;
   iv) crotonyl-CoA to butyryl-CoA;
   v) butyryl-CoA to butyraldehyde; and
   vi) butyraldehyde to 1-butanol;

b) seeding the production host of (a) into a fermentation medium comprising at least one fermentable carbon substrate to create a fermentation culture;

c) growing the production host in the fermentation culture at a first temperature for a first period of time determined by a change in at least one monitored metabolic parameter of the fermentation culture;

d) lowering the temperature of the fermentation culture to a second temperature for a second period of time determined by a change in at least one monitored metabolic parameter of the fermentation culture;

e) optionally lowering the temperature of the fermentation culture to a third temperature for a third period of time determined by a change in at least one monitored metabolic parameter of the fermentation culture;

wherein steps (c), (d) and (e) are optionally repeated to maintain a desired rate of 1-butanol production.

2. The method according to claim 1, wherein the fermentable carbon substrate is derived from a grain or sugar source selected from the group consisting of wheat, corn, barley, oats, rye, sugar cane, sugar beets, cassava, sweet sorghum, and mixtures thereof.

3. The method according to claim 1, wherein the fermentable carbon substrate is derived from cellulosic or lignocellulosic biomass selected from the group consisting of corn cobs, crop residues, corn husks, corn stover, grasses, wheat straw, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

4. The method according to claim 1, wherein the fermentable carbon substrate is selected from the group consisting of monosaccharides, oligosaccharides, and polysaccharides.

5. The method according to claim 1, wherein the fermentation culture is maintained under anaerobic or microaerobic conditions to maintain a desired rate of 1-butanol production.

6. The method according to claim 1, wherein the metabolic parameter that is monitored is selected from the group consisting of optical density, pH, respiratory quotient, fermentable carbon substrate utilization, $CO_2$ production, and 1-butanol production.

7. The method according to claim 1, wherein lowering the temperature of the fermentation culture occurs at a predetermined time.

8. The method according to claim 1, wherein the first temperature is from about 25° C. to about 40° C.; and the second temperature is from about 3° C. to about 25° C. lower than the first temperature.

9. The method according to claim 1, wherein the recombinant microbial production host is selected from the group consisting of *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Saccharomyces*, and *Pichia*, and wherein the concentration of 1-butanol that is responsible for 50% inhibition of the growth rate of the microbial production host in a minimal medium is greater than about 0.5% weight/volume.

10. The method according to claim 1, wherein the polypeptide that catalyzes the substrate to product conversion of acetyl-CoA to acetoacetyl-CoA is acetyl-CoA acetyltransferase; the polypeptide that catalyzes the substrate to product conversion of acetoacetyl-CoA to 3-hydroxybutyryl-CoA is 3-hydroxybutyryl-CoA dehydrogenase; the polypeptide that catalyzes the substrate to product conversion of 3-hydroxybutyryl-CoA to crotonyl-CoA is crotonase; the polypeptide that catalyzes the substrate to product conversion of crotonyl-CoA to butyryl-CoA is butyryl-CoA dehydrogenase; the polypeptide that catalyzes the substrate to product conversion of butyryl-CoA to butyraldehyde is butyraldehyde dehydrogenase; and the polypeptide that catalyzes the substrate to product conversion of butyraldehyde to 1-butanol is butanol dehydrogenase.

11. The method according to claim 10, wherein the acetyl-CoA acetyltransferase has an amino acid sequence having at least 95% identity to an amino acid sequence selected from the group consisting of SEQ ID NO:2, SEQ ID NO:4, SEQ ID NO:129, SEQ ID NO:131, and SEQ ID NO:133 based on the Clustal W method of alignment using the default parameters of GAP PENALTY=10, GAP LENGTH PENALTY=0.1, and Gonnet 250 series of protein weight matrix.

12. The method according to claim 10, wherein the 3-hydroxybutyryl-CoA dehydrogenase has an amino acid sequence having at least 95% identity to an amino acid sequence selected from the group consisting of SEQ ID NO:6, SEQ ID NO:135, SEQ ID NO:137, and SEQ ID NO:139 based on the Clustal W method of alignment using the default parameters of GAP PENALTY=10, GAP LENGTH PENALTY=0.1, and Gonnet 250 series of protein weight matrix.

13. The method according to claim 10, wherein the crotonase has an amino acid sequence having at least 95% identity to an amino acid sequence selected from the group consisting of SEQ ID NO:8, SEQ ID NO:141, SEQ ID NO:143, and SEQ ID NO:145 based on the Clustal W method of alignment using the default parameters of GAP PENALTY=10, GAP LENGTH PENALTY=0.1, and Gonnet 250 series of protein weight matrix.

14. The method according to claim 10, wherein the butyryl-CoA dehydrogenase has an amino acid sequence having at least 95% identity to an amino acid sequence selected from the group consisting of SEQ ID NO:10, SEQ ID NO:147, SEQ ID NO:149, SEQ ID NO:151, and SEQ ID NO:187 based on the Clustal W method of alignment using the default parameters of GAP PENALTY=10, GAP LENGTH PENALTY=0.1, and Gonnet 250 series of protein weight matrix.

15. The method according to claim 10, wherein the butyraldehyde dehydrogenase has an amino acid sequence having at least 95% identity to an amino acid sequence selected from the group consisting of SEQ ID NO:12, SEQ ID NO:153, and SEQ ID NO:189 based on the Clustal W method of alignment using the default parameters of GAP PENALTY=10, GAP LENGTH PENALTY=0.1, and Gonnet 250 series of protein weight matrix.

16. The method according to claim 10, wherein the butanol dehydrogenase has an amino acid sequence having at least 95% identity to an amino acid sequence selected from the group consisting of SEQ ID NO:14, SEQ ID NO:16, SEQ ID NO:153, SEQ ID NO:155, and SEQ ID NO:157 based on the Clustal W method of alignment using the default parameters of GAP PENALTY=10, GAP LENGTH PENALTY=0.1, and Gonnet 250 series of protein weight matrix.

17. The method of claim 1, wherein the at least one monitored metabolic parameter of the fermentation culture is adjusted to maintain a desired rate of 1-butanol production.

18. The method of claim 1, wherein the temperature is lowered gradually or lowered in a stepwise manner.

19. The method of claim 1, wherein the production of 1-butanol is practiced in a batch or fed-batch system.

20. The method of claim 1, wherein the production of 1-butanol is practiced in a continuous system.

21. The method of claim 19 or 20, wherein the microbial production host is immobilized.

* * * * *

SEQUENCE LISTING

```
<160> NUMBER OF SEQ ID NOS: 208

<210> SEQ ID NO 1
<211> LENGTH: 1179
<212> TYPE: DNA
<213> ORGANISM: Clostridium acetobutylicum

<400> SEQUENCE: 1

atgaaagaag ttgtaatagc tagtgcagta agaacagcga ttggatctta tggaaagtct      60

cttaaggatg taccagcagt agatttagga gctacagcta taaaggaagc agttaaaaaa     120

gcaggaataa aaccagagga tgttaatgaa gtcattttag gaaatgttct tcaagcaggt     180

ttaggacaga atccagcaag acaggcatct tttaaagcag gattaccagt tgaaattcca     240

gctatgacta ttaataaggt ttgtggttca ggacttagaa cagttagctt agcagcacaa     300

attataaaag caggagatgc tgacgtaata atagcaggtg gtatggaaaa tatgtctaga     360

gctccttact tagcgaataa cgctagatgg ggatatagaa tgggaaacgc taaatttgtt     420

gatgaaatga tcactgacgg attgtgggat gcatttaatg attaccacat gggaataaca     480

gcagaaaaca tagctgagag atggaacatt tcaagagaag aacaagatga gtttgctctt     540

gcatcacaaa aaaaagctga agaagctata aaatcaggtc aatttaaaga tgaaatagtt     600

cctgtagtaa ttaaaggcag aaagggagaa actgtagttg atacagatga gcaccctaga     660

tttggatcaa ctatagaagg acttgcaaaa ttaaaacctg ccttcaaaaa agatggaaca     720

gttacagctg gtaatgcatc aggattaaat gactgtgcag cagtacttgt aatcatgagt     780

gcagaaaaag ctaaagagct tggagtaaaa ccacttgcta agatagtttc ttatggttca     840

gcaggagttg acccagcaat aatgggatat ggacctttct atgcaacaaa agcagctatt     900

gaaaaagcag gttggacagt tgatgaatta gatttaatag aatcaaatga agcttttgca     960

gctcaaagtt tagcagtagc aaaagattta aaatttgata tgaataaagt aaatgtaaat    1020

ggaggagcta ttgcccttgg tcatccaatt ggagcatcag gtgcaagaat actcgttact    1080

cttgtacacg caatgcaaaa aagagatgca aaaaaaggct tagcaacttt atgtataggt    1140

ggcggacaag gaacagcaat attgctagaa aagtgctag                            1179


<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
1               5                   10                  15
```

```
Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390
```

<210> SEQ ID NO 3
<211> LENGTH: 1179
<212> TYPE: DNA
<213> ORGANISM: Clostridium acetobutylicum

<400> SEQUENCE: 3

```
atgagagatg tagtaatagt aagtgctgta agaactgcaa taggagcata tggaaaaaca     60

ttaaaggatg tacctgcaac agagttagga gctatagtaa taaaggaagc tgtaagaaga    120

gctaatataa atccaaatga gattaatgaa gttatttttg gaaatgtact tcaagctgga    180

ttaggccaaa acccagcaag acaagcagca gtaaaagcag gattaccttt agaaacacct    240

gcgtttacaa tcaataaggt ttgtggttca ggtttaagat ctataagttt agcagctcaa    300

attataaaag ctggagatgc tgataccatt gtagtaggtg gtatggaaaa tatgtctaga    360

tcaccatatt tgattaacaa tcagagatgg ggtcaaagaa tgggagatag tgaattagtt    420

gatgaaatga taaaggatgg tttgtgggat gcatttaatg gatatcatat gggagtaact    480

gcagaaaata ttgcagaaca atggaatata acaagagaag agcaagatga attttcactt    540

atgtcacaac aaaaagctga aaaagccatt aaaaatggag aatttaagga tgaaatagtt    600

cctgtattaa taaagactaa aaaaggtgaa atagtctttg atcaagatga atttcctaga    660

ttcggaaaca ctattgaagc attaagaaaa cttaaaccta ttttcaagga aaatggtact    720

gttacagcag gtaatgcatc cggattaaat gatggagctg cagcactagt aataatgagc    780

gctgataaag ctaacgctct cggaataaaa ccacttgcta agattacttc ttacggatca    840

tatggggtag atccatcaat aatgggatat ggagcttttt atgcaactaa agctgcctta    900

gataaaatta atttaaaacc tgaagactta gatttaattg aagctaacga ggcatatgct    960

tctcaaagta tagcagtaac tagagattta aatttagata tgagtaaagt taatgttaat   1020

ggtggagcta tagcacttgg acatccaata ggtgcatctg gtgcacgtat tttagtaaca   1080

ttactatacg ctatgcaaaa aagagattca aaaaaaggtc ttgctactct atgtattggt   1140

ggaggtcagg gaacagctct cgtagttgaa agagactaa                          1179
```

<210> SEQ ID NO 4
<211> LENGTH: 392
<212> TYPE: PRT
<213> ORGANISM: Clostridium acetobutylicum

<400> SEQUENCE: 4

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
    130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175
```

```
Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

Asp Ser Lys Lys Gly Leu Ala Thr Leu Cys Ile Gly Gly Gly Gln Gly
    370                 375                 380

Thr Ala Leu Val Val Glu Arg Asp
385                 390
```

<210> SEQ ID NO 5
<211> LENGTH: 849
<212> TYPE: DNA
<213> ORGANISM: Clostridium acetobutylicum

<400> SEQUENCE: 5

```
atgaaaaagg tatgtgttat aggtgcaggt actatgggtt caggaattgc tcaggcattt     60

gcagctaaag gatttgaagt agtattaaga gatattaaag atgaatttgt tgatagagga    120

ttagatttta tcaataaaaa tctttctaaa ttagttaaaa aaggaaagat agaagaagct    180

actaaagttg aaatcttaac tagaatttcc ggaacagttg accttaatat ggcagctgat    240

tgcgatttag ttatagaagc agctgttgaa agaatggata ttaaaaagca gatttttgct    300

gacttagaca atatatgcaa gccagaaaca attcttgcat caaatacatc atcactttca    360

ataacagaag tggcatcagc aactaaaaga cctgataagg ttataggtat gcatttcttt    420

aatccagctc ctgttatgaa gcttgtagag gtaataagag gaatagctac atcacaagaa    480

acttttgatg cagttaaaga gacatctata gcaataggaa aagatcctgt agaagtagca    540

gaagcaccag gatttgttgt aaatagaata ttaataccaa tgattaatga agcagttggt    600

atattagcag aaggaatagc ttcagtagaa gacatagata aagctatgaa acttggagct    660

aatcacccaa tgggaccatt agaattaggt gattttatag gtcttgatat atgtcttgct    720

ataatggatg ttttatactc agaaactgga gattctaagt atagaccaca tacattactt    780

aagaagtatg taagagcagg atggcttgga agaaaatcag gaaaaggttt ctacgattat    840

tcaaaataa                                                            849
```

<210> SEQ ID NO 6
<211> LENGTH: 282
<212> TYPE: PRT
<213> ORGANISM: Clostridium acetobutylicum

<400> SEQUENCE: 6

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280

<210> SEQ ID NO 7
<211> LENGTH: 786
<212> TYPE: DNA
<213> ORGANISM: Clostridium acetobutylicum

<400> SEQUENCE: 7
atggaactaa acaatgtcat ccttgaaaag gaaggtaaag ttgctgtagt taccattaac 60
agacctaaag cattaaatgc gttaaatagt gatacactaa aagaaatgga ttatgttata 120
ggtgaaattg aaaatgatag cgaagtactt gcagtaattt taactggagc aggagaaaaa 180
tcatttgtag caggagcaga tatttctgag atgaaggaaa tgaataccat tgaaggtaga 240
aaattcggga tacttggaaa taaagtgttt agaagattag aacttcttga aaagcctgta 300

```
atagcagctg ttaatggttt tgctttagga ggcggatgcg aaatagctat gtcttgtgat    360

ataagaatag cttcaagcaa cgcaagattt ggtcaaccag aagtaggtct cggaataaca    420

cctggttttg gtggtacaca aagactttca agattagttg gaatgggcat ggcaaagcag    480

cttatattta ctgcacaaaa tataaaggca gatgaagcat taagaatcgg acttgtaaat    540

aaggtagtag aacctagtga attaatgaat acagcaaaag aaattgcaaa caaaattgtg    600

agcaatgctc cagtagctgt taagttaagc aaacaggcta ttaatagagg aatgcagtgt    660

gatattgata ctgctttagc atttgaatca gaagcatttg gagaatgctt ttcaacagag    720

gatcaaaagg atgcaatgac agctttcata gagaaaagaa aaattgaagg cttcaaaaat    780

agatag                                                               786
```

```
<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 9
```

<211> LENGTH: 1197
<212> TYPE: DNA
<213> ORGANISM: Clostridium acetobutylicum

<400> SEQUENCE: 9

```
atgatagtaa aagcaaagtt tgtaaaagga tttatcagag atgtacatcc ttatggttgc     60

agaagggaag tactaaatca aatagattat tgtaagaagg ctattgggtt taggggacca    120

aagaaggttt taattgttgg agcctcatct gggtttggtc ttgctactag aatttcagtt    180

gcatttggag gtccagaagc tcacacaatt ggagtatcct atgaaacagg agctacagat    240

agaagaatag gaacagcggg atggtataat aacatatttt ttaaagaatt tgctaaaaaa    300

aaaggattag ttgcaaaaaa cttcattgag gatgcctttt ctaatgaaac caaagataaa    360

gttattaagt atataaagga tgaatttggt aaaatagatt tatttgttta tagtttagct    420

gcgcctagga gaaaggacta taaaactgga aatgtttata cttcaagaat aaaaacaatt    480

ttaggagatt ttgagggacc gactattgat gttgaaagag acgagattac tttaaaaaag    540

gttagtagtg ctagcattga agaaattgaa gaaactagaa aggtaatggg tggagaggat    600

tggcaagagt ggtgtgaaga gctgctttat gaagattgtt tttcggataa agcaactacc    660

atagcatact cgtatatagg atccccaaga acctacaaga tatatagaga aggtactata    720

ggaatagcta aaaaggatct tgaagataag gctaagctta taaatgaaaa acttaacaga    780

gttataggtg gtagagcctt tgtgtctgtg aataaagcat tagttacaaa agcaagtgca    840

tatattccaa cttttcctct ttatgcagct attttatata aggtcatgaa agaaaaaaat    900

attcatgaaa attgtattat gcaaattgag agaatgtttt ctgaaaaaat atattcaaat    960

gaaaaaatac aatttgatga caagggaaga ttaaggatgg acgatttaga gcttagaaaa   1020

gacgttcaag acgaagttga tagaatatgg agtaatatta ctcctgaaaa ttttaaggaa   1080

ttatctgatt ataagggata caaaaaagaa ttcatgaact taaacggttt tgatctagat   1140

ggggttgatt atagtaaaga cctggatata gaattattaa gaaaattaga accttaa      1197
```

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140
```

```
Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395
```

<210> SEQ ID NO 11
<211> LENGTH: 1407
<212> TYPE: DNA
<213> ORGANISM: Clostridium beijerinckii

<400> SEQUENCE: 11

```
atgaataaag acacactaat acctacaact aaagatttaa aagtaaaaac aaatggtgaa      60

aacattaatt taaagaacta caaggataat tcttcatgtt tcggagtatt cgaaaatgtt     120

gaaaatgcta taagcagcgc tgtacacgca caaaagatat tatcccttca ttatacaaaa     180

gagcaaagag aaaaaatcat aactgagata agaaaggccg cattacaaaa taaagaggtc     240

ttggctacaa tgattctaga agaaacacat atgggaagat atgaggataa aatattaaaa     300

catgaattgg tagctaaata tactcctggt acagaagatt taactactac tgcttggtca     360

ggtgataatg gtcttacagt tgtagaaatg tctccatatg gtgttatagg tgcaataact     420

ccttctacga atccaactga aactgtaata tgtaatagca taggcatgat agctgctgga     480

aatgctgtag tatttaacgg acacccatgc gctaaaaaat gtgttgcctt tgctgttgaa     540

atgataaata aggcaattat ttcatgtggc ggtcctgaaa atctagtaac aactataaaa     600

aatccaacta tggagtctct agatgcaatt attaagcatc cttcaataaa acttctttgc     660

ggaactgggg gtccaggaat ggtaaaaacc ctcttaaatt ctggtaagaa agctataggt     720
```

```
gctggtgctg gaaatccacc agttattgta gatgatactg ctgatataga aaaggctggt     780

aggagcatca ttgaaggctg ttcttttgat aataatttac cttgtattgc agaaaaagaa     840

gtatttgttt ttgagaatgt tgcagatgat ttaatatcta acatgctaaa aaataatgct     900

gtaattataa atgaagatca agtatcaaaa ttaatagatt tagtattaca aaaaaataat     960

gaaactcaag aatactttat aaacaaaaaa tgggtaggaa aagatgcaaa attattctta    1020

gatgaaatag atgttgagtc tccttcaaat gttaaatgca taatctgcga agtaaatgca    1080

aatcatccat ttgttatgac agaactcatg atgccaatat tgccaattgt aagagttaaa    1140

gatatagatg aagctattaa atatgcaaag atagcagaac aaaatagaaa acatagtgcc    1200

tatatttatt ctaaaaatat agacaaccta aatagatttg aaagagaaat agatactact    1260

atttttgtaa agaatgctaa atcttttgct ggtgttggtt atgaagcaga aggatttaca    1320

actttcacta ttgctggatc tactggtgag ggaataacct ctgcaaggaa ttttacaaga    1380

caaagaagat gtgtacttgc cggctaa                                        1407
```

<210> SEQ ID NO 12
<211> LENGTH: 468
<212> TYPE: PRT
<213> ORGANISM: Clostridium beijerinckii

<400> SEQUENCE: 12

```
Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255
```

```
Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465
```

<210> SEQ ID NO 13
<211> LENGTH: 1215
<212> TYPE: DNA
<213> ORGANISM: Clostridium acetobutylicum

<400> SEQUENCE: 13

```
atggttgatt tcgaatattc aataccaact agaatttttt tcggtaaaga taagataaat      60

gtacttggaa gagagcttaa aaaatatggt tctaaagtgc ttatagttta tggtggagga     120

agtataaaga gaaatggaat atatgataaa gctgtaagta tacttgaaaa aaacagtatt     180

aaattttatg aacttgcagg agtagagcca aatccaagag taactacagt tgaaaaagga     240

gttaaaatat gtagagaaaa tggagttgaa gtagtactag ctataggtgg aggaagtgca     300

atagattgcg caaaggttat agcagcagca tgtgaatatg atggaaatcc atgggatatt     360

gtgttagatg gctcaaaaat aaaaagggtg cttcctatag ctagtatatt aaccattgct     420

gcaacaggat cagaaatgga tacgtgggca gtaataaata atatggatac aaacgaaaaa     480

ctaattgcgg cacatccaga tatggctcct aagttttcta tattagatcc aacgtatacg     540

tataccgtac ctaccaatca aacagcagca ggaacagctg atattatgag tcatatattt     600

gaggtgtatt ttagtaatac aaaaacagca tatttgcagg atagaatggc agaagcgtta     660

ttaagaactt gtattaaata tggaggaata gctcttgaga agccggatga ttatgaggca     720

agagccaatc taatgtgggc ttcaagtctt gcgataaatg gacttttaac atatggtaaa     780

gacactaatt ggagtgtaca cttaatggaa catgaattaa gtgcttatta cgacataaca     840

cacggcgtag ggcttgcaat tttaacacct aattggatgg agtatatttt aaataatgat     900
```

```
acagtgtaca agtttgttga atatggtgta aatgtttggg gaatagacaa agaaaaaaat    960

cactatgaca tagcacatca agcaatacaa aaaacaagag attactttgt aaatgtacta   1020

ggtttaccat ctagactgag agatgttgga attgaagaag aaaaattgga cataatggca   1080

aaggaatcag taaagcttac aggaggaacc ataggaaacc taagaccagt aaacgcctcc   1140

gaagtcctac aaatattcaa aaaatctgtg taaaacgcct ccgaagtcct acaaatattc   1200

aaaaaatctg tgtaa                                                    1215
```

<210> SEQ ID NO 14
<211> LENGTH: 390
<212> TYPE: PRT
<213> ORGANISM: Clostridium acetobutylicum

<400> SEQUENCE: 14

```
Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320
```

```
His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390


<210> SEQ ID NO 15
<211> LENGTH: 1170
<212> TYPE: DNA
<213> ORGANISM: Clostridium acetobutylicum

<400> SEQUENCE: 15

atgctaagtt ttgattattc aataccaact aaagtttttt ttggaaaagg aaaaatagac      60

gtaattggag aagaaattaa gaaatatggc tcaagagtgc ttatagttta tggcggagga     120

agtataaaaa ggaacggtat atatgataga gcaacagcta tattaaaaga aaacaatata     180

gctttctatg aactttcagg agtagagcca aatcctagga taacaacagt aaaaaaaggc     240

atagaaatat gtagagaaaa taatgtggat ttagtattag caatagggggg aggaagtgca    300

atagactgtt ctaaggtaat tgcagctgga gtttattatg atggcgatac atgggacatg     360

gttaaagatc catctaaaat aactaaagtt cttccaattg caagtatact tactctttca     420

gcaacagggt ctgaaatgga tcaaattgca gtaatttcaa atatggagac taatgaaaag     480

cttggagtag gacatgatga tatgagacct aaattttcag tgttagatcc tacatatact     540

tttacagtac ctaaaaatca aacagcagcg ggaacagctg acattatgag tcacaccttt     600

gaatcttact ttagtggtgt tgaaggtgct tatgtgcagg acggtatagc agaagcaatc     660

ttaagaacat gtataaagta tggaaaaata gcaatggaga agactgatga ttacgaggct     720

agagctaatt tgatgtgggc ttcaagttta gctataaatg gtctattatc acttggtaag     780

gatagaaaat ggagttgtca tcctatggaa cacgagttaa gtgcatatta tgatataaca     840

catggtgtag gacttgcaat tttaacacct aattggatgg aatatattct aaatgacgat     900

acacttcata aatttgtttc ttatggaata aatgtttggg gaatagacaa gaacaaagat     960

aactatgaaa tagcacgaga ggctattaaa aatacgagag aatactttaa ttcattgggt    1020

attccttcaa agcttagaga agttggaata ggaaaagata aactagaact aatggcaaag    1080

caagctgtta gaaattctgg aggaacaata ggaagtttaa gaccaataaa tgcagaggat    1140

gttcttgaga tatttaaaaa atcttattaa                                     1170


<210> SEQ ID NO 16
<211> LENGTH: 389
<212> TYPE: PRT
<213> ORGANISM: Clostridium acetobutylicum

<400> SEQUENCE: 16

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45
```

```
Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385
```

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
caccatggaa ctaaacaatg tcatccttg 29

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
cctcctatct atttttgaag ccttc 25

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
caccatgaaa aaggtatgtg ttataggt 28

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
catttgataa tggggattct tgt 23

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
caccatgaaa gaagttgtaa tagctagtgc 30

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
ctagcacttt tctagcaata ttgctg 26

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
caccatgcta agttttgatt attcaatac 29

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
ttaataagat tttttaaata tctca 25

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
caccatggtt gatttcgaat attcaatacc 30

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
ttacacagat tttttgaata tttgt 25

<210> SEQ ID NO 27
<211> LENGTH: 32
<212> TYPE: DNA
<213> ORGANISM: Artificial Sequence
<220> FEATURE:
<223> OTHER INFORMATION: Primer

<400> SEQUENCE: 27
caccatgaga gatgtagtaa tagtaagtgc tg 32

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
ccgcaattgt atccatattg aacc 24

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
caccatgata gtaaaagcaa agtttg 26

<210> SEQ ID NO 30
<211> LENGTH: 27
<212> TYPE: DNA
<213> ORGANISM: Artificial Sequence
<220> FEATURE:
<223> OTHER INFORMATION: Primer

<400> SEQUENCE: 30
gcttaaagct taaaaccgct tctggcg 27

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
caccatgaat aaagacacac taatacc 27

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
gccagaccat ctttgaaaat gcgc 24

<210> SEQ ID NO 33
<211> LENGTH: 35
<212> TYPE: DNA
<213> ORGANISM: Artificial Sequence
<220> FEATURE:
<223> OTHER INFORMATION: Primer

<400> SEQUENCE: 33
catgcatgca aaggaggtta gtagaatgaa agaag 35

<210> SEQ ID NO 34
<211> LENGTH: 38
<212> TYPE: DNA
<213> ORGANISM: Artificial Sequence
<220> FEATURE:
<223> OTHER INFORMATION: Primer

<400> SEQUENCE: 34
gtcctgcagg gcgcgcccaa tactttctag cacttttc 38

<210> SEQ ID NO 35
<211> LENGTH: 39
<212> TYPE: DNA
<213> ORGANISM: Artificial Sequence
<220> FEATURE:
<223> OTHER INFORMATION: Primer

<400> SEQUENCE: 35
catgtcgaca aaggaggtct gtttaatgaa aaaggtatg 39

<210> SEQ ID NO 36
<211> LENGTH: 28
<212> TYPE: DNA
<213> ORGANISM: Artificial Sequence
<220> FEATURE:
<223> OTHER INFORMATION: Primer

<400> SEQUENCE: 36
gtcgcatgcc ttgtaaactt attttgaa 28

<210> SEQ ID NO 37
<211> LENGTH: 44
<212> TYPE: DNA
<213> ORGANISM: Artificial Sequence
<220> FEATURE:
<223> OTHER INFORMATION: Primer

<400> SEQUENCE: 37
catagatctg gatccaaagg agggtgagga aatgatagta aaag 44

<210> SEQ ID NO 38
<211> LENGTH: 30
<212> TYPE: DNA
<213> ORGANISM: Artificial Sequence
<220> FEATURE:
<223> OTHER INFORMATION: Primer

<400> SEQUENCE: 38
catgtcgacg tgcagccttt ttaaggttct 30

<210> SEQ ID NO 39
<211> LENGTH: 38
<212> TYPE: DNA
<213> ORGANISM: Artificial Sequence
<220> FEATURE:
<223> OTHER INFORMATION: Primer

<400> SEQUENCE: 39
catgaattca cgcgtaaagg aggtattagt catggaac 38

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
gtcggatccc ttacctccta tctatttttg 30

<210> SEQ ID NO 41
<211> LENGTH: 42
<212> TYPE: DNA
<213> ORGANISM: Artificial Sequence
<220> FEATURE:
<223> OTHER INFORMATION: Primer

<400> SEQUENCE: 41
catgcccggg ggtcaccaaa ggaggaatag ttcatgaata aa 42

<210> SEQ ID NO 42
<211> LENGTH: 32
<212> TYPE: DNA
<213> ORGANISM: Artificial Sequence
<220> FEATURE:
<223> OTHER INFORMATION: Primer

<400> SEQUENCE: 42
catggttaac aagaagttag ccggcaagta ca 32

<210> SEQ ID NO 43
<211> LENGTH: 41
<212> TYPE: DNA
<213> ORGANISM: Artificial Sequence
<220> FEATURE:
<223> OTHER INFORMATION: Primer

<400> SEQUENCE: 43
catggttaac aaaggagggg ttaaaatggt tgatttcgaa t 41

<210> SEQ ID NO 44
<211> LENGTH: 37
<212> TYPE: DNA
<213> ORGANISM: Artificial Sequence
<220> FEATURE:
<223> OTHER INFORMATION: Primer

<400> SEQUENCE: 44
catggcatgc gtttaaacgt aggtttacac agatttt 37

<210> SEQ ID NO 45
<211> LENGTH: 17
<212> TYPE: DNA
<213> ORGANISM: Artificial Sequence
<220> FEATURE:
<223> OTHER INFORMATION: Primer

<400> SEQUENCE: 45
gtaaaacgac ggccagt 17

<210> SEQ ID NO 46
<211> LENGTH: 16
<212> TYPE: DNA
<213> ORGANISM: Artificial Sequence
<220> FEATURE:
<223> OTHER INFORMATION: Primer

<400> SEQUENCE: 46
aacagctatg accatg 16

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
gcaggagatg ctgacgtaat aa 22

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
ccaacctgct ttttcaatag ctgc 24

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
cagagatggg gtcaaagaat g 21

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
gtggttttat tccgagagcg 20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
ggtctatact tagaatctcc 20

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
cggaacagtt gaccttaata tggc 24

<210> SEQ ID NO 53
<211> LENGTH: 22
<212> TYPE: DNA
<213> ORGANISM: Artificial Sequence
<220> FEATURE:
<223> OTHER INFORMATION: Primer

<400> SEQUENCE: 53
gcctcatctg ggtttggtct tg 22

<210> SEQ ID NO 54
<211> LENGTH: 28
<212> TYPE: DNA
<213> ORGANISM: Artificial Sequence
<220> FEATURE:
<223> OTHER INFORMATION: Primer

<400> SEQUENCE: 54
cgcctaggag aaaggactat aaaactgg 28

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
cagagttata ggtggtagag cc 22

<210> SEQ ID NO 56
<211> LENGTH: 24
<212> TYPE: DNA
<213> ORGANISM: Artificial Sequence
<220> FEATURE:
<223> OTHER INFORMATION: Primer

<400> SEQUENCE: 56
ccatcccgct gttcctattc ttct 24

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
ccaatcctct ccacccatta cc 22

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
cgtccatcct taatcttccc 20

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
ccaactatgg aatccctaga tgc 23

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
gcatagtctg cgaagtaaat gc 22

<210> SEQ ID NO 61
<211> LENGTH: 24
<212> TYPE: DNA
<213> ORGANISM: Artificial Sequence
<220> FEATURE:
<223> OTHER INFORMATION: Primer

<400> SEQUENCE: 61
ggatctactg gtgaaggcat aacc 24

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
ggcatcatga gttctgtcat gac 23

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
gccttcaatg atactcttac cagcc 25

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
gcatttccag cagctatcat gc 22

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
ccttcccata tgtgtttctt cc 22

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
gttgaagtag tactagctat ag 22

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
gacataacac acggcgtagg gc 22

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
taagtgtaca ctccaattag tg 22

<210> SEQ ID NO 69
<211> LENGTH: 24
<212> TYPE: DNA
<213> ORGANISM: Artificial Sequence
<220> FEATURE:
<223> OTHER INFORMATION: Primer

<400> SEQUENCE: 69
gccatctaac acaatatccc atgg 24

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
gcgatacatg ggacatggtt aaag 24

<210> SEQ ID NO 71
<211> LENGTH: 22
<212> TYPE: DNA
<213> ORGANISM: Artificial Sequence
<220> FEATURE:
<223> OTHER INFORMATION: Primer

<400> SEQUENCE: 71
tgcacttaac tcgtgttcca ta 22

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
gttagccggc aagtacacat c 21

<210> SEQ ID NO 73
<211> LENGTH: 21
<212> TYPE: DNA
<213> ORGANISM: Artificial Sequence
<220> FEATURE:
<223> OTHER INFORMATION: Primer

<400> SEQUENCE: 73
actttctttc gcctgtttca c 21

<210> SEQ ID NO 74
<211> LENGTH: 47
<212> TYPE: DNA
<213> ORGANISM: Artificial Sequence
<220> FEATURE:
<223> OTHER INFORMATION: Primer

<400> SEQUENCE: 74
catgaagctt ggcgcgccgg gacgcgtttt tgaaaataat gaaaact 47

<210> SEQ ID NO 75
<211> LENGTH: 79
<212> TYPE: DNA
<213> ORGANISM: Artificial Sequence
<220> FEATURE:
<223> OTHER INFORMATION: Primer

<400> SEQUENCE: 75
catgaagctt gtttaaactc ggtgaccttg aaaataatga aaacttatat tgttttgaaa 60
ataatgaaaa cttatattg 79

<210> SEQ ID NO 76
<211> LENGTH: 1197
<212> TYPE: DNA
<213> ORGANISM: Artificial Sequence
<220> FEATURE:
<223> OTHER INFORMATION: Codon optimized CAC0462 gene from Clostridium acetobutylicum

<400> SEQUENCE: 76
atgattgtga aagcaaaatt cgtgaaagga ttcattcgcg atgtgcaccc ttatgggtgc 60
cgccgtgaag ttctgaatca gatcgactac tgcaaaaaag ccattggctt tcgcggccca 120
aagaaagtgc tgatcgttgg tgcttcctct ggcttcggtc tggctacccg catttccgtg 180
gcgttcggtg gcccagaagc ccacactatc ggcgtcagct atgaaaccgg tgcgaccgat 240
cgccgtattg gcacagcagg gtggtataac aatattttct ttaaagaatt tgccaaaaag 300
aaaggcctgg tggcaaaaaa ctttatcgaa gacgccttct cgaacgaaac caaggacaaa 360

```
gtcatcaaat atattaaaga cgaatttggc aaaatcgatc tgttcgttta ctcgctggca    420

gcaccgcgtc gtaaggatta taagactggg aacgtttata cctcacgtat taaaacgatc    480

ctgggtgatt ttgaagggcc gactatcgat gtggaacgtg atgaaattac actgaaaaag    540

gtctcatctg cgtcaatcga agagattgaa gaaacccgta aggtgatggg cggcgaagat    600

tggcaagagt ggtgtgaaga actgctgtac gaagattgtt tcagtgataa agccaccacc    660

atcgcctatt cctatatcgg ttctcctcgc acctacaaaa tctaccgcga aggcactatc    720

ggcattgcga aaaaggatct ggaagataag gcaaaactga tcaacgagaa gctgaatcgc    780

gtcattggcg ggcgcgcatt cgttagcgtg aataaagccc tggttactaa ggcgagcgca    840

tatattccga cctttcctct gtacgccgca attctgtata aagttatgaa agaaaagaat    900

attcacgaaa actgcattat gcaaattgaa cgcatgtttt ccgagaaaat ttattcaaat    960

gaaaagattc aatttgatga taaaggtcgt ctgcgtatgg atgacctgga gctgcgtaag   1020

gatgttcagg atgaagtaga ccgtatttgg agcaatatta caccggagaa ttttaaggaa   1080

ctgagcgact ataaaggcta caaaaaagaa tttatgaacc tgaatggatt tgatctggac   1140

ggcgtggatt attcaaagga tctggacatt gaactgctgc gcaaactgga accataa      1197
```

<210> SEQ ID NO 77
<211> LENGTH: 1224
<212> TYPE: DNA
<213> ORGANISM: Artificial Sequence
<220> FEATURE:
<223> OTHER INFORMATION: Condon optimized EgTER

<400> SEQUENCE: 77

```
atggcgatgt ttacgaccac cgcaaaagtt attcagccga aaattcgtgg ttttatttgc     60

accaccaccc acccgattgg ttgcgaaaaa cgtgttcagg aagaaatcgc atacgcacgc    120

gcgcacccgc cgaccagccc gggtccgaaa cgtgtgctgg ttattggctg cagtacgggc    180

tatggcctga gcacccgtat caccgcggcc tttggttatc aggccgcaac cctgggcgtg    240

tttctggcag gcccgccgac caaaggccgt ccggccgcgg cgggttggta taatacggtt    300

gcgttcgaaa aagccgccct ggaagcaggt ctgtatgcac gttctctgaa tggtgatgcg    360

ttcgattcta ccacgaaagc ccgcaccgtg gaagcaatta aacgtgatct gggtaccgtt    420

gatctggtgg tgtatagcat tgcagcgccg aaacgtaccg atccggccac cggcgtgctg    480

cataaagcgt gcctgaaacc gattggtgca acctacacca atcgtacggt gaacaccgat    540

aaagcagaag ttaccgatgt gagtattgaa ccggccagtc cggaagaaat cgcagatacc    600

gtgaaagtta tgggtggcga agattgggaa ctgtggattc aggcactgag cgaagccggc    660

gtgctggccg aaggcgcaaa aaccgttgcg tattcttata ttggcccgga aatgacgtgg    720

ccggtgtatt ggagtggcac cattggcgaa gccaaaaaag atgttgaaaa agcggcgaaa    780

cgcatcaccc agcagtacgg ctgtccggcg tatccggttg ttgccaaagc gctggtgacc    840

caggccagta gcgccattcc ggtggtgccg ctgtatattt gcctgctgta tcgtgttatg    900

aaagaaaaag gcacccatga aggctgcatt gaacagatgg tgcgtctgct gacgacgaaa    960

ctgtatccgg aaaatggtgc gccgatcgtg gatgaagcgg gccgtgtgcg tgttgatgat   1020

tgggaaatgg cagaagatgt tcagcaggca gttaaagatc tgtggagcca ggtgagtacg   1080

gccaatctga aagatattag cgattttgca ggttatcaga ccgaatttct gcgtctgttt   1140

ggctttggta ttgatggtgt ggattacgat cagccggttg atgttgaagc ggatctgccg   1200

agcgccgccc agcagtaagt cgac                                          1224
```

<210> SEQ ID NO 78
<211> LENGTH: 1498
<212> TYPE: DNA
<213> ORGANISM: Artificial Sequence
<220> FEATURE:
<223> OTHER INFORMATION: Codon optimized ald gene

<400> SEQUENCE: 78
cggtacctcg cgaatgcatc tagatccaat catgcccggg ggtcaccaaa ggaggaatag 60
ttcatgaata aagatacgct gattccgacc acgaaagatc tgaaagtgaa aaccaacggt 120
gaaaatatca acctgaaaaa ttataaagat aatagcagct gcttcggcgt gtttgaaaat 180
gttgaaaacg ccatttcttc tgccgttcac gcacagaaaa tcctgtctct gcactatacc 240
aaagaacagc gcgaaaaaat cattaccgaa attcgcaaag cggccctgca gaataaagaa 300
gttctggcga ccatgatcct ggaagaaacc catatgggtc gttacgaaga taaaatcctg 360
aaacatgaac tggtggcgaa atacacgccg ggtacggaag atctgaccac gaccgcatgg 420
agcggtgata acggtctgac cgtggtggaa atgtctccgt atggcgttat tggcgcaatt 480
acgccgagca cgaatccgac cgaaacggtt atttgtaaca gtattggcat gattgcagcc 540
ggtaatgcag tggttttcaa tggtcatccg tgcgccaaaa aatgtgtggc gtttgccgtt 600
gaaatgatta acaaagcgat tattagctgc ggtggcccgg aaaatctggt gacgacgatt 660
aaaaacccga ccatggaaag tctggatgcg attattaaac atccgtctat taaactgctg 720
tgtggtaccg gcggtccggg tatggtgaaa accctgctga attctggcaa aaaagcaatt 780
ggcgcgggtg cgggtaatcc gccggttatc gttgatgata ccgcggatat tgaaaaagca 840
ggccgcagta ttattgaagg ttgtagcttt gataataacc tgccgtgcat tgccgaaaaa 900
gaagtgtttg ttttcgaaaa tgtggcggat gatctgatca gcaacatgct gaaaaataac 960
gccgtgatta ttaacgaaga tcaggtgtct aaactgattg atctggttct gcagaaaaac 1020
aacgaaacgc aggaatattt cattaataaa aaatgggttg gtaaagatgc gaaactgttc 1080
ctggatgaaa tcgatgtgga aagtccgagc aacgtgaaat gtatcatctg cgaagtgaat 1140
gccaaccatc cgtttgttat gacggaactg atgatgccga ttctgccgat tgttcgtgtt 1200
aaagatattg atgaagccat caaatatgcg aaaattgcgg aacagaaccg caaacacagc 1260
gcatatattt acagtaaaaa catcgataac ctgaaccgtt tcgaacgtga aattgatacc 1320
accatctttg tgaaaaatgc caaaagtttt gcgggtgttg gctatgaagc cgaaggcttt 1380
accacgttca ccattgcagg ttctaccggc gaaggtatta ccagcgcgcg taattttacc 1440
cgccagcgcc gctgtgtgct ggcgggttaa gttaacccaa tatcggatcc cgggcccg 1498

<210> SEQ ID NO 79
<211> LENGTH: 6509
<212> TYPE: DNA
<213> ORGANISM: Artificial sequence
<220> FEATURE:
<223> OTHER INFORMATION: plasmid pFP988

<400> SEQUENCE: 79
tcgaggcccc gcacatacga aaagactggc tgaaaacatt gagcctttga tgactgatga 60
tttggctgaa gaagtggatc gattgtttga gaaaagaaga agaccataaa aataccttgt 120
ctgtcatcag acagggtatt ttttatgctg tccagactgt ccgctgtgta aaaaatagga 180
ataaaggggg gttgttatta ttttactgat atgtaaaata taatttgtat aaggaattgt 240
gagcggataa caattcctac gaaaatgaga gggagaggaa acatgattca aaaacgaaag 300

```
cggacagttt cgttcagact tgtgcttatg tgcacgctgt tatttgtcag tttgccgatt    360
acaaaaacat cagccggatc ccaccatcac catcaccatt aagaattcct agaaactcca    420
agctatcttt aaaaaatcta gtaaatgcac gagcaacatc ttttgttgct cagtgcattt    480
tttattttgt acactagata tttcttctcc gcttaaatca tcaaagaaat ctttatcact    540
tgtaaccagt ccgtccacat gtcgaattgc atctgaccga attttacgtt tccctgaata    600
attctcatca atcgtttcat caattttatc tttatacttt atattttgtg cgttaatcaa    660
atcataattt ttatatgttt cctcatgatt tatgtcttta ttattatagt ttttattctc    720
tctttgatta tgtctttgta tcccgtttgt attacttgat cctttaactc tggcaaccct    780
caaaattgaa tgagacatgc tacacctccg gataataaat atatataaac gtatatagat    840
ttcataaagt ctaacacact agacttattt acttcgtaat taagtcgtta aaccgtgtgc    900
tctacgacca aaactataaa acctttaaga actttctttt tttacaagaa aaaagaaatt    960
agataaatct ctcatatctt ttattcaata atcgcatccg attgcagtat aaatttaacg   1020
atcactcatc atgttcatat ttatcagagc tcgtgctata attatactaa ttttataagg   1080
aggaaaaaat atgggcattt ttagtatttt tgtaatcagc acagttcatt atcaaccaaa   1140
caaaaaataa gtggttataa tgaatcgtta ataagcaaaa ttcatataac caaattaaag   1200
agggttataa tgaacgagaa aaatataaaa cacagtcaaa actttattac ttcaaaacat   1260
aatatagata aaataatgac aaatataaga ttaaatgaac atgataatat ctttgaaatc   1320
ggctcaggaa aaggccattt tacccttgaa ttagtaaaga ggtgtaattt cgtaactgcc   1380
attgaaatag accataaatt atgcaaaact acagaaaata aacttgttga tcacgataat   1440
ttccaagttt taaacaagga tatattgcag tttaaatttc ctaaaaacca atcctataaa   1500
atatatggta atatacctta taacataagt acggatataa tacgcaaaat tgtttttgat   1560
agtatagcta atgagattta tttaatcgtg gaatacgggt ttgctaaaag attattaaat   1620
acaaaacgct cattggcatt acttttaatg gcagaagttg atatttctat attaagtatg   1680
gttccaagag aatattttca tcctaaacct aaagtgaata gctcacttat cagattaagt   1740
agaaaaaaat caagaatatc acacaaagat aaacaaaagt ataattattt cgttatgaaa   1800
tgggttaaca aagaatacaa gaaaatattt acaaaaaatc aatttaacaa ttccttaaaa   1860
catgcaggaa ttgacgattt aaacaatatt agctttgaac aattcttatc tcttttcaat   1920
agctataaat tatttaataa gtaagttaag ggatgcagtt catcgatgaa ggcaactaca   1980
gctcaggcga caaccatacg ctgagagatc ctcactacgt agaagataaa ggccacaaat   2040
acttagtatt tgaagcaaac actggaactg aagatggcta ccaaggcgaa gaatctttat   2100
ttaacaaagc atactatggc aaaagcacat cattcttccg tcaagaaagt caaaaacttc   2160
tgcaaagcga taaaaaacgc acggctgagt tagcaaacgg cgctctcggt atgattgagc   2220
taaacgatga ttacacactg aaaaaagtga tgaaaccgct gattgcatct aacacagtaa   2280
cagatgaaat tgaacgcgcg aacgtcttta aaatgaacgg caaatggtac ctgttcactg   2340
actcccgcgg atcaaaaatg acgattgacg gcattacgtc taacgatatt tacatgcttg   2400
gttatgtttc taattcttta actggcccat acaagccgct gaacaaaact ggccttgtgt   2460
taaaaatgga tcttgatcct aacgatgtaa cctttactta ctcacacttc gctgtacctc   2520
aagcgaaagg aaacaatgtc gtgattacaa gctatatgac aaacagagga ttctacgcag   2580
acaaacaatc aacgtttgcg ccaagcttgc atgcgagagt agggaactgc caggcatcaa   2640
ataaaacgaa aggctcagtc gaaagactgg gcctttcgtt ttatctgttg tttgtcggtg   2700
```

-continued

```
aacgctctcc tgagtaggac aaatccgccg ggagcggatt tgaacgttgc gaagcaacgg   2760

cccggagggt ggcgggcagg acgcccgcca taaactgcca ggcatcaaat taagcagaag   2820

gccatcctga cggatggcct ttttgcgttt ctacaaactc tttttgttta tttttctaaa   2880

tacattcaaa tatgtatccg ctcatgctcc ggatctgcat cgcaggatgc tgctggctac   2940

cctgtggaac acctacatct gtattaacga agcgctggca ttgaccctga gtgatttttc   3000

tctggtcccg ccgcatccat accgccagtt gtttaccctc acaacgttcc agtaaccggg   3060

catgttcatc atcagtaacc cgtatcgtga gcatcctctc tcgtttcatc ggtatcatta   3120

cccccatgaa cagaaattcc cccttacacg gaggcatcaa gtgaccaaac aggaaaaaac   3180

cgcccttaac atggcccgct ttatcagaag ccagacatta acgcttctgg agaaactcaa   3240

cgagctggac gcggatgaac aggcagacat ctgtgaatcg cttcacgacc acgctgatga   3300

gctttaccgc agctgcctcg cgcgtttcgg tgatgacggt gaaaacctct gacacatgca   3360

gctcccggag acggtcacag cttgtctgta agcggatgcc gggagcagac aagcccgtca   3420

gggcgcgtca gcgggtgttg gcgggtgtcg gggcgcagcc atgacccagt cacgtagcga   3480

tagcggagtg tatactggct taactatgcg gcatcagagc agattgtact gagagtgcac   3540

catatgcggt gtgaaatacc gcacagatgc gtaaggagaa aataccgcat caggcgctct   3600

tccgcttcct cgctcactga ctcgctgcgc tcggtcgttc ggctgcggcg agcggtatca   3660

gctcactcaa aggcggtaat acggttatcc acagaatcag gggataacgc aggaaagaac   3720

atgtgagcaa aaggccagca aaaggccagg aaccgtaaaa aggccgcgtt gctggcgttt   3780

ttccataggc tccgcccccc tgacgagcat cacaaaaatc gacgctcaag tcagaggtgg   3840

cgaaacccga caggactata aagataccag gcgtttcccc ctggaagctc cctcgtgcgc   3900

tctcctgttc cgaccctgcc gcttaccgga tacctgtccg cctttctccc ttcgggaagc   3960

gtggcgcttt ctcaatgctc acgctgtagg tatctcagtt cggtgtaggt cgttcgctcc   4020

aagctgggct gtgtgcacga accccccgtt cagcccgacc gctgcgcctt atccggtaac   4080

tatcgtcttg agtccaaccc ggtaagacac gacttatcgc cactggcagc agccactggt   4140

aacaggatta gcagagcgag gtatgtaggc ggtgctacag agttcttgaa gtggtggcct   4200

aactacggct acactagaag gacagtattt ggtatctgcg ctctgctgaa gccagttacc   4260

ttcggaaaaa gagttggtag ctcttgatcc ggcaaacaaa ccaccgctgg tagcggtggt   4320

tttttgttt gcaagcagca gattacgcgc agaaaaaaag gatctcaaga agatcctttg   4380

atcttttcta cggggtctga cgctcagtgg aacgaaaact cacgttaagg gattttggtc   4440

atgagattat caaaaaggat cttcacctag atccttttaa attaaaaatg aagttttaaa   4500

tcaatctaaa gtatatatga gtaaacttgg tctgacagtt accaatgctt aatcagtgag   4560

gcacctatct cagcgatctg tctatttcgt tcatccatag ttgcctgact ccccgtcgtg   4620

tagataacta cgatacggga gggcttacca tctggcccca gtgctgcaat gataccgcga   4680

gacccacgct caccggctcc agatttatca gcaataaacc agccagccgg aagggccgag   4740

cgcagaagtg gtcctgcaac tttatccgcc tccatccagt ctattaattg ttgccgggaa   4800

gctagagtaa gtagttcgcc agttaatagt ttgcgcaacg ttgttgccat tgctgcaggc   4860

atcgtggtgt cacgctcgtc gtttggtatg gcttcattca gctccggttc ccaacgatca   4920

aggcgagtta catgatcccc catgttgtgc aaaaaagcgg ttagctcctt cggtcctccg   4980

atcgttgtca gaagtaagtt ggccgcagtg ttatcactca tggttatggc agcactgcat   5040

aattctctta ctgtcatgcc atccgtaaga tgcttttctg tgactggtga gtactcaacc   5100
```

```
aagtcattct gagaatagtg tatgcggcga ccgagttgct cttgcccggc gtcaatacgg   5160

gataataccg cgccacatag cagaacttta aaagtgctca tcattggaaa acgttcttcg   5220

gggcgaaaac tctcaaggat cttaccgctg ttgagatcca gttcgatgta acccactcgt   5280

gcacccaact gatcttcagc atcttttact ttcaccagcg tttctgggtg agcaaaaaca   5340

ggaaggcaaa atgccgcaaa aaagggaata agggcgacac ggaaatgttg aatactcata   5400

ctcttccttt ttcaatatta ttgaagcatt tatcagggtt attgtctcat gagcggatac   5460

atatttgaat gtatttagaa aaataaacaa ataggggttc cgcgcacatt tccccgaaaa   5520

gtgccacctg acgtctaaga aaccattatt atcatgacat taacctataa aaataggcgt   5580

atcacgaggc cctttcgtct cgcgcgtttc ggtgatgacg gtgaaaacct ctgacacatg   5640

cagctcccgg agacggtcac agcttgtctg taagcggatg ccgggagcag acaagcccgt   5700

cagggcgcgt cagcgggtgt tcatgtgcgt aactaacttg ccatcttcaa acaggagggc   5760

tggaagaagc agaccgctaa cacagtacat aaaaaaggag acatgaacga tgaacatcaa   5820

aaagtttgca aaacaagcaa cagtattaac ctttactacc gcactgctgg caggaggcgc   5880

aactcaagcg tttgcgaaag aaacgaacca aaagccatat aaggaaacat acggcatttc   5940

ccatattaca cgccatgata tgctgcaaat ccctgaacag caaaaaaatg aaaaatatca   6000

agttcctgaa ttcgattcgt ccacaattaa aaatatctct tctgcaaaag gcctggacgt   6060

ttgggacagc tggccattac aaaacgctga cggcactgtc gcaaactatc acggctacca   6120

catcgtcttt gcattagccg gagatcctaa aaatgcggat gacacatcga tttacatgtt   6180

ctatcaaaaa gtcggcgaaa cttctattga cagctggaaa aacgctggcc gcgtctttaa   6240

agacagcgac aaattcgatg caaatgattc tatcctaaaa gaccaaacac aagaatggtc   6300

aggttcagcc acatttacat ctgacggaaa aatccgttta ttctacactg atttctccgg   6360

taaacattac ggcaaacaaa cactgacaac tgcacaagtt aacgtatcag catcagacag   6420

ctctttgaac atcaacggtg tagaggatta taaatcaatc tttgacggtg acggaaaaac   6480

gtatcaaaat gtacagcatg ccacgcgtc                                     6509
```

<210> SEQ ID NO 80
<211> LENGTH: 46
<212> TYPE: DNA
<213> ORGANISM: Artificial sequence
<220> FEATURE:
<223> OTHER INFORMATION: primer N85

<400> SEQUENCE: 80

```
catagatctg gatccaaagg agggtgagga aatggcgatg tttacg                    46
```

<210> SEQ ID NO 81
<211> LENGTH: 20
<212> TYPE: DNA
<213> ORGANISM: artificial sequence
<220> FEATURE:
<223> OTHER INFORMATION: primer N86

<400> SEQUENCE: 81

```
gtcgacttac tgctgggcgg                                                 20
```

<210> SEQ ID NO 82
<211> LENGTH: 20
<212> TYPE: DNA
<213> ORGANISM: Artificial sequence
<220> FEATURE:
<223> OTHER INFORMATION: T7 primer

<400> SEQUENCE: 82
taatacgact cactataggg 20

<210> SEQ ID NO 83
<211> LENGTH: 20
<212> TYPE: DNA
<213> ORGANISM: artificial sequence
<220> FEATURE:
<223> OTHER INFORMATION: Primer Trc99af

<400> SEQUENCE: 83
ttgacaatta atcatccggc 20

<210> SEQ ID NO 84
<211> LENGTH: 21
<212> TYPE: DNA
<213> ORGANISM: artificial sequence
<220> FEATURE:
<223> OTHER INFORMATION: Primer N5SeqF4

<400> SEQUENCE: 84
ggtcaactgt tccggaaatt c 21

<210> SEQ ID NO 85
<211> LENGTH: 46
<212> TYPE: DNA
<213> ORGANISM: artificial sequence
<220> FEATURE:
<223> OTHER INFORMATION: Primer T-ald(BamHI)

<400> SEQUENCE: 85
tgatctggat ccaagaagga gcccttcacc atgaataaag acacac 46

<210> SEQ ID NO 86
<211> LENGTH: 54
<212> TYPE: DNA
<213> ORGANISM: artificial sequence
<220> FEATURE:
<223> OTHER INFORMATION: Primer B-ald(ETGER)

<400> SEQUENCE: 86
catcgccatt tcctcaccct cctttttagc cggcaagtac acatcttctt tgtc 54

<210> SEQ ID NO 87
<211> LENGTH: 42
<212> TYPE: DNA
<213> ORGANISM: artificial sequence
<220> FEATURE:
<223> OTHER INFORMATION: Primer T-Ptrc(BspEI)

<400> SEQUENCE: 87
ttccgtactt ccggacgact gcacggtgca ccaatgcttc tg 42

<210> SEQ ID NO 88
<211> LENGTH: 43
<212> TYPE: DNA
<213> ORGANISM: artificial sequence
<220> FEATURE:
<223> OTHER INFORMATION: Primer B-aldopt(BspEI)

<400> SEQUENCE: 88
cggatcttaa gtactttaac ccgccagcac acagcggcgc tgg 43

<210> SEQ ID NO 89
<211> LENGTH: 32
<212> TYPE: DNA

<213> ORGANISM: artificial sequence
<220> FEATURE:
<223> OTHER INFORMATION: Primer T-BspEIAatII

<400> SEQUENCE: 89
ccggatcatg ataataatgg tttcttagac gt 32

<210> SEQ ID NO 90
<211> LENGTH: 24
<212> TYPE: DNA
<213> ORGANISM: artificial sequence
<220> FEATURE:
<223> OTHER INFORMATION: Primer B-BspEIAatII

<400> SEQUENCE: 90
ctaagaaacc attattatca tgat 24

<210> SEQ ID NO 91
<211> LENGTH: 42
<212> TYPE: DNA
<213> ORGANISM: artificial sequence
<220> FEATURE:
<223> OTHER INFORMATION: 1.6GI promoter

<400> SEQUENCE: 91
gcccttgaca atgccacatc ctgagcaaat aattcaacca ct 42

<210> SEQ ID NO 92
<211> LENGTH: 42
<212> TYPE: DNA
<213> ORGANISM: Artificial Sequence
<220> FEATURE:
<223> OTHER INFORMATION: 1.5GI promoter

<400> SEQUENCE: 92
gcccttgact atgccacatc ctgagcaaat aattcaacca ct 42

<210> SEQ ID NO 93
<211> LENGTH: 39
<212> TYPE: DNA
<213> ORGANISM: artificial sequence
<220> FEATURE:
<223> OTHER INFORMATION: Primer AFBamHI

<400> SEQUENCE: 93
cattggatcc atgaataaag acacactaat acctacaac 39

<210> SEQ ID NO 94
<211> LENGTH: 39
<212> TYPE: DNA
<213> ORGANISM: artificial sequence
<220> FEATURE:
<223> OTHER INFORMATION: Primer ARAat2

<400> SEQUENCE: 94
catgacgtca ctagtgttaa caagaagtta gccggcaag 39

<210> SEQ ID NO 95
<211> LENGTH: 50
<212> TYPE: DNA
<213> ORGANISM: artificial sequence
<220> FEATURE:
<223> OTHER INFORMATION: Primer Forward 1(E)

<400> SEQUENCE: 95
catgttaaca aaggaggaaa gatctatggc gatgtttacg accaccgcaa 50

<210> SEQ ID NO 96
<211> LENGTH: 43
<212> TYPE: DNA
<213> ORGANISM: artificial sequence
<220> FEATURE:
<223> OTHER INFORMATION: Primer bottom reverse 1(E)

<400> SEQUENCE: 96
cccctccttt ggcgcgcctt actgctgggc ggcgctcggc aga 43

<210> SEQ ID NO 97
<211> LENGTH: 51
<212> TYPE: DNA
<213> ORGANISM: artificial sequence
<220> FEATURE:
<223> OTHER INFORMATION: Primer Top Forward 2(B)

<400> SEQUENCE: 97
gcccagcagt aaggcgcgcc aaaggagggg ttaaaatggt tgatttcgaa t 51

<210> SEQ ID NO 98
<211> LENGTH: 42
<212> TYPE: DNA
<213> ORGANISM: artificial sequence
<220> FEATURE:
<223> OTHER INFORMATION: Primer reverse 2(B)

<400> SEQUENCE: 98
gtcgacgtca tactagttta cacagatttt ttgaatattt gt 42

<210> SEQ ID NO 99
<211> LENGTH: 47
<212> TYPE: DNA
<213> ORGANISM: artificial sequence
<220> FEATURE:
<223> OTHER INFORMATION: Primer Pamy/lacOF

<400> SEQUENCE: 99
cattgtacag aattcgagct ctcgaggccc cgcacatacg aaaagac 47

<210> SEQ ID NO 100
<211> LENGTH: 52
<212> TYPE: DNA
<213> ORGANISM: Artificial sequence
<220> FEATURE:
<223> OTHER INFORMATION: Primer Pam/la cOR

<400> SEQUENCE: 100
cattgtacag tttaaacata ggtcaccctc attttcgtag gaattgttat cc 52

<210> SEQ ID NO 101
<211> LENGTH: 52
<212> TYPE: DNA
<213> ORGANISM: artificial sequence
<220> FEATURE:
<223> OTHER INFORMATION: Primer Spac F

<400> SEQUENCE: 101
cattgtacag tttaaacata ggtcaccctc attttcgtag gaattgttat cc 52

<210> SEQ ID NO 102
<211> LENGTH: 36
<212> TYPE: DNA
<213> ORGANISM: artificial sequence
<220> FEATURE:
<223> OTHER INFORMATION: Primer Spac R

<400> SEQUENCE: 102
catgtttaaa cggtgaccca agctggggat ccgcgg 36

<210> SEQ ID NO 103
<211> LENGTH: 44
<212> TYPE: DNA
<213> ORGANISM: artificial sequence
<220> FEATURE:
<223> OTHER INFORMATION: Primer Top TF

<400> SEQUENCE: 103
cattggtcac cattcccggg catgcaaagg aggttagtag aatg 44

<210> SEQ ID NO 104
<211> LENGTH: 51
<212> TYPE: DNA
<213> ORGANISM: artificial sequence
<220> FEATURE:
<223> OTHER INFORMATION: Primer Bot TR

<400> SEQUENCE: 104
cctttacgcg accggtacta gtcaagtcga cagggcgcgc ccaatacttt c 51

<210> SEQ ID NO 105
<211> LENGTH: 57
<212> TYPE: DNA
<213> ORGANISM: artificial sequence
<220> FEATURE:
<223> OTHER INFORMATION: Primer Top CF

<400> SEQUENCE: 105
cgcgccctgt cgacttgact agtaccggtc gcgtaaagga ggtattagtc atggaac 57

<210> SEQ ID NO 106
<211> LENGTH: 38
<212> TYPE: DNA
<213> ORGANISM: artificial sequence
<220> FEATURE:
<223> OTHER INFORMATION: Primer Bot CR

<400> SEQUENCE: 106
catcgtttaa acttggatcc agatccctta cctcctat 38

<210> SEQ ID NO 107
<211> LENGTH: 20
<212> TYPE: DNA
<213> ORGANISM: artificial sequence
<220> FEATURE:
<223> OTHER INFORMATION: Primer N3SeqF1

<400> SEQUENCE: 107
ccatcatacc atactgaccc 20

<210> SEQ ID NO 108
<211> LENGTH: 20
<212> TYPE: DNA
<213> ORGANISM: artificial sequence
<220> FEATURE:
<223> OTHER INFORMATION: Primer N3SeqF2

<400> SEQUENCE: 108
gctactggag cattgctcac 20

<210> SEQ ID NO 109
<211> LENGTH: 24
<212> TYPE: DNA

<213> ORGANISM: artificial sequence
<220> FEATURE:
<223> OTHER INFORMATION: Primer N3SeqF3

<400> SEQUENCE: 109
ccattaacag ctgctattac aggc 24

<210> SEQ ID NO 110
<211> LENGTH: 20
<212> TYPE: DNA
<213> ORGANISM: artificial sequence
<220> FEATURE:
<223> OTHER INFORMATION: Primer N4SeqR3

<400> SEQUENCE: 110
ggtctcggaa taacacctgg 20

<210> SEQ ID NO 111
<211> LENGTH: 22
<212> TYPE: DNA
<213> ORGANISM: artificial sequence
<220> FEATURE:
<223> OTHER INFORMATION: Primer N5SeqF3

<400> SEQUENCE: 111
caagcttcat aacaggagct gg 22

<210> SEQ ID NO 112
<211> LENGTH: 22
<212> TYPE: DNA
<213> ORGANISM: artificial sequence
<220> FEATURE:
<223> OTHER INFORMATION: Primer N7SeqR2

<400> SEQUENCE: 112
atcccacaat ccgtcagtga tc 22

<210> SEQ ID NO 113
<211> LENGTH: 20
<212> TYPE: DNA
<213> ORGANISM: artificial sequence
<220> FEATURE:
<223> OTHER INFORMATION: Primer N31SeqF1

<400> SEQUENCE: 113
ctgagataag aaaggccgca 20

<210> SEQ ID NO 114
<211> LENGTH: 20
<212> TYPE: DNA
<213> ORGANISM: artificial sequence
<220> FEATURE:
<223> OTHER INFORMATION: Primer N62SeqF2

<400> SEQUENCE: 114
caaccctggg cgtgtttctg 20

<210> SEQ ID NO 115
<211> LENGTH: 20
<212> TYPE: DNA
<213> ORGANISM: artificial sequence
<220> FEATURE:
<223> OTHER INFORMATION: Primer N62SeqF3

<400> SEQUENCE: 115
gtggcgaaga ttgggaactg 20

<210> SEQ ID NO 116
<211> LENGTH: 24
<212> TYPE: DNA
<213> ORGANISM: artificial sequence
<220> FEATURE:
<223> OTHER INFORMATION: Primer N62SeqF4

<400> SEQUENCE: 116
gggaaatggc agaagatgtt cagc 24

<210> SEQ ID NO 117
<211> LENGTH: 24
<212> TYPE: DNA
<213> ORGANISM: artificial sequence
<220> FEATURE:
<223> OTHER INFORMATION: Primer N63SeqR1

<400> SEQUENCE: 117
cggtctgata acctgcaaaa tcgc 24

<210> SEQ ID NO 118
<211> LENGTH: 21
<212> TYPE: DNA
<213> ORGANISM: artificial sequence
<220> FEATURE:
<223> OTHER INFORMATION: Primer N63SeqR2

<400> SEQUENCE: 118
caccagcgct ttggcaacaa c 21

<210> SEQ ID NO 119
<211> LENGTH: 23
<212> TYPE: DNA
<213> ORGANISM: artificial sequence
<220> FEATURE:
<223> OTHER INFORMATION: Primer N63SeqR3

<400> SEQUENCE: 119
gaacgtgcat acagacctgc ttc 23

<210> SEQ ID NO 120
<211> LENGTH: 20
<212> TYPE: DNA
<213> ORGANISM: artificial sequence
<220> FEATURE:
<223> OTHER INFORMATION: Primer N63SeqR4

<400> SEQUENCE: 120
cggctgaata acttttgcgg 20

<210> SEQ ID NO 121
<211> LENGTH: 24
<212> TYPE: DNA
<213> ORGANISM: artificial sequence
<220> FEATURE:
<223> OTHER INFORMATION: Primer Pamy SeqF2

<400> SEQUENCE: 121
gcctttgatg actgatgatt tggc 24

<210> SEQ ID NO 122
<211> LENGTH: 24
<212> TYPE: DNA
<213> ORGANISM: artificial sequence
<220> FEATURE:
<223> OTHER INFORMATION: Primer Pamy SeqF

<400> SEQUENCE: 122
tctccggtaa acattacggc aaac 24

<210> SEQ ID NO 123
<211> LENGTH: 24
<212> TYPE: DNA
<213> ORGANISM: artificial sequence
<220> FEATURE:
<223> OTHER INFORMATION: Primer Pamy seqR

<400> SEQUENCE: 123
cggtcagatg caattcgaca tgtg 24

<210> SEQ ID NO 124
<211> LENGTH: 20
<212> TYPE: DNA
<213> ORGANISM: artificial sequence
<220> FEATURE:
<223> OTHER INFORMATION: Primer SpacF Seq

<400> SEQUENCE: 124
gaagtggtca agacctcact 20

<210> SEQ ID NO 125
<211> LENGTH: 24
<212> TYPE: DNA
<213> ORGANISM: artificial sequence
<220> FEATURE:
<223> OTHER INFORMATION: Primer sacB Up

<400> SEQUENCE: 125
cgggtttgtt actgataaag cagg 24

<210> SEQ ID NO 126
<211> LENGTH: 24
<212> TYPE: DNA
<213> ORGANISM: artificial sequence
<220> FEATURE:
<223> OTHER INFORMATION: Primer sacB Dn

<400> SEQUENCE: 126
cggttagcca tttgcctgct ttta 24

<210> SEQ ID NO 127
<211> LENGTH: 22
<212> TYPE: DNA
<213> ORGANISM: artificial sequence
<220> FEATURE:
<223> OTHER INFORMATION: Primer HT R

<400> SEQUENCE: 127
acaaagatct ccatggacgc gt 22

<210> SEQ ID NO 128
<211> LENGTH: 1185
<212> TYPE: DNA
<213> ORGANISM: Escherichia coli

<400> SEQUENCE: 128
atgaaaaatt gtgtcatcgt cagtgcggta cgtactgcta tcggtagttt taacggttca 60
ctcgcttcca ccagcgccat cgacctgggg gcgacagtaa ttaaagccgc cattgaacgt 120
gcaaaaatcg attcacaaca cgttgatgaa gtgattatgg gtaacgtgtt acaagccggg 180
ctggggcaaa atccggcgcg tcaggcactg ttaaaaagcg ggctggcaga aacggtgtgc 240

```
ggattcacgg tcaataaagt atgtggttcg ggtcttaaaa gtgtggcgct tgccgcccag    300

gccattcagg caggtcaggc gcagagcatt gtggcggggg gtatggaaaa tatgagttta    360

gccccctact tactcgatgc aaaagcacgc tctggttatc gtcttggaga cggacaggtt    420

tatgacgtaa tcctgcgcga tggcctgatg tgcgccaccc atggttatca tatggggatt    480

accgccgaaa acgtggctaa agagtacgga attacccgtg aaatgcagga tgaactggcg    540

ctacattcac agcgtaaagc ggcagccgca attgagtccg gtgcttttac agccgaaatc    600

gtcccggtaa atgttgtcac tcgaaagaaa accttcgtct tcagtcaaga cgaattcccg    660

aaagcgaatt caacggctga agcgttaggt gcattgcgcc cggccttcga taaagcagga    720

acagtcaccg ctgggaacgc gtctggtatt aacgacggtg ctgccgctct ggtgattatg    780

gaagaatctg cggcgctggc agcaggcctt acccccctgg ctcgcattaa aagttatgcc    840

agcggtggcg tgccccccgc attgatgggt atggggccag tacctgccac gcaaaaagcg    900

ttacaactgg cggggctgca actggcggat attgatctca ttgaggctaa tgaagcattt    960

gctgcacagt tccttgccgt tgggaaaaac ctgggctttg attctgagaa agtgaatgtc   1020

aacggcgggg ccatcgcgct cggtcatcct atcggtgcca gtggtgctcg tattctggtc   1080

acactattac atgccatgca ggcacgcgat aaaacgctgg ggctggcaac actgtgcatt   1140

ggcggcggtc agggaattgc gatggtgatt gaacggttga attaa                   1185
```

<210> SEQ ID NO 129
<211> LENGTH: 394
<212> TYPE: PRT
<213> ORGANISM: Escherichia coli

<400> SEQUENCE: 129

```
Met Lys Asn Cys Val Ile Val Ser Ala Val Arg Thr Ala Ile Gly Ser
1               5                   10                  15

Phe Asn Gly Ser Leu Ala Ser Thr Ser Ala Ile Asp Leu Gly Ala Thr
            20                  25                  30

Val Ile Lys Ala Ala Ile Glu Arg Ala Lys Ile Asp Ser Gln His Val
        35                  40                  45

Asp Glu Val Ile Met Gly Asn Val Leu Gln Ala Gly Leu Gly Gln Asn
    50                  55                  60

Pro Ala Arg Gln Ala Leu Leu Lys Ser Gly Leu Ala Glu Thr Val Cys
65                  70                  75                  80

Gly Phe Thr Val Asn Lys Val Cys Gly Ser Gly Leu Lys Ser Val Ala
                85                  90                  95

Leu Ala Ala Gln Ala Ile Gln Ala Gly Gln Ala Gln Ser Ile Val Ala
            100                 105                 110

Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
    130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ala Ile Glu
            180                 185                 190

Ser Gly Ala Phe Thr Ala Glu Ile Val Pro Val Asn Val Val Thr Arg
        195                 200                 205

Lys Lys Thr Phe Val Phe Ser Gln Asp Glu Phe Pro Lys Ala Asn Ser
```

```
    210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Ala Leu Ala Ala Gly Leu Thr Pro
            260                 265                 270

Leu Ala Arg Ile Lys Ser Tyr Ala Ser Gly Gly Val Pro Pro Ala Leu
        275                 280                 285

Met Gly Met Gly Pro Val Pro Ala Thr Gln Lys Ala Leu Gln Leu Ala
    290                 295                 300

Gly Leu Gln Leu Ala Asp Ile Asp Leu Ile Glu Ala Asn Glu Ala Phe
305                 310                 315                 320

Ala Ala Gln Phe Leu Ala Val Gly Lys Asn Leu Gly Phe Asp Ser Glu
                325                 330                 335

Lys Val Asn Val Asn Gly Gly Ala Ile Ala Leu Gly His Pro Ile Gly
            340                 345                 350

Ala Ser Gly Ala Arg Ile Leu Val Thr Leu Leu His Ala Met Gln Ala
        355                 360                 365

Arg Asp Lys Thr Leu Gly Leu Ala Thr Leu Cys Ile Gly Gly Gly Gln
    370                 375                 380

Gly Ile Ala Met Val Ile Glu Arg Leu Asn
385                 390


<210> SEQ ID NO 130
<211> LENGTH: 1182
<212> TYPE: DNA
<213> ORGANISM: Bacillus subtilis

<400> SEQUENCE: 130

ttaatgaacc tgcactaaga cggcgtctcc ctgtgctgcc ccgctgcaaa tagcggcaac     60

gcccagaccc cctccccgtc gctttaattc ataaacaagc gtcatgagaa ttctcgcacc    120

gctcgcgccg atcgggtggc cgagcgcgat cgcaccgcca ttcacattta ctttttcaag    180

atcgaaacct acgatttttt cacatgtcaa aacaactgaa gcaaaagctt catttacttc    240

aaacaagtca atatcttgga cagttaaacc attcttttc aggagcttgt taatagcaaa    300

ccctggcgct gccgccagct cgtgcgctgg cattcccgta gttgaaaaac caagaattgt    360

agccagaggc cgtttgccaa gctcagcagc tttttcctca gacatcagca cgaacgcgcc    420

ggctccgtca ttgactccag gagcattgcc ggctgtgata gaaccgtcac ttgcataaat    480

cggagcaagt tttgcgagct gatccagact tgtgtcacgg cgaatcgctt catctttatc    540

aacaacgttt ggttttcctt ttcgaccgat ccagttgacg ggaacaattt catcctgaaa    600

cttcccttca tcggcggcct tagctgccct tgcatgactt ctcaacgccc attcgtcctg    660

ctctcttcgt gagattgcat attccttggc agctgtattt ccgtgaacag ccatgtgcac    720

ctcgtcaaat gcgcacgtta atccgtcata caccattaag tccctaagct cgccgtcccc    780

catccgtgct ccccagcgcc cggcgggaac ggcatacgga atattgctca tgctttccat    840

cccccccgca acaagtatgt ccgcatcctg cgcccgaatc atttgatcac ataaagtgac    900

agcgcgaagg ccggaagcac agactttatt cagtgtttct gacggcacac tccaaggcat    960

tcccgccaga cgggcagctt gacgggaagg tatctgccct gagccggcct ggacaaccat   1020

gcccatgacg tttccttcta catcatctcc agagactcca gcctgttgca gcgcctcctt   1080

catcacaatg cccccaagct cagcagcttt cacctctttc aaaactccgc cgaatttgcc   1140
```

```
aaatggagtt cttgcagcac ttacaatgac tgttttcctc at                    1182


<210> SEQ ID NO 131
<211> LENGTH: 393
<212> TYPE: PRT
<213> ORGANISM: Bacillus subtilis

<400> SEQUENCE: 131

Met Arg Lys Thr Val Ile Val Ser Ala Ala Arg Thr Pro Phe Gly Lys
1               5                   10                  15

Phe Gly Gly Val Leu Lys Glu Val Lys Ala Ala Glu Leu Gly Gly Ile
            20                  25                  30

Val Met Lys Glu Ala Leu Gln Gln Ala Gly Val Ser Gly Asp Asp Val
        35                  40                  45

Glu Gly Asn Val Met Gly Met Val Val Gln Ala Gly Ser Gly Gln Ile
    50                  55                  60

Pro Ser Arg Gln Ala Ala Arg Leu Ala Gly Met Pro Trp Ser Val Pro
65                  70                  75                  80

Ser Glu Thr Leu Asn Lys Val Cys Ala Ser Gly Leu Arg Ala Val Thr
                85                  90                  95

Leu Cys Asp Gln Met Ile Arg Ala Gln Asp Ala Asp Ile Leu Val Ala
            100                 105                 110

Gly Gly Met Glu Ser Met Ser Asn Ile Pro Tyr Ala Val Pro Ala Gly
        115                 120                 125

Arg Trp Gly Ala Arg Met Gly Asp Gly Glu Leu Arg Asp Leu Met Val
    130                 135                 140

Tyr Asp Gly Leu Thr Cys Ala Phe Asp Glu Val His Met Ala Val His
145                 150                 155                 160

Gly Asn Thr Ala Ala Lys Glu Tyr Ala Ile Ser Arg Arg Glu Gln Asp
                165                 170                 175

Glu Trp Ala Leu Arg Ser His Ala Arg Ala Ala Lys Ala Ala Asp Glu
            180                 185                 190

Gly Lys Phe Gln Asp Glu Ile Val Pro Val Asn Trp Ile Gly Arg Lys
        195                 200                 205

Gly Lys Pro Asn Val Val Asp Lys Asp Glu Ala Ile Arg Arg Asp Thr
    210                 215                 220

Ser Leu Asp Gln Leu Ala Lys Leu Ala Pro Ile Tyr Ala Ser Asp Gly
225                 230                 235                 240

Ser Ile Thr Ala Gly Asn Ala Pro Gly Val Asn Asp Gly Ala Gly Ala
                245                 250                 255

Phe Val Leu Met Ser Glu Glu Lys Ala Ala Glu Leu Gly Lys Arg Pro
            260                 265                 270

Leu Ala Thr Ile Leu Gly Phe Ser Thr Thr Gly Met Pro Ala His Glu
        275                 280                 285

Leu Ala Ala Ala Pro Gly Phe Ala Ile Asn Lys Leu Leu Lys Lys Asn
    290                 295                 300

Gly Leu Thr Val Gln Asp Ile Asp Leu Phe Glu Val Asn Glu Ala Phe
305                 310                 315                 320

Ala Ser Val Val Leu Thr Cys Glu Lys Ile Val Gly Phe Asp Leu Glu
                325                 330                 335

Lys Val Asn Val Asn Gly Gly Ala Ile Ala Leu Gly His Pro Ile Gly
            340                 345                 350

Ala Ser Gly Ala Arg Ile Leu Met Thr Leu Val Tyr Glu Leu Lys Arg
        355                 360                 365
```

```
Arg Gly Gly Gly Leu Gly Val Ala Ala Ile Cys Ser Gly Ala Ala Gln
    370                 375                 380

Gly Asp Ala Val Leu Val Gln Val His
385                 390


<210> SEQ ID NO 132
<211> LENGTH: 1197
<212> TYPE: DNA
<213> ORGANISM: Saccharomyces cerevisiae

<400> SEQUENCE: 132

atgtctcaga acgtttacat tgtatcgact gccagaaccc caattggttc attccagggt     60

tctctatcct ccaagacagc agtggaattg ggtgctgttg ctttaaaagg cgccttggct    120

aaggttccag aattggatgc atccaaggat tttgacgaaa ttatttttgg taacgttctt    180

tctgccaatt tgggccaagc tccggccaga caagttgctt tggctgccgg tttgagtaat    240

catatcgttg caagcacagt taacaaggtc tgtgcatccg ctatgaaggc aatcattttg    300

ggtgctcaat ccatcaaatg tggtaatgct gatgttgtcg tagctggtgg ttgtgaatct    360

atgactaacg caccatacta catgccagca gcccgtgcgg gtgccaaatt tggccaaact    420

gttcttgttg atggtgtcga aagagatggg ttgaacgatg cgtacgatgg tctagccatg    480

ggtgtacacg cagaaaagtg tgcccgtgat tgggatatta ctagagaaca acaagacaat    540

tttgccatcg aatcctacca aaaatctcaa aaatctcaaa aggaaggtaa attcgacaat    600

gaaattgtac ctgttaccat taagggattt agaggtaagc ctgatactca agtcacgaag    660

gacgaggaac ctgctagatt acacgttgaa aaattgagat ctgcaaggac tgttttccaa    720

aaagaaaacg gtactgttac tgccgctaac gcttctccaa tcaacgatgg tgctgcagcc    780

gtcatcttgg tttccgaaaa agttttgaag gaaaagaatt tgaagccttt ggctattatc    840

aaaggttggg gtgaggccgc tcatcaacca gctgatttta catgggctcc atctcttgca    900

gttccaaagg ctttgaaaca tgctggcatc gaagacatca attctgttga ttactttgaa    960

ttcaatgaag ccttttcggt tgtcggtttg gtgaacacta agatttttgaa gctagaccca   1020

tctaaggtta atgtatatgg tggtgctgtt gctctaggtc acccattggg ttgttctggt   1080

gctagagtgg ttgttacact gctatccatc ttacagcaag aaggaggtaa gatcggtgtt   1140

gccgccattt gtaatggtgg tggtggtgct tcctctattg tcattgaaaa gatatga       1197


<210> SEQ ID NO 133
<211> LENGTH: 398
<212> TYPE: PRT
<213> ORGANISM: Saccharomyces cerevisiae

<400> SEQUENCE: 133

Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95
```

```
Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Val Thr Leu Leu
        355                 360                 365

Ser Ile Leu Gln Gln Glu Gly Gly Lys Ile Gly Val Ala Ala Ile Cys
    370                 375                 380

Asn Gly Gly Gly Gly Ala Ser Ser Ile Val Ile Glu Lys Ile
385                 390                 395


<210> SEQ ID NO 134
<211> LENGTH: 864
<212> TYPE: DNA
<213> ORGANISM: Bacillus subtilis

<400> SEQUENCE: 134

atggaaatca aacaaatcat ggtagctggc gcaggtcaga tggggagcgg aattgctcaa      60

acagccgccg acgcgggctt ttatgtgcgg atgtatgatg tgaatccaga ggccgcggag     120

gcaggattga aacggctgaa gaaacagctg gcccgtgatg ctgagaaagg aaaaaggacc     180

gagacggaag tgaagagcgt aatcaaccgc atttcgattt ctcaaacact tgaggaggca     240

gagcatgcgg acattgtgat tgaggctatc gcagaaaaca tggcggcaaa aactgagatg     300

tttaaaacac ttgatcgcat ttgcccgcct catacgattt tggccagcaa tacatcttcc     360

ttgcctatta cagaaatcgc tgctgtaaca aaccggcctc aacgggttat tggcatgcat     420

tttatgaatc ccgtccctgt aatgaagctg gtagaagtga ttcgaggctt ggctacatca     480
```

```
gaagaaacgg ccttagatgt tatggcatta gcggaaaaga tggggaaaac agcggtagaa    540

gtcaatgatt ttcctgggtt tgtttccaac cgtgtgcttc ttccaatgat taatgaagcc    600

atctattgcg tgtatgaggg agtggcgaag ccggaggcaa tagatgaagt gatgaagctg    660

ggcatgaatc atccgatggg tccgcttgca ttagcggatt ttatcggact ggatacgtgt    720

ttatcaatta tggaagtcct tcactcaggc cttggcgatt ccaaataccg tccttgcccg    780

ctgctccgca agtatgtcaa agcaggctgg cttggcaaaa agagcggacg cggtttttat    840

gactatgagg agaagacttc ctga                                            864
```

<210> SEQ ID NO 135
<211> LENGTH: 287
<212> TYPE: PRT
<213> ORGANISM: Bacillus subtilis

<400> SEQUENCE: 135

```
Met Glu Ile Lys Gln Ile Met Val Ala Gly Ala Gly Gln Met Gly Ser
1               5                   10                  15

Gly Ile Ala Gln Thr Ala Ala Asp Ala Gly Phe Tyr Val Arg Met Tyr
            20                  25                  30

Asp Val Asn Pro Glu Ala Ala Glu Ala Gly Leu Lys Arg Leu Lys Lys
        35                  40                  45

Gln Leu Ala Arg Asp Ala Glu Lys Gly Lys Arg Thr Glu Thr Glu Val
    50                  55                  60

Lys Ser Val Ile Asn Arg Ile Ser Ile Ser Gln Thr Leu Glu Glu Ala
65                  70                  75                  80

Glu His Ala Asp Ile Val Ile Glu Ala Ile Ala Glu Asn Met Ala Ala
                85                  90                  95

Lys Thr Glu Met Phe Lys Thr Leu Asp Arg Ile Cys Pro Pro His Thr
            100                 105                 110

Ile Leu Ala Ser Asn Thr Ser Ser Leu Pro Ile Thr Glu Ile Ala Ala
        115                 120                 125

Val Thr Asn Arg Pro Gln Arg Val Ile Gly Met His Phe Met Asn Pro
    130                 135                 140

Val Pro Val Met Lys Leu Val Glu Val Ile Arg Gly Leu Ala Thr Ser
145                 150                 155                 160

Glu Glu Thr Ala Leu Asp Val Met Ala Leu Ala Glu Lys Met Gly Lys
                165                 170                 175

Thr Ala Val Glu Val Asn Asp Phe Pro Gly Phe Val Ser Asn Arg Val
            180                 185                 190

Leu Leu Pro Met Ile Asn Glu Ala Ile Tyr Cys Val Tyr Glu Gly Val
        195                 200                 205

Ala Lys Pro Glu Ala Ile Asp Glu Val Met Lys Leu Gly Met Asn His
    210                 215                 220

Pro Met Gly Pro Leu Ala Leu Ala Asp Phe Ile Gly Leu Asp Thr Cys
225                 230                 235                 240

Leu Ser Ile Met Glu Val Leu His Ser Gly Leu Gly Asp Ser Lys Tyr
                245                 250                 255

Arg Pro Cys Pro Leu Leu Arg Lys Tyr Val Lys Ala Gly Trp Leu Gly
            260                 265                 270

Lys Lys Ser Gly Arg Gly Phe Tyr Asp Tyr Glu Glu Lys Thr Ser
        275                 280                 285
```

<210> SEQ ID NO 136
<211> LENGTH: 855

<212> TYPE: DNA
<213> ORGANISM: Ralstonia eutropha

<400> SEQUENCE: 136

```
atggcaatca ggacagtggg catcgtgggt gccggcacca tgggcaacgg catcgcgcag     60
gcttgtgcgg tggtgggcct ggacgtggtg atggtggata tcagcgacgc agcggtgcag    120
aagggcatcg ccaccgtcgc cggcagcctg gaccgcctga tcaagaagga caagatcagc    180
gaagccgaca agatgactgc gctcgcgcgc atccacggca gcaccgcgta tgacgacctg    240
aagaaggccg atatcgtgat cgaggccgcc accgagaact ttgacctgaa ggtcaagatc    300
ctcaagcaga tcgacagcat cgtcggcgag aacgtcatca ttgcttcgaa cacgtcgtcg    360
atctcgatca ccaagctggc cgccgtgacg agtcgccccg agcgcttcat cggcatgcac    420
ttcttcaacc cggtgccggt gatggcgctg gtggaactga tccgcggcct gcagaccagc    480
gacgcggctc acgccgatgt cgaggcgctg gccaaggaac tgggcaagta cccgatcacc    540
gtcaagaaca gcccgggctt cgtcgtcaac cgcatcctgt gcccgatgat caacgaagcc    600
ttctgcgtgc tcggtgaagg cctggcctcg ccggaagaga tcgacgaagg catgaagctc    660
ggctgcaacc atccgatcgg cccccctggca ctggccgaca tgatcggcct ggacaccatg    720
ctggcagtga tggaagtgct gtacacagaa tttgccgacc cgaagtatcg tccggccatg    780
ctgatgcgcg agatggtggc tgcggggtat ctgggccgca agactggccg tggcgtgtac    840
gtctacagca agtaa                                                     855
```

<210> SEQ ID NO 137
<211> LENGTH: 284
<212> TYPE: PRT
<213> ORGANISM: Ralstonia eutropha

<400> SEQUENCE: 137

```
Met Ala Ile Arg Thr Val Gly Ile Val Gly Ala Gly Thr Met Gly Asn
1               5                   10                  15

Gly Ile Ala Gln Ala Cys Ala Val Val Gly Leu Asp Val Val Met Val
            20                  25                  30

Asp Ile Ser Asp Ala Ala Val Gln Lys Gly Ile Ala Thr Val Ala Gly
        35                  40                  45

Ser Leu Asp Arg Leu Ile Lys Lys Asp Lys Ile Ser Glu Ala Asp Lys
    50                  55                  60

Met Thr Ala Leu Ala Arg Ile His Gly Ser Thr Ala Tyr Asp Asp Leu
65                  70                  75                  80

Lys Lys Ala Asp Ile Val Ile Glu Ala Ala Thr Glu Asn Phe Asp Leu
                85                  90                  95

Lys Val Lys Ile Leu Lys Gln Ile Asp Ser Ile Val Gly Glu Asn Val
            100                 105                 110

Ile Ile Ala Ser Asn Thr Ser Ser Ile Ser Ile Thr Lys Leu Ala Ala
        115                 120                 125

Val Thr Ser Arg Pro Glu Arg Phe Ile Gly Met His Phe Phe Asn Pro
    130                 135                 140

Val Pro Val Met Ala Leu Val Glu Leu Ile Arg Gly Leu Gln Thr Ser
145                 150                 155                 160

Asp Ala Ala His Ala Asp Val Glu Ala Leu Ala Lys Glu Leu Gly Lys
                165                 170                 175

Tyr Pro Ile Thr Val Lys Asn Ser Pro Gly Phe Val Val Asn Arg Ile
            180                 185                 190

Leu Cys Pro Met Ile Asn Glu Ala Phe Cys Val Leu Gly Glu Gly Leu
```

```
        195                 200                 205

Ala Ser Pro Glu Glu Ile Asp Glu Gly Met Lys Leu Gly Cys Asn His
    210                 215                 220

Pro Ile Gly Pro Leu Ala Leu Ala Asp Met Ile Gly Leu Asp Thr Met
225                 230                 235                 240

Leu Ala Val Met Glu Val Leu Tyr Thr Glu Phe Ala Asp Pro Lys Tyr
                245                 250                 255

Arg Pro Ala Met Leu Met Arg Glu Met Val Ala Ala Gly Tyr Leu Gly
            260                 265                 270

Arg Lys Thr Gly Arg Gly Val Tyr Val Tyr Ser Lys
        275                 280


<210> SEQ ID NO 138
<211> LENGTH: 741
<212> TYPE: DNA
<213> ORGANISM: Alcaligenes eutrophis

<400> SEQUENCE: 138

atgactcagc gcattgcgta tgtgaccggc ggcatgggtg gtatcggaac cgccatttgc     60

cagcggctgg ccaaggatgg ctttcgtgtg gtggccggtt gcggccccaa ctcgccgcgc    120

cgcgaaaagt ggctggagca gcagaaggcc ctgggcttcg atttcattgc ctcggaaggc    180

aatgtggctg actgggactc gaccaagacc gcattcgaca aggtcaagtc cgaggtcggc    240

gaggttgatg tgctgatcaa caacgccggt atcacccgcg acgtggtgtt ccgcaagatg    300

acccgcgccg actgggatgc ggtgatcgac accaacctga cctcgctgtt caacgtcacc    360

aagcaggtga tcgacggcat ggccgaccgt ggctggggcc gcatcgtcaa catctcgtcg    420

gtgaacgggc agaagggcca gttcggccag accaactact ccaccgccaa ggccggcctg    480

catggcttca ccatggcact ggcgcaggaa gtggcgacca agggcgtgac cgtcaacacg    540

gtctctccgg gctatatcgc caccgacatg gtcaaggcga tccgccagga cgtgctcgac    600

aagatcgtcg cgacgatccc ggtcaagcgc ctgggcctgc cggaagagat cgcctcgatc    660

tgcgcctggt tgtcgtcgga ggagtccggt ttctcgaccg gcgccgactt ctcgctcaac    720

ggcggcctgc atatgggctg a                                               741


<210> SEQ ID NO 139
<211> LENGTH: 246
<212> TYPE: PRT
<213> ORGANISM: Alcaligenes eutrophus

<400> SEQUENCE: 139

Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
            20                  25                  30

Gly Cys Gly Pro Asn Ser Pro Arg Arg Glu Lys Trp Leu Glu Gln Gln
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110
```

```
Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240

Gly Gly Leu His Met Gly
                245


<210> SEQ ID NO 140
<211> LENGTH: 768
<212> TYPE: DNA
<213> ORGANISM: Escherichia coli

<400> SEQUENCE: 140

atgagcgaac tgatcgtcag ccgtcagcaa cgagtattgt tgctgaccct taaccgtccc      60

gccgcacgta atgcgctaaa taatgccctg ctgatgcaac tggtaaatga actggaagct     120

gcggctaccg ataccagcat ttcggtctgt gtgattaccg gtaatgcacg ctttttttgcc    180

gctggggccg atctcaacga aatggcagaa aaagatctcg cggccacctt aaacgataca     240

cgtccgcagc tatgggcgcg attgcaggcc tttaataaac cacttatcgc agccgtcaat     300

ggttacgcgc ttggggcggg ttgcgaactg gcattgttgt gcgatgtggt ggttgccgga     360

gagaacgcgc gttttgggtt gccggaaatc actctcggca tcatgcctgg cgcaggcgga     420

acgcaacgtt taatccgtag tgtcggtaaa tcgttagcca gcaaaatggt gctgagcgga     480

gaaagtatca ccgctcagca agcacagcag gccgggctgg ttagcgacgt cttccccagc     540

gatttaaccc tcgaatacgc cttacagctg gcatcgaaaa tggcacgtca ctcgccgctg     600

gccttacaag cggcaaagca agcgctgcgc cagtcgcagg aagtggcttt gcaagccgga     660

cttgcccagg agcgacagtt attcaccttg ctggcggcaa cagaagatcg tcatgaaggc     720

atctccgctt tcttacaaaa acgcacgccc gactttaaag gacgctaa                  768


<210> SEQ ID NO 141
<211> LENGTH: 255
<212> TYPE: PRT
<213> ORGANISM: Escherichia coli

<400> SEQUENCE: 141

Met Ser Glu Leu Ile Val Ser Arg Gln Gln Arg Val Leu Leu Leu Thr
1               5                   10                  15

Leu Asn Arg Pro Ala Ala Arg Asn Ala Leu Asn Asn Ala Leu Leu Met
            20                  25                  30

Gln Leu Val Asn Glu Leu Glu Ala Ala Ala Thr Asp Thr Ser Ile Ser
        35                  40                  45

Val Cys Val Ile Thr Gly Asn Ala Arg Phe Phe Ala Ala Gly Ala Asp
    50                  55                  60
```

```
Leu Asn Glu Met Ala Glu Lys Asp Leu Ala Ala Thr Leu Asn Asp Thr
65                  70                  75                  80

Arg Pro Gln Leu Trp Ala Arg Leu Gln Ala Phe Asn Lys Pro Leu Ile
                85                  90                  95

Ala Ala Val Asn Gly Tyr Ala Leu Gly Ala Gly Cys Glu Leu Ala Leu
            100                 105                 110

Leu Cys Asp Val Val Val Ala Gly Glu Asn Ala Arg Phe Gly Leu Pro
        115                 120                 125

Glu Ile Thr Leu Gly Ile Met Pro Gly Ala Gly Gly Thr Gln Arg Leu
    130                 135                 140

Ile Arg Ser Val Gly Lys Ser Leu Ala Ser Lys Met Val Leu Ser Gly
145                 150                 155                 160

Glu Ser Ile Thr Ala Gln Gln Ala Gln Gln Ala Gly Leu Val Ser Asp
                165                 170                 175

Val Phe Pro Ser Asp Leu Thr Leu Glu Tyr Ala Leu Gln Leu Ala Ser
            180                 185                 190

Lys Met Ala Arg His Ser Pro Leu Ala Leu Gln Ala Ala Lys Gln Ala
        195                 200                 205

Leu Arg Gln Ser Gln Glu Val Ala Leu Gln Ala Gly Leu Ala Gln Glu
    210                 215                 220

Arg Gln Leu Phe Thr Leu Leu Ala Ala Thr Glu Asp Arg His Glu Gly
225                 230                 235                 240

Ile Ser Ala Phe Leu Gln Lys Arg Thr Pro Asp Phe Lys Gly Arg
                245                 250                 255

<210> SEQ ID NO 142
<211> LENGTH: 783
<212> TYPE: DNA
<213> ORGANISM: Bacillus subtilis

<400> SEQUENCE: 142

atgggagatt ctattctttt tactgttaaa aatgaacata tggcgttgat caccttaaac     60

aggcctcagg cagcaaatgc tctttcagcg gaaatgctta gaaacctgca aatgattatc    120

caggaaattg aatttaactc aaacatccgt tgcgtcatcc tcacaggcac cggtgaaaaa    180

gcgttttgtg caggggcaga cctgaaggaa cggataaaac tgaaagaaga tcaggttctg    240

gaaagtgtat ctctcattca aagaacggcg gctttacttg atgccttgcc gcagccggtc    300

atagctgcga taaatggaag cgcattaggc ggcggactag aattggcatt ggcatgcgac    360

cttcgaatcg caactgaagc agctgtgctg ggacttccgg aaacagggtt agctattatc    420

ccgggcgctg gagggaccca aaggctgccc cggctgattg gcagaggaaa agcaaaagaa    480

ttcatttata caggcagacg cgtgaccgca cacgaagcaa aagaaatcgg ccttgtagag    540

catgtcacgg ctccttgtga ccttatgcca aaagcagagg aactggccgc agccatttct    600

gccaacggac cgatcgctgt ccgtcaggct aaatttgcaa tcaataaagg attggagaca    660

gatcttgcta caggccttgc gattgaacaa aaagcgtatg aacaaaccat cccgacaaaa    720

gacaggagag aagggcttca ggcctttcaa gaaaaaagac gggccgtata caagggaata    780

taa                                                                  783

<210> SEQ ID NO 143
<211> LENGTH: 260
<212> TYPE: PRT
<213> ORGANISM: Bacillus subtilis

<400> SEQUENCE: 143
```

```
Met Gly Asp Ser Ile Leu Phe Thr Val Lys Asn Glu His Met Ala Leu
1               5                   10                  15

Ile Thr Leu Asn Arg Pro Gln Ala Ala Asn Ala Leu Ser Ala Glu Met
            20                  25                  30

Leu Arg Asn Leu Gln Met Ile Ile Gln Glu Ile Glu Phe Asn Ser Asn
        35                  40                  45

Ile Arg Cys Val Ile Leu Thr Gly Thr Gly Glu Lys Ala Phe Cys Ala
    50                  55                  60

Gly Ala Asp Leu Lys Glu Arg Ile Lys Leu Lys Glu Asp Gln Val Leu
65                  70                  75                  80

Glu Ser Val Ser Leu Ile Gln Arg Thr Ala Ala Leu Leu Asp Ala Leu
                85                  90                  95

Pro Gln Pro Val Ile Ala Ala Ile Asn Gly Ser Ala Leu Gly Gly Gly
            100                 105                 110

Leu Glu Leu Ala Leu Ala Cys Asp Leu Arg Ile Ala Thr Glu Ala Ala
        115                 120                 125

Val Leu Gly Leu Pro Glu Thr Gly Leu Ala Ile Ile Pro Gly Ala Gly
    130                 135                 140

Gly Thr Gln Arg Leu Pro Arg Leu Ile Gly Arg Gly Lys Ala Lys Glu
145                 150                 155                 160

Phe Ile Tyr Thr Gly Arg Arg Val Thr Ala His Glu Ala Lys Glu Ile
                165                 170                 175

Gly Leu Val Glu His Val Thr Ala Pro Cys Asp Leu Met Pro Lys Ala
            180                 185                 190

Glu Glu Leu Ala Ala Ala Ile Ser Ala Asn Gly Pro Ile Ala Val Arg
        195                 200                 205

Gln Ala Lys Phe Ala Ile Asn Lys Gly Leu Glu Thr Asp Leu Ala Thr
    210                 215                 220

Gly Leu Ala Ile Glu Gln Lys Ala Tyr Glu Gln Thr Ile Pro Thr Lys
225                 230                 235                 240

Asp Arg Arg Glu Gly Leu Gln Ala Phe Gln Glu Lys Arg Arg Ala Val
                245                 250                 255

Tyr Lys Gly Ile
            260
```

<210> SEQ ID NO 144
<211> LENGTH: 405
<212> TYPE: DNA
<213> ORGANISM: Aeromonas caviae

<400> SEQUENCE: 144

```
atgagcgcac aatccctgga agtaggccag aaggcccgtc tcagcaagcg gttcggggcg      60

gcggaggtag ccgccttcgc cgcgctctcg gaggacttca accccctgca cctggacccg     120

gccttcgccg ccaccacggc gttcgagcgg cccatagtcc acggcatgct gctcgccagc     180

ctcttctccg ggctgctggg ccagcagttg ccgggcaagg ggagcatcta tctgggtcaa     240

agcctcagct tcaagctgcc ggtctttgtc ggggacgagg tgacggccga ggtggaggtg     300

accgcccttc gcgaggacaa gcccatcgcc accctgacca cccgcatctt cacccaaggc     360

ggcgccctcg ccgtgacggg ggaagccgtg gtcaagctgc cttaa                     405
```

<210> SEQ ID NO 145
<211> LENGTH: 134
<212> TYPE: PRT
<213> ORGANISM: Aeromonas caviae

<400> SEQUENCE: 145

```
Met Ser Ala Gln Ser Leu Glu Val Gly Gln Lys Ala Arg Leu Ser Lys
1               5                   10                  15

Arg Phe Gly Ala Ala Glu Val Ala Ala Phe Ala Ala Leu Ser Glu Asp
            20                  25                  30

Phe Asn Pro Leu His Leu Asp Pro Ala Phe Ala Ala Thr Thr Ala Phe
        35                  40                  45

Glu Arg Pro Ile Val His Gly Met Leu Leu Ala Ser Leu Phe Ser Gly
    50                  55                  60

Leu Leu Gly Gln Gln Leu Pro Gly Lys Gly Ser Ile Tyr Leu Gly Gln
65                  70                  75                  80

Ser Leu Ser Phe Lys Leu Pro Val Phe Val Gly Asp Glu Val Thr Ala
                85                  90                  95

Glu Val Glu Val Thr Ala Leu Arg Glu Asp Lys Pro Ile Ala Thr Leu
            100                 105                 110

Thr Thr Arg Ile Phe Thr Gln Gly Gly Ala Leu Ala Val Thr Gly Glu
        115                 120                 125

Ala Val Val Lys Leu Pro
    130
```

<210> SEQ ID NO 146
<211> LENGTH: 1912
<212> TYPE: DNA
<213> ORGANISM: Euglena gracilis

<400> SEQUENCE: 146

```
ttttcgcccg tgcaccacga tgtcgtgccc cgcctcgccg tctgctgccg tggtgtctgc      60

cggcgccctc tgcctgtgcg tggcaacggt attgttggcg actggatcca accccaccgc     120

cctgtccact gcttccactc gctctccgac ctcactggtc cgtggggtgg acaggggctt     180

gatgaggcca accactgcag cggctctgac gacaatgaga gaggtgcccc agatggctga     240

gggattttca ggcgaagcca cgtctgcatg ggccgccgcg gggccgcagt gggcggcgcc     300

gctcgtggcc gcggcctcct ccgcactggc gctgtggtgg tgggccgccc ggcgcagcgt     360

gcggcggccg ctggcagcgc tggcggagct gcccaccgcg gtcacccacc tggccccccc     420

gatggcgatg ttcaccacca cagcgaaggt catccagccc aagattcgtg gcttcatctg     480

cacgaccacc cacccgatcg gctgtgagaa gcgggtccag gaggagatcg cgtacgcccg     540

tgcccacccg cccaccagcc ctggcccgaa gagggtgctg gtcatcggct gcagtaccgg     600

ctacgggctc tccacccgca tcaccgctgc cttcggctac caggccgcca cgctgggcgt     660

gttcctggcg ggcccccega cgaagggccg ccccgccgcg gcgggctggt acaacaccgt     720

ggcgttcgag aaggccgccc tggaggccgg gctgtacgcc cggagcctta atggcgacgc     780

cttcgactcc acaacgaagg cgcggacggt cgaggcgatc aagcgggacc tcggcacggt     840

ggacctcgtg gtgtacagca tcgccgcccc gaagcggacg gaccctgcca ccggcgtcct     900

ccacaaggcc tgcctgaagc ccatcggcgc cacgtacacc aaccgcactg tgaacaccga     960

caaggcggag gtgaccgacg tcagcattga gccggcctcc cccgaagaga tcgcggacac    1020

ggtgaaggtg atgggcgggg aggactggga gctctggatc caggcgctgt cggaggccgg    1080

cgtgctggcg gagggggcca agacggtggc gtactcctac atcggccccg agatgacgtg    1140

gcctgtctac tggtccggca ccatcgggga ggccaagaag gacgtggaga aggctgccaa    1200

gcgcatcacg cagcagtacg gctgcccggc gtacccggtg gtggccaagg ccttggtcac    1260

ccaggccagc tccgccatcc cggtggtgcc gctctacatc tgcctgctgt accgcgttat    1320
```

```
gaaggagaag ggcacccacg agggctgcat cgagcagatg gtgcggctgc tcaccacgaa   1380

gctgtacccc gagaacgggg cccccatcgt cgatgaggcc ggacgtgtgc gggtggatga   1440

ctgggagatg gcggaggatg tgcagcaggc tgttaaggac ctctggagcc aggtgagcac   1500

tgccaacctc aaggacatct ccgacttcgc tgggtatcaa actgagttcc tgcggctgtt   1560

cgggttcggc attgacggcg tggactacga ccagcccgtg gacgtggagg cggacctccc   1620

cagtgctgcc cagcagtagg tgctggacgc cgcctctctc cggggggtct gccaaaatgg   1680

tcgctccccc aacccaaccc cctgcccacc atcggggtcc cgcgggtgaa tgcggccccc   1740

acccaaaggc aaaggtcaag gccggggccc caccgccaaa gggtaacaca tatgtatccg   1800

tcgggggctg atccgcgtgc gacacgggcc ataattgtgc cccacgggat gtccatgcgc   1860

ctaagacaac tgccccggcc gacagtcgct accgccttga gttccccagg ca           1912


<210> SEQ ID NO 147
<211> LENGTH: 539
<212> TYPE: PRT
<213> ORGANISM: Euglena gracilis

<400> SEQUENCE: 147

Met Ser Cys Pro Ala Ser Pro Ser Ala Ala Val Val Ser Ala Gly Ala
1               5                   10                  15

Leu Cys Leu Cys Val Ala Thr Val Leu Leu Ala Thr Gly Ser Asn Pro
            20                  25                  30

Thr Ala Leu Ser Thr Ala Ser Thr Arg Ser Pro Thr Ser Leu Val Arg
        35                  40                  45

Gly Val Asp Arg Gly Leu Met Arg Pro Thr Thr Ala Ala Ala Leu Thr
    50                  55                  60

Thr Met Arg Glu Val Pro Gln Met Ala Glu Gly Phe Ser Gly Glu Ala
65                  70                  75                  80

Thr Ser Ala Trp Ala Ala Ala Gly Pro Gln Trp Ala Ala Pro Leu Val
                85                  90                  95

Ala Ala Ala Ser Ser Ala Leu Ala Leu Trp Trp Trp Ala Ala Arg Arg
            100                 105                 110

Ser Val Arg Arg Pro Leu Ala Ala Leu Ala Glu Leu Pro Thr Ala Val
        115                 120                 125

Thr His Leu Ala Pro Pro Met Ala Met Phe Thr Thr Thr Ala Lys Val
    130                 135                 140

Ile Gln Pro Lys Ile Arg Gly Phe Ile Cys Thr Thr Thr His Pro Ile
145                 150                 155                 160

Gly Cys Glu Lys Arg Val Gln Glu Glu Ile Ala Tyr Ala Arg Ala His
                165                 170                 175

Pro Pro Thr Ser Pro Gly Pro Lys Arg Val Leu Val Ile Gly Cys Ser
            180                 185                 190

Thr Gly Tyr Gly Leu Ser Thr Arg Ile Thr Ala Ala Phe Gly Tyr Gln
        195                 200                 205

Ala Ala Thr Leu Gly Val Phe Leu Ala Gly Pro Pro Thr Lys Gly Arg
    210                 215                 220

Pro Ala Ala Ala Gly Trp Tyr Asn Thr Val Ala Phe Glu Lys Ala Ala
225                 230                 235                 240

Leu Glu Ala Gly Leu Tyr Ala Arg Ser Leu Asn Gly Asp Ala Phe Asp
                245                 250                 255

Ser Thr Thr Lys Ala Arg Thr Val Glu Ala Ile Lys Arg Asp Leu Gly
            260                 265                 270
```

```
Thr Val Asp Leu Val Val Tyr Ser Ile Ala Ala Pro Lys Arg Thr Asp
        275                 280                 285

Pro Ala Thr Gly Val Leu His Lys Ala Cys Leu Lys Pro Ile Gly Ala
    290                 295                 300

Thr Tyr Thr Asn Arg Thr Val Asn Thr Asp Lys Ala Glu Val Thr Asp
305                 310                 315                 320

Val Ser Ile Glu Pro Ala Ser Pro Glu Glu Ile Ala Asp Thr Val Lys
                325                 330                 335

Val Met Gly Gly Glu Asp Trp Glu Leu Trp Ile Gln Ala Leu Ser Glu
            340                 345                 350

Ala Gly Val Leu Ala Glu Gly Ala Lys Thr Val Ala Tyr Ser Tyr Ile
        355                 360                 365

Gly Pro Glu Met Thr Trp Pro Val Tyr Trp Ser Gly Thr Ile Gly Glu
    370                 375                 380

Ala Lys Lys Asp Val Glu Lys Ala Ala Lys Arg Ile Thr Gln Gln Tyr
385                 390                 395                 400

Gly Cys Pro Ala Tyr Pro Val Val Ala Lys Ala Leu Val Thr Gln Ala
                405                 410                 415

Ser Ser Ala Ile Pro Val Val Pro Leu Tyr Ile Cys Leu Leu Tyr Arg
            420                 425                 430

Val Met Lys Glu Lys Gly Thr His Glu Gly Cys Ile Glu Gln Met Val
        435                 440                 445

Arg Leu Leu Thr Thr Lys Leu Tyr Pro Glu Asn Gly Ala Pro Ile Val
    450                 455                 460

Asp Glu Ala Gly Arg Val Arg Val Asp Asp Trp Glu Met Ala Glu Asp
465                 470                 475                 480

Val Gln Gln Ala Val Lys Asp Leu Trp Ser Gln Val Ser Thr Ala Asn
                485                 490                 495

Leu Lys Asp Ile Ser Asp Phe Ala Gly Tyr Gln Thr Glu Phe Leu Arg
            500                 505                 510

Leu Phe Gly Phe Gly Ile Asp Gly Val Asp Tyr Asp Gln Pro Val Asp
        515                 520                 525

Val Glu Ala Asp Leu Pro Ser Ala Ala Gln Gln
    530                 535
```

<210> SEQ ID NO 148
<211> LENGTH: 1344
<212> TYPE: DNA
<213> ORGANISM: Sreptomyces collinus

<400> SEQUENCE: 148

```
gtgaccgtga aggacatcct ggacgcgatc cagtcgaagg acgccacgtc cgccgacttc      60

gccgccctgc agctccccga gtcgtaccgt gcgatcaccg tgcacaagga cgagacggag     120

atgttcgcgg gtctggagac ccgcgacaag gacccgcgca agtcgatcca cctcgacgag     180

gtgcccgtgc ccgaactggg cccgggcgaa gccctggtgg ccgtcatggc ctcctcggtc     240

aactacaact cggtgtggac ctcgatcttc gagccggtgt cgacgttcgc cttcctggag     300

cgctacggca agctgtcgcc gctgaccaag cgccacgacc tgccgtacca catcatcggc     360

tccgacctcg cgggcgtcgt cctgcgcacc ggccccggcg tcaacgcctg gcagcccggt     420

gacgaggtcg tcgcgcactg cctgagcgtc gagctggagt cgcccgacgg ccacgacgac     480

accatgctcg accccgagca gcgcatctgg ggcttcgaga ccaacttcgg cggcctcgcg     540

gagatcgcgc tggtcaagac gaaccagctg atgccgaagc cgaagcacct cacctgggag     600

gaggccgcgg ccccgggcct ggtgaactcc accgcctacc gccagctggt ctcccgcaac     660
```

```
ggcgccgcca tgaagcaggg cgacaacgtc ctgatctggg gcgcgagcgg cgggctcggc    720

tcgtacgcca cgcagttcgc gctcgcgggc ggtgccaacc cgatctgtgt cgtctcctcg    780

ccccagaagg cggagatctg ccgctcgatg ggcgccgagg cgatcatcga ccgcaacgcc    840

gagggctaca agttctggaa ggacgagcac acccaggacc ccaaggagtg gaagcgcttc    900

ggcaagcgca tccgcgagct gaccggcggc gaggacatcg acatcgtctt cgagcacccc    960

ggccgcgaga ccttcggcgc ctccgtctac gtcacccgca agggcggcac catcaccacc   1020

tgcgcctcga cctcgggcta catgcacgag tacgacaacc ggtacctgtg gatgtccctg   1080

aagcggatca tcggctcgca cttcgccaac taccgcgagg cgtacgaggc caaccgcctg   1140

atcgccaagg gcaagatcca cccgacgctg tcgaagacgt actccctgga ggagaccggc   1200

caggcggcgt acgacgtcca ccgcaacctg caccagggca aggtcggcgt cctgtgcctc   1260

gcgccggagg aaggcctcgg cgtgcgcgac gcggagatgc gcgcccagca catcgacgcc   1320

atcaaccgct tccgcaacgt ctga                                          1344
```

```
<210> SEQ ID NO 149
<211> LENGTH: 447
<212> TYPE: PRT
<213> ORGANISM: Streptomyces collinus

<400> SEQUENCE: 149

Met Thr Val Lys Asp Ile Leu Asp Ala Ile Gln Ser Lys Asp Ala Thr
1               5                   10                  15

Ser Ala Asp Phe Ala Ala Leu Gln Leu Pro Glu Ser Tyr Arg Ala Ile
            20                  25                  30

Thr Val His Lys Asp Glu Thr Glu Met Phe Ala Gly Leu Glu Thr Arg
        35                  40                  45

Asp Lys Asp Pro Arg Lys Ser Ile His Leu Asp Glu Val Pro Val Pro
    50                  55                  60

Glu Leu Gly Pro Gly Glu Ala Leu Val Ala Val Met Ala Ser Ser Val
65                  70                  75                  80

Asn Tyr Asn Ser Val Trp Thr Ser Ile Phe Glu Pro Val Ser Thr Phe
                85                  90                  95

Ala Phe Leu Glu Arg Tyr Gly Lys Leu Ser Pro Leu Thr Lys Arg His
            100                 105                 110

Asp Leu Pro Tyr His Ile Ile Gly Ser Asp Leu Ala Gly Val Val Leu
        115                 120                 125

Arg Thr Gly Pro Gly Val Asn Ala Trp Gln Pro Gly Asp Glu Val Val
    130                 135                 140

Ala His Cys Leu Ser Val Glu Leu Glu Ser Pro Asp Gly His Asp Asp
145                 150                 155                 160

Thr Met Leu Asp Pro Glu Gln Arg Ile Trp Gly Phe Glu Thr Asn Phe
                165                 170                 175

Gly Gly Leu Ala Glu Ile Ala Leu Val Lys Thr Asn Gln Leu Met Pro
            180                 185                 190

Lys Pro Lys His Leu Thr Trp Glu Glu Ala Ala Ala Pro Gly Leu Val
        195                 200                 205

Asn Ser Thr Ala Tyr Arg Gln Leu Val Ser Arg Asn Gly Ala Ala Met
    210                 215                 220

Lys Gln Gly Asp Asn Val Leu Ile Trp Gly Ala Ser Gly Gly Leu Gly
225                 230                 235                 240

Ser Tyr Ala Thr Gln Phe Ala Leu Ala Gly Gly Ala Asn Pro Ile Cys
                245                 250                 255
```

```
Val Val Ser Ser Pro Gln Lys Ala Glu Ile Cys Arg Ser Met Gly Ala
            260                 265                 270

Glu Ala Ile Ile Asp Arg Asn Ala Glu Gly Tyr Lys Phe Trp Lys Asp
        275                 280                 285

Glu His Thr Gln Asp Pro Lys Glu Trp Lys Arg Phe Gly Lys Arg Ile
    290                 295                 300

Arg Glu Leu Thr Gly Gly Glu Asp Ile Asp Ile Val Phe Glu His Pro
305                 310                 315                 320

Gly Arg Glu Thr Phe Gly Ala Ser Val Tyr Val Thr Arg Lys Gly Gly
                325                 330                 335

Thr Ile Thr Thr Cys Ala Ser Thr Ser Gly Tyr Met His Glu Tyr Asp
            340                 345                 350

Asn Arg Tyr Leu Trp Met Ser Leu Lys Arg Ile Ile Gly Ser His Phe
        355                 360                 365

Ala Asn Tyr Arg Glu Ala Tyr Glu Ala Asn Arg Leu Ile Ala Lys Gly
    370                 375                 380

Lys Ile His Pro Thr Leu Ser Lys Thr Tyr Ser Leu Glu Glu Thr Gly
385                 390                 395                 400

Gln Ala Ala Tyr Asp Val His Arg Asn Leu His Gln Gly Lys Val Gly
                405                 410                 415

Val Leu Cys Leu Ala Pro Glu Glu Gly Leu Gly Val Arg Asp Ala Glu
            420                 425                 430

Met Arg Ala Gln His Ile Asp Ala Ile Asn Arg Phe Arg Asn Val
        435                 440                 445


<210> SEQ ID NO 150
<211> LENGTH: 1344
<212> TYPE: DNA
<213> ORGANISM: Streptomyces coelicolor

<400> SEQUENCE: 150

gtgaccgtga aggacatcct ggacgcgatc cagtcgcccg actccacgcc ggccgacatc     60

gccgcactgc cgctccccga gtcgtaccgc gcgatcaccg tgcacaagga cgagaccgag    120

atgttcgcgg gcctcgagac ccgcgacaag gacccccgca agtcgatcca cctggacgac    180

gtgccggtgc ccgagctggg ccccggcgag gccctggtgg ccgtcatggc ctcctcggtc    240

aactacaact cggtgtggac ctcgatcttc gagccgctgt ccaccttcgg gttcctggag    300

cgctacggcc gggtcagcga cctcgccaag cggcacgacc tgccgtacca cgtcatcggc    360

tccgacctcg ccggtgtcgt cctgcgcacc ggtccgggcg tcaacgcctg gcaggcgggc    420

gacgaggtcg tcgcgcactg cctctccgtc gagctggagt cctccgacgg ccacaacgac    480

acgatgctcg accccgagca gcgcatctgg ggcttcgaga ccaacttcgg cggcctcgcg    540

gagatcgcgc tggtcaagtc caaccagctg atgccgaagc cggaccacct gagctgggag    600

gaggccgccg ctcccggcct ggtcaactcc accgcgtacc gccagctcgt ctcccgcaac    660

ggcgccggca tgaagcaggg cgacaacgtg ctcatctggg gcgcgagcgg cggactcggc    720

tcgtacgcca cccagttcgc cctcgccggc ggcgccaacc cgatctgcgt cgtctcctcg    780

ccgcagaagg cggagatctg ccgcgcgatg ggcgccgagg cgatcatcga ccgcaacgcc    840

gagggctacc ggttctggaa ggacgagaac acccaggacc cgaaggagtg gaagcgcttc    900

ggcaagcgca tccgcgaact gaccggcggc gaggacatcg acatcgtctt cgagcacccc    960

ggccgcgaga ccttcggcgc ctccgtcttc gtcacccgca agggcggcac catcaccacc   1020

tgcgcctcga cctcgggcta catgcacgag tacgacaacc gctacctgtg gatgtccctg   1080
```

```
aagcgcatca tcggctcgca cttcgccaac taccgcgagg cctgggaggc caaccgcctc   1140

atcgccaagg gcaggatcca ccccacgctc tccaaggtgt actccctcga ggacaccggc   1200

caggccgcct acgacgtcca ccgcaacctc caccagggca aggtcggcgt gctgtgcctg   1260

gcgcccgagg agggcctggg cgtgcgcgac cgggagaagc gcgcgcagca cctcgacgcc   1320

atcaaccgct tccggaacat ctga                                          1344


<210> SEQ ID NO 151
<211> LENGTH: 447
<212> TYPE: PRT
<213> ORGANISM: Streptomyces coelicolor

<400> SEQUENCE: 151

Met Thr Val Lys Asp Ile Leu Asp Ala Ile Gln Ser Pro Asp Ser Thr
1               5                   10                  15

Pro Ala Asp Ile Ala Ala Leu Pro Leu Pro Glu Ser Tyr Arg Ala Ile
            20                  25                  30

Thr Val His Lys Asp Glu Thr Glu Met Phe Ala Gly Leu Glu Thr Arg
        35                  40                  45

Asp Lys Asp Pro Arg Lys Ser Ile His Leu Asp Asp Val Pro Val Pro
    50                  55                  60

Glu Leu Gly Pro Gly Glu Ala Leu Val Ala Val Met Ala Ser Ser Val
65                  70                  75                  80

Asn Tyr Asn Ser Val Trp Thr Ser Ile Phe Glu Pro Leu Ser Thr Phe
                85                  90                  95

Gly Phe Leu Glu Arg Tyr Gly Arg Val Ser Asp Leu Ala Lys Arg His
            100                 105                 110

Asp Leu Pro Tyr His Val Ile Gly Ser Asp Leu Ala Gly Val Val Leu
        115                 120                 125

Arg Thr Gly Pro Gly Val Asn Ala Trp Gln Ala Gly Asp Glu Val Val
    130                 135                 140

Ala His Cys Leu Ser Val Glu Leu Glu Ser Ser Asp Gly His Asn Asp
145                 150                 155                 160

Thr Met Leu Asp Pro Glu Gln Arg Ile Trp Gly Phe Glu Thr Asn Phe
                165                 170                 175

Gly Gly Leu Ala Glu Ile Ala Leu Val Lys Ser Asn Gln Leu Met Pro
            180                 185                 190

Lys Pro Asp His Leu Ser Trp Glu Glu Ala Ala Ala Pro Gly Leu Val
        195                 200                 205

Asn Ser Thr Ala Tyr Arg Gln Leu Val Ser Arg Asn Gly Ala Gly Met
    210                 215                 220

Lys Gln Gly Asp Asn Val Leu Ile Trp Gly Ala Ser Gly Gly Leu Gly
225                 230                 235                 240

Ser Tyr Ala Thr Gln Phe Ala Leu Ala Gly Gly Ala Asn Pro Ile Cys
                245                 250                 255

Val Val Ser Ser Pro Gln Lys Ala Glu Ile Cys Arg Ala Met Gly Ala
            260                 265                 270

Glu Ala Ile Ile Asp Arg Asn Ala Glu Gly Tyr Arg Phe Trp Lys Asp
        275                 280                 285

Glu Asn Thr Gln Asp Pro Lys Glu Trp Lys Arg Phe Gly Lys Arg Ile
    290                 295                 300

Arg Glu Leu Thr Gly Gly Glu Asp Ile Asp Ile Val Phe Glu His Pro
305                 310                 315                 320

Gly Arg Glu Thr Phe Gly Ala Ser Val Phe Val Thr Arg Lys Gly Gly
```

```
                325                 330                 335

Thr Ile Thr Thr Cys Ala Ser Thr Ser Gly Tyr Met His Glu Tyr Asp
            340                 345                 350

Asn Arg Tyr Leu Trp Met Ser Leu Lys Arg Ile Ile Gly Ser His Phe
        355                 360                 365

Ala Asn Tyr Arg Glu Ala Trp Glu Ala Asn Arg Leu Ile Ala Lys Gly
    370                 375                 380

Arg Ile His Pro Thr Leu Ser Lys Val Tyr Ser Leu Glu Asp Thr Gly
385                 390                 395                 400

Gln Ala Ala Tyr Asp Val His Arg Asn Leu His Gln Gly Lys Val Gly
                405                 410                 415

Val Leu Cys Leu Ala Pro Glu Glu Gly Leu Gly Val Arg Asp Arg Glu
            420                 425                 430

Lys Arg Ala Gln His Leu Asp Ala Ile Asn Arg Phe Arg Asn Ile
        435                 440                 445


<210> SEQ ID NO 152
<211> LENGTH: 2589
<212> TYPE: DNA
<213> ORGANISM: Clostridium acetobutylicum

<400> SEQUENCE: 152

atgaaagtca caacagtaaa ggaattagat gaaaaactca aggtaattaa agaagctcaa      60

aaaaaattct cttgttactc gcaagaaatg gttgatgaaa tctttagaaa tgcagcaatg     120

gcagcaatcg acgcaaggat agagctagca aaagcagctg ttttggaaac cggtatgggc     180

ttagttgaag acaaggttat aaaaaatcat tttgcaggcg aatacatcta taacaaatat     240

aaggatgaaa aaacctgcgg tataattgaa cgaaatgaac cctacggaat tacaaaaata     300

gcagaaccta taggagttgt agctgctata atccctgtaa caaaccccac atcaacaaca     360

atatttaaat ccttaatatc ccttaaaact agaaatggaa ttttcttttc gcctcaccca     420

agggcaaaaa aatccacaat actagcagct aaaacaatac ttgatgcagc cgttaagagt     480

ggtgccccgg aaaatataat aggttggata gatgaacctt caattgaact aactcaatat     540

ttaatgcaaa aagcagatat aacccttgca actggtggtc cctcactagt taaatctgct     600

tattcttccg gaaaaccagc aataggtgtt ggtccgggta acaccccagt aataattgat     660

gaatctgctc atataaaaat ggcagtaagt tcaattatat tatccaaaac ctatgataat     720

ggtgttatat gtgcttctga acaatctgta atagtcttaa aatccatata taacaaggta     780

aaagatgagt tccaagaaag aggagcttat ataataaaga aaaacgaatt ggataaagtc     840

cgtgaagtga tttttaaaga tggatccgta aaccctaaaa tagtcggaca gtcagcttat     900

actatagcag ctatggctgg cataaaagta cctaaaacca caagaatatt aataggagaa     960

gttacctcct taggtgaaga agaacctttt gcccacgaaa aactatctcc tgttttggct    1020

atgtatgagg ctgacaattt tgatgatgct ttaaaaaaag cagtaactct aataaactta    1080

ggaggcctcg gccatacctc aggaatatat gcagatgaaa taaaagcacg agataaaata    1140

gatagattta gtagtgccat gaaaaccgta agaacctttg taaatatccc aacctcacaa    1200

ggtgcaagtg gagatctata taattttaga ataccacctt ctttcacgct tggctgcgga    1260

ttttggggag gaaattctgt ttccgagaat gttggtccaa aacatctttt gaatattaaa    1320

accgtagctg aaaggagaga aaacatgctt tggtttagag ttccacataa agtatatttt    1380

aagttcggtt gtcttcaatt tgctttaaaa gatttaaaag atctaaagaa aaaaagagcc    1440

tttatagtta ctgatagtga cccctataat ttaaactatg ttgattcaat aataaaaata    1500
```

```
cttgagcacc tagatattga ttttaaagta tttaataagg ttggaagaga agctgatctt   1560

aaaaccataa aaaaagcaac tgaagaaatg tcctccttta tgccagacac tataatagct   1620

ttaggtggta cccctgaaat gagctctgca aagctaatgt gggtactata tgaacatcca   1680

gaagtaaaat ttgaagatct tgcaataaaa tttatggaca taagaaagag aatatatact   1740

ttcccaaaac tcggtaaaaa ggctatgtta gttgcaatta caacttctgc tggttccggt   1800

tctgaggtta ctccttttgc tttagtaact gacaataaca ctggaaataa gtacatgtta   1860

gcagattatg aaatgacacc aaatatggca attgtagatg cagaacttat gatgaaaatg   1920

ccaaagggat taaccgctta ttcaggtata gatgcactag taaatagtat agaagcatac   1980

acatccgtat atgcttcaga atacacaaac ggactagcac tagaggcaat acgattaata   2040

tttaaatatt tgcctgaggc ttacaaaaac ggaagaacca atgaaaaagc aagagagaaa   2100

atggctcacg cttcaactat ggcaggtatg gcatccgcta atgcatttct aggtctatgt   2160

cattccatgg caataaaatt aagttcagaa cacaatattc ctagtggcat tgccaatgca   2220

ttactaatag aagaagtaat aaaatttaac gcagttgata atcctgtaaa acaagcccct   2280

tgcccacaat ataagtatcc aaacaccata tttagatatg ctcgaattgc agattatata   2340

aagcttggag gaaatactga tgaggaaaag gtagatctct taattaacaa aatacatgaa   2400

ctaaaaaaag ctttaaatat accaacttca ataaaggatg caggtgtttt ggaggaaaac   2460

ttctattcct cccttgatag aatatctgaa cttgcactag atgatcaatg cacaggcgct   2520

aatcctagat ttcctcttac aagtgagata aaagaaatgt atataaattg ttttaaaaaa   2580

caaccttaa                                                           2589
```

```
<210> SEQ ID NO 153
<211> LENGTH: 862
<212> TYPE: PRT
<213> ORGANISM: Clostridium acetobutylicum

<400> SEQUENCE: 153

Met Lys Val Thr Thr Val Lys Glu Leu Asp Glu Lys Leu Lys Val Ile
1               5                   10                  15

Lys Glu Ala Gln Lys Lys Phe Ser Cys Tyr Ser Gln Glu Met Val Asp
            20                  25                  30

Glu Ile Phe Arg Asn Ala Ala Met Ala Ala Ile Asp Ala Arg Ile Glu
        35                  40                  45

Leu Ala Lys Ala Ala Val Leu Glu Thr Gly Met Gly Leu Val Glu Asp
    50                  55                  60

Lys Val Ile Lys Asn His Phe Ala Gly Glu Tyr Ile Tyr Asn Lys Tyr
65                  70                  75                  80

Lys Asp Glu Lys Thr Cys Gly Ile Ile Glu Arg Asn Glu Pro Tyr Gly
                85                  90                  95

Ile Thr Lys Ile Ala Glu Pro Ile Gly Val Val Ala Ala Ile Ile Pro
            100                 105                 110

Val Thr Asn Pro Thr Ser Thr Thr Ile Phe Lys Ser Leu Ile Ser Leu
        115                 120                 125

Lys Thr Arg Asn Gly Ile Phe Phe Ser Pro His Pro Arg Ala Lys Lys
    130                 135                 140

Ser Thr Ile Leu Ala Ala Lys Thr Ile Leu Asp Ala Ala Val Lys Ser
145                 150                 155                 160

Gly Ala Pro Glu Asn Ile Ile Gly Trp Ile Asp Glu Pro Ser Ile Glu
                165                 170                 175
```

```
Leu Thr Gln Tyr Leu Met Gln Lys Ala Asp Ile Thr Leu Ala Thr Gly
            180                 185                 190

Gly Pro Ser Leu Val Lys Ser Ala Tyr Ser Ser Gly Lys Pro Ala Ile
        195                 200                 205

Gly Val Gly Pro Gly Asn Thr Pro Val Ile Ile Asp Glu Ser Ala His
    210                 215                 220

Ile Lys Met Ala Val Ser Ser Ile Ile Leu Ser Lys Thr Tyr Asp Asn
225                 230                 235                 240

Gly Val Ile Cys Ala Ser Glu Gln Ser Val Ile Val Leu Lys Ser Ile
                245                 250                 255

Tyr Asn Lys Val Lys Asp Glu Phe Gln Glu Arg Gly Ala Tyr Ile Ile
            260                 265                 270

Lys Lys Asn Glu Leu Asp Lys Val Arg Glu Val Ile Phe Lys Asp Gly
        275                 280                 285

Ser Val Asn Pro Lys Ile Val Gly Gln Ser Ala Tyr Thr Ile Ala Ala
    290                 295                 300

Met Ala Gly Ile Lys Val Pro Lys Thr Thr Arg Ile Leu Ile Gly Glu
305                 310                 315                 320

Val Thr Ser Leu Gly Glu Glu Glu Pro Phe Ala His Glu Lys Leu Ser
                325                 330                 335

Pro Val Leu Ala Met Tyr Glu Ala Asp Asn Phe Asp Asp Ala Leu Lys
            340                 345                 350

Lys Ala Val Thr Leu Ile Asn Leu Gly Gly Leu Gly His Thr Ser Gly
        355                 360                 365

Ile Tyr Ala Asp Glu Ile Lys Ala Arg Asp Lys Ile Asp Arg Phe Ser
    370                 375                 380

Ser Ala Met Lys Thr Val Arg Thr Phe Val Asn Ile Pro Thr Ser Gln
385                 390                 395                 400

Gly Ala Ser Gly Asp Leu Tyr Asn Phe Arg Ile Pro Pro Ser Phe Thr
                405                 410                 415

Leu Gly Cys Gly Phe Trp Gly Gly Asn Ser Val Ser Glu Asn Val Gly
            420                 425                 430

Pro Lys His Leu Leu Asn Ile Lys Thr Val Ala Glu Arg Arg Glu Asn
        435                 440                 445

Met Leu Trp Phe Arg Val Pro His Lys Val Tyr Phe Lys Phe Gly Cys
    450                 455                 460

Leu Gln Phe Ala Leu Lys Asp Leu Lys Asp Leu Lys Lys Lys Arg Ala
465                 470                 475                 480

Phe Ile Val Thr Asp Ser Asp Pro Tyr Asn Leu Asn Tyr Val Asp Ser
                485                 490                 495

Ile Ile Lys Ile Leu Glu His Leu Asp Ile Asp Phe Lys Val Phe Asn
            500                 505                 510

Lys Val Gly Arg Glu Ala Asp Leu Lys Thr Ile Lys Lys Ala Thr Glu
        515                 520                 525

Glu Met Ser Ser Phe Met Pro Asp Thr Ile Ile Ala Leu Gly Gly Thr
    530                 535                 540

Pro Glu Met Ser Ser Ala Lys Leu Met Trp Val Leu Tyr Glu His Pro
545                 550                 555                 560

Glu Val Lys Phe Glu Asp Leu Ala Ile Lys Phe Met Asp Ile Arg Lys
                565                 570                 575

Arg Ile Tyr Thr Phe Pro Lys Leu Gly Lys Lys Ala Met Leu Val Ala
            580                 585                 590

Ile Thr Thr Ser Ala Gly Ser Gly Ser Glu Val Thr Pro Phe Ala Leu
        595                 600                 605
```

```
Val Thr Asp Asn Asn Thr Gly Asn Lys Tyr Met Leu Ala Asp Tyr Glu
    610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
                645                 650                 655

Ile Glu Ala Tyr Thr Ser Val Tyr Ala Ser Glu Tyr Thr Asn Gly Leu
            660                 665                 670

Ala Leu Glu Ala Ile Arg Leu Ile Phe Lys Tyr Leu Pro Glu Ala Tyr
        675                 680                 685

Lys Asn Gly Arg Thr Asn Glu Lys Ala Arg Glu Lys Met Ala His Ala
    690                 695                 700

Ser Thr Met Ala Gly Met Ala Ser Ala Asn Ala Phe Leu Gly Leu Cys
705                 710                 715                 720

His Ser Met Ala Ile Lys Leu Ser Ser Glu His Asn Ile Pro Ser Gly
                725                 730                 735

Ile Ala Asn Ala Leu Leu Ile Glu Glu Val Ile Lys Phe Asn Ala Val
            740                 745                 750

Asp Asn Pro Val Lys Gln Ala Pro Cys Pro Gln Tyr Lys Tyr Pro Asn
        755                 760                 765

Thr Ile Phe Arg Tyr Ala Arg Ile Ala Asp Tyr Ile Lys Leu Gly Gly
    770                 775                 780

Asn Thr Asp Glu Glu Lys Val Asp Leu Leu Ile Asn Lys Ile His Glu
785                 790                 795                 800

Leu Lys Lys Ala Leu Asn Ile Pro Thr Ser Ile Lys Asp Ala Gly Val
                805                 810                 815

Leu Glu Glu Asn Phe Tyr Ser Ser Leu Asp Arg Ile Ser Glu Leu Ala
            820                 825                 830

Leu Asp Asp Gln Cys Thr Gly Ala Asn Pro Arg Phe Pro Leu Thr Ser
        835                 840                 845

Glu Ile Lys Glu Met Tyr Ile Asn Cys Phe Lys Lys Gln Pro
    850                 855                 860
```

<210> SEQ ID NO 154
<211> LENGTH: 1164
<212> TYPE: DNA
<213> ORGANISM: Escherichia coli

<400> SEQUENCE: 154

```
atgaacaact ttaatctgca caccccaacc cgcattctgt ttggtaaagg cgcaatcgct      60

ggtttacgcg aacaaattcc tcacgatgct cgcgtattga ttacctacgg cggcggcagc     120

gtgaaaaaaa ccggcgttct cgatcaagtt ctggatgccc tgaaaggcat ggacgtgctg     180

gaatttggcg gtattgagcc aaacccggct tatgaaacgc tgatgaacgc cgtgaaactg     240

gttcgcgaac agaaagtgac tttcctgctg gcggttggcg gcggttctgt actggacggc     300

accaaattta tcgccgcagc ggctaactat ccggaaaata tcgatccgtg gcacattctg     360

caaacgggcg gtaaagagat taaaagcgcc atcccgatgg gctgtgtgct gacgctgcca     420

gcaaccggtt cagaatccaa cgcaggcgcg gtgatctccc gtaaaaccac aggcgacaag     480

caggcgttcc attctgccca tgttcagccg gtatttgccg tgctcgatcc ggtttatacc     540

tacaccctgc cgccgcgtca ggtggctaac ggcgtagtgg acgcctttgt acacaccgtg     600

gaacagtatg ttaccaaacc ggttgatgcc aaaattcagg accgtttcgc agaaggcatt     660

ttgctgacgc taatcgaaga tggtccgaaa gccctgaaag agccagaaaa ctacgatgtg     720
```

```
cgcgccaacg tcatgtgggc ggcgactcag gcgctgaacg gtttgattgg cgctggcgta    780

ccgcaggact gggcaacgca tatgctgggc cacgaactga ctgcgatgca cggtctggat    840

cacgcgcaaa cactggctat cgtcctgcct gcactgtgga atgaaaaacg cgataccaag    900

cgcgctaagc tgctgcaata tgctgaacgc gtctggaaca tcactgaagg ttccgatgat    960

gagcgtattg acgccgcgat tgccgcaacc cgcaatttct ttgagcaatt aggcgtgccg   1020

acccacctct ccgactacgg tctggacggc agctccatcc cggctttgct gaaaaaactg   1080

gaagagcacg gcatgaccca actgggcgaa aatcatgaca ttacgttgga tgtcagccgc   1140

cgtatatacg aagccgcccg ctaa                                          1164


<210> SEQ ID NO 155
<211> LENGTH: 387
<212> TYPE: PRT
<213> ORGANISM: Escherichia coli

<400> SEQUENCE: 155

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
```

```
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385


<210> SEQ ID NO 156
<211> LENGTH: 3883
<212> TYPE: DNA
<213> ORGANISM: Escherichia coli

<400> SEQUENCE: 156

ctatattgct gaaggtacag gcgtttccat aactatttgc tcgcgttttt tactcaagaa     60

gaaaatgcca aatagcaaca tcaggcagac aatacccgaa attgcgaaga aaactgtctg    120

gtagcctgcg tggtcaaaga gtatcccagt cggcgttgaa agcagcacaa tcccaagcga    180

actggcaatt tgaaaaccaa tcagaaagat cgtcgacgac aggcgcttat caaagtttgc    240

cacgctgtat ttgaagacgg atatgacaca aagtggaacc tcaatggcat gtaacaactt    300

cactaatgaa ataatccagg ggttaacgaa cagcgcgcag gaaaggatac gcaacgccat    360

aatcacaact ccgataagta atgcattttt tggccctacc cgattcacaa agaaaggaat    420

aatcgccatg cacagcgctt cgagtaccac ctggaatgag ttgagataac catacaggcg    480

cgttcctaca tcgtgtgatt cgaataaacc tgaataaaag acaggaaaaa gttgttgatc    540

aaaaatgtta tagaaagacc acgtccccac aataaatatg acgaaaaccc agaagtttcg    600

atccttgaaa actgcgataa aatcctcttt ttttacccct cccgcatctg ccgctacgca    660

ctggtgatcc ttatctttaa aacgcatgtt gatcatcata aatacagcgc caaatagcga    720

gaccaaccag aagttgatat ggggactgat actaaaaaat atgccggcaa agaacgcgcc    780

aatagcatag ccaaaagatc cccaggcgcg cgctgttcca tattcgaaat gaaaatttcg    840

cgccattttt tcggtgaagc tatcaagcaa accgcatccc gccagatacc ccaagccaaa    900

aaatagcgcc cccagaatta gacctacaga aaaattgctt tgcagtaacg gttcataaac    960

gtaaatcata aacggtccgg tcaagaccag gatgaaactc atacaccaga tgagcggttt   1020

cttcagaccg agtttatcct gaacgatgcc gtagaacatc ataaatagaa tgctggtaaa   1080

ctggttgacc gaataaagtg tacctaattc cgtccctgtc aaccctagat gtcctttcag   1140

ccaaatagcg tataacgacc accacagcga ccaggaaata aaaaagagaa atgagtaact   1200

ggatgcaaaa cgatagtacg catttctgaa tggaatattc agtgccataa ttacctgcct   1260

gtcgttaaaa aattcacgtc ctatttagag ataagagcga cttcgccgtt tacttctcac   1320

tattccagtt cttgtcgaca tggcagcgct gtcattgccc ctttcgccgt tactgcaagc   1380

gctccgcaac gttgagcgag atcgataatt cgtcgcattt ctctctcatc tgtagataat   1440

cccgtagagg acagacctgt gagtaacccg gcaacgaacg catctcccgc ccccgtgcta   1500

tcgacacaat tcacagacat tccagcaaaa tggtgaactt gtcctcgata acagaccacc   1560
```

```
accccttctg cacctttagt caccaacagc atggcgatct catactcttt tgccagggcg   1620
catatatcct gatcgttctg tgtttttcca ctgataagtc gccattcttc ttccgagagc   1680
ttgacgacat ccgccagttg tagcgcctgc cgcaaacaca agcggagcaa atgctcgtct   1740
tgccatagat cttcacgaat attaggatcg aagctgacaa aacctccggc atgccggatc   1800
gccgtcatcg cagtaaatgc gctggtacgc gaaggctcgg cagacaacgc aattgaacag   1860
agatgtaacc attcgccatg tcgccagcag ggcaagtctg tcgtctctaa aaaaagatcg   1920
gcactggggc ggaccataaa cgtaaatgaa cgttcccctt gatcgttcag atcgacaagc   1980
accgtggatg tccggtgcca ttcatcttgc ttcagatacg tgatatcgac tccctcagtt   2040
agcagcgttc tttgcattaa cgcaccaaaa ggatcatccc ccacccgacc tataaaccca   2100
cttgttccgc ctaatctggc gattcccacc gcaacgttag ctggcgcgcc gccaggacaa   2160
ggcagtaggc gcccgtctga ttctggcaag agatctacga ccgcatcccc taaaacccat   2220
actttggctg acattttttt cccttaaatt catctgagtt acgcatagtg ataaacctct   2280
ttttcgcaaa atcgtcatgg atttactaaa acatgcatat tcgatcacaa aacgtcatag   2340
ttaacgttaa catttgtgat attcatcgca tttatgaaag taagggactt tatttttata   2400
aaagttaacg ttaacaattc accaaatttg cttaaccagg atgattaaaa tgacgcaatc   2460
tcgattgcat gcggcgcaaa acgccctagc aaaacttcat gagcaccggg gtaacacttt   2520
ctatccccat tttcacctcg cgcctcctgc cgggtggatg aacgatccaa acggcctgat   2580
ctggtttaac gatcgttatc acgcgtttta tcaacatcat ccgatgagcg aacactgggg   2640
gccaatgcac tggggacatg ccaccagcga cgatatgatc cactggcagc atgagcctat   2700
tgcgctagcg ccaggagacg ataatgacaa agacgggtgt ttttcaggta gtgctgtcga   2760
tgacaatggt gtcctctcac ttatctacac cggacacgtc tggctcgatg gtgcaggtaa   2820
tgacgatgca attcgcgaag tacaatgtct ggctaccagt cgggatggta ttcatttcga   2880
gaaacagggt gtgatcctca ctccaccaga aggaatcatg cacttccgcg atcctaaagt   2940
gtggcgtgaa gccgacacat ggtggatggt agtcggggcg aaagatccag gcaacacggg   3000
gcagatcctg ctttatcgcg gcagttcgtt gcgtgaatgg accttcgatc gcgtactggc   3060
ccacgctgat gcgggtgaaa gctatatgtg ggaatgtccg gactttttca gccttggcga   3120
tcagcattat ctgatgtttt ccccgcaggg aatgaatgcc gagggataca gttaccgaaa   3180
tcgctttcaa agtggcgtaa tacccggaat gtggtcgcca ggacgacttt ttgcacaatc   3240
cgggcatttt actgaacttg ataacgggca tgacttttat gcaccacaaa gctttttagc   3300
gaaggatggt cggcgtattg ttatcggctg gatggatatg tgggaatcgc caatgccctc   3360
aaaacgtgaa ggatgggcag gctgcatgac gctggcgcgc gagctatcag agagcaatgg   3420
caaacttcta caacgcccgg tacacgaagc tgagtcgtta cgccagcagc atcaatctgt   3480
ctctccccgc acaatcagca ataaatatgt tttgcaggaa aacgcgcaag cagttgagat   3540
tcagttgcag tgggcgctga agaacagtga tgccgaacat tacggattac agctcggcac   3600
tggaatgcgg ctgtatattg ataaccaatc tgagcgactt gttttgtggc ggtattaccc   3660
acacgagaat ttagacggct accgtagtat tcccctcccg cagcgtgaca cgctcgccct   3720
aaggatattt atcgatacat catccgtgga agtatttatt aacgacgggg aagcggtgat   3780
gagtagtcga atctatccgc agccagaaga acgggaactg tcgctttatg cctcccacgg   3840
agtggctgtg ctgcaacatg gagcactctg gctactgggt taa                     3883
```

<210> SEQ ID NO 157

<211> LENGTH: 477
<212> TYPE: PRT
<213> ORGANISM: Escherichia coli

<400> SEQUENCE: 157

```
Met Thr Gln Ser Arg Leu His Ala Ala Gln Asn Ala Leu Ala Lys Leu
1               5                   10                  15

His Glu His Arg Gly Asn Thr Phe Tyr Pro His Phe His Leu Ala Pro
            20                  25                  30

Pro Ala Gly Trp Met Asn Asp Pro Asn Gly Leu Ile Trp Phe Asn Asp
        35                  40                  45

Arg Tyr His Ala Phe Tyr Gln His His Pro Met Ser Glu His Trp Gly
    50                  55                  60

Pro Met His Trp Gly His Ala Thr Ser Asp Asp Met Ile His Trp Gln
65                  70                  75                  80

His Glu Pro Ile Ala Leu Ala Pro Gly Asp Asp Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125

Arg Glu Val Gln Cys Leu Ala Thr Ser Arg Asp Gly Ile His Phe Glu
    130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Trp Met Val Val Gly
                165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
        195                 200                 205

Gly Glu Ser Tyr Met Trp Glu Cys Pro Asp Phe Phe Ser Leu Gly Asp
    210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Leu Ala Lys Asp Gly Arg
        275                 280                 285

Arg Ile Val Ile Gly Trp Met Asp Met Trp Glu Ser Pro Met Pro Ser
    290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
                325                 330                 335

Leu Arg Gln Gln His Gln Ser Val Ser Pro Arg Thr Ile Ser Asn Lys
            340                 345                 350

Tyr Val Leu Gln Glu Asn Ala Gln Ala Val Glu Ile Gln Leu Gln Trp
        355                 360                 365

Ala Leu Lys Asn Ser Asp Ala Glu His Tyr Gly Leu Gln Leu Gly Thr
    370                 375                 380

Gly Met Arg Leu Tyr Ile Asp Asn Gln Ser Glu Arg Leu Val Leu Trp
385                 390                 395                 400
```

```
Arg Tyr Tyr Pro His Glu Asn Leu Asp Gly Tyr Arg Ser Ile Pro Leu
                405                 410                 415

Pro Gln Arg Asp Thr Leu Ala Leu Arg Ile Phe Ile Asp Thr Ser Ser
            420                 425                 430

Val Glu Val Phe Ile Asn Asp Gly Glu Ala Val Met Ser Ser Arg Ile
        435                 440                 445

Tyr Pro Gln Pro Glu Glu Arg Glu Leu Ser Leu Tyr Ala Ser His Gly
    450                 455                 460

Val Ala Val Leu Gln His Gly Ala Leu Trp Leu Leu Gly
465                 470                 475


<210> SEQ ID NO 158
<211> LENGTH: 304
<212> TYPE: PRT
<213> ORGANISM: Escherichia coli

<400> SEQUENCE: 158

Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Glu Trp Arg
            180                 185                 190

Leu Ile Ser Gly Lys Thr Gln Asn Asp Gln Asp Ile Cys Ala Leu Ala
        195                 200                 205

Lys Glu Tyr Glu Ile Ala Met Leu Leu Val Thr Lys Gly Ala Glu Gly
    210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
        275                 280                 285

Thr Ala Lys Gly Ala Met Thr Ala Leu Pro Cys Arg Gln Glu Leu Glu
    290                 295                 300
```

<210> SEQ ID NO 159
<211> LENGTH: 415
<212> TYPE: PRT
<213> ORGANISM: Escherichia coli

<400> SEQUENCE: 159

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
    370                 375                 380
```

```
Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415


<210> SEQ ID NO 160
<211> LENGTH: 18
<212> TYPE: DNA
<213> ORGANISM: Artificial Sequence
<220> FEATURE:
<223> OTHER INFORMATION: Primer Scr1

<400> SEQUENCE: 160

cctttctttg tgaatcgg                                                     18


<210> SEQ ID NO 161
<211> LENGTH: 18
<212> TYPE: DNA
<213> ORGANISM: Artificial Sequence
<220> FEATURE:
<223> OTHER INFORMATION: Primer Scr2

<400> SEQUENCE: 161

agaaacaggg tgtgatcc                                                     18


<210> SEQ ID NO 162
<211> LENGTH: 20
<212> TYPE: DNA
<213> ORGANISM: Artificial Sequence
<220> FEATURE:
<223> OTHER INFORMATION: Primer Scr3

<400> SEQUENCE: 162

agtgatcatc acctgttgcc                                                   20


<210> SEQ ID NO 163
<211> LENGTH: 20
<212> TYPE: DNA
<213> ORGANISM: Artificial Sequence
<220> FEATURE:
<223> OTHER INFORMATION: Primer Scr4

<400> SEQUENCE: 163

agcacggcga gagtcgacgg                                                   20


<210> SEQ ID NO 164
<211> LENGTH: 74
<212> TYPE: DNA
<213> ORGANISM: Artificial Sequence
<220> FEATURE:
<223> OTHER INFORMATION: Primer OT731

<400> SEQUENCE: 164

aaagctggag ctccaccgcg gtggcggccg ctctagaagt tttcaaagca gagtttcgtt       60

tgaatatttt acca                                                         74


<210> SEQ ID NO 165
<211> LENGTH: 50
<212> TYPE: DNA
<213> ORGANISM: Artificial Sequence
<220> FEATURE:
<223> OTHER INFORMATION: Primer OT732

<400> SEQUENCE: 165

ttcaatatgc atgcctcaga acgtttacat tgtatcgact gccagaaccc                  50
```

<210> SEQ ID NO 166
<211> LENGTH: 79
<212> TYPE: DNA
<213> ORGANISM: Artificial Sequence
<220> FEATURE:
<223> OTHER INFORMATION: Primer OT733

<400> SEQUENCE: 166
gcagtcgata caatgtaaac gttctgaggc atgcatattg aattttcaaa aattcttact 60 tttttttgg atggacgca 79

<210> SEQ ID NO 167
<211> LENGTH: 72
<212> TYPE: DNA
<213> ORGANISM: Artificial Sequence
<220> FEATURE:
<223> OTHER INFORMATION: Primer OT734

<400> SEQUENCE: 167
acctgcacct ataacacata ccttttccat ggtagttttt tctccttgac gttaaagtat 60
agaggtatat ta 72

<210> SEQ ID NO 168
<211> LENGTH: 60
<212> TYPE: DNA
<213> ORGANISM: Artificial Sequence
<220> FEATURE:
<223> OTHER INFORMATION: Primer OT735

<400> SEQUENCE: 168
aaaaactacc atggaaaagg tatgtgttat aggtgcaggt actatgggtt caggaattgc 60

<210> SEQ ID NO 169
<211> LENGTH: 71
<212> TYPE: DNA
<213> ORGANISM: Artificial Sequence
<220> FEATURE:
<223> OTHER INFORMATION: Primer OT736

<400> SEQUENCE: 169
gtaaaaaaaa gaaggccgta taggccttat tttgaataat cgtagaaacc ttttcctgat 60
tttcttccaa g 71

<210> SEQ ID NO 170
<211> LENGTH: 81
<212> TYPE: DNA
<213> ORGANISM: Artificial Sequence
<220> FEATURE:
<223> OTHER INFORMATION: Primer OT737

<400> SEQUENCE: 170
acgattattc aaaataaggc ctatacggcc ttcttttttt tactttgttc agaacaactt 60
ctcatttttt tctactcata a 81

<210> SEQ ID NO 171
<211> LENGTH: 73
<212> TYPE: DNA
<213> ORGANISM: Artificial Sequence
<220> FEATURE:
<223> OTHER INFORMATION: Primer OT738

<400> SEQUENCE: 171
gaattgggta ccgggccccc cctcgaggtc gaccgatgcc tcataaactt cggtagttat 60
attactctga gat 73

<210> SEQ ID NO 172
<211> LENGTH: 65
<212> TYPE: DNA
<213> ORGANISM: Artificial Sequence
<220> FEATURE:
<223> OTHER INFORMATION: Primer OT797

<400> SEQUENCE: 172
aaagtaagaa tttttgaaaa ttcaatatgc atgcaagaag ttgtaatagc tagtgcagta 60
agaac 65

<210> SEQ ID NO 173
<211> LENGTH: 73
<212> TYPE: DNA
<213> ORGANISM: Artificial Sequence
<220> FEATURE:
<223> OTHER INFORMATION: Primer OT798

<400> SEQUENCE: 173
gaaaaagatc atgagaaaat cgcagaacgt aaggcgcgcc tcagcacttt tctagcaata 60
ttgctgttcc ttg 73

<210> SEQ ID NO 174
<211> LENGTH: 41
<212> TYPE: DNA
<213> ORGANISM: Artificial Sequence
<220> FEATURE:
<223> OTHER INFORMATION: Primer OT806

<400> SEQUENCE: 174
ctcgaaaata gggcgcgccc ccattaccga catttgggcg c 41

<210> SEQ ID NO 175
<211> LENGTH: 55
<212> TYPE: DNA
<213> ORGANISM: Artificial Sequence
<220> FEATURE:
<223> OTHER INFORMATION: Primer OT807

<400> SEQUENCE: 175
actgcactag ctattacaac ttcttgcatg cgtgatgatt gattgattga ttgta 55

<210> SEQ ID NO 176
<211> LENGTH: 55
<212> TYPE: DNA
<213> ORGANISM: Artificial Sequence
<220> FEATURE:
<223> OTHER INFORMATION: Primer OT808

<400> SEQUENCE: 176
actgcactag ctattacaac ttcttgcatg cgtgatgatt gattgattga ttgta 55

<210> SEQ ID NO 177
<211> LENGTH: 60
<212> TYPE: DNA
<213> ORGANISM: Artificial Sequence
<220> FEATURE:
<223> OTHER INFORMATION: Primer OT809

<400> SEQUENCE: 177
tttcgaataa acacacataa acaaacaccc catggaaaag gtatgtgtta taggtgcagg 60

<210> SEQ ID NO 178
<211> LENGTH: 62
<212> TYPE: DNA
<213> ORGANISM: Artificial Sequence
<220> FEATURE:
<223> OTHER INFORMATION: Primer OT799

<400> SEQUENCE: 178
taccgggccc cccctcgagg tcgacggcgc gccactggta gagagcgact ttgtatgccc 60
ca 62

<210> SEQ ID NO 179
<211> LENGTH: 60
<212> TYPE: DNA
<213> ORGANISM: Artificial Sequence
<220> FEATURE:
<223> OTHER INFORMATION: Primer OT761

<400> SEQUENCE: 179
cttggccttc actagcatgc tgaatatgta ttacttggtt atggttatat atgacaaaag 60

<210> SEQ ID NO 180
<211> LENGTH: 68
<212> TYPE: DNA
<213> ORGANISM: Artificial Sequence
<220> FEATURE:
<223> OTHER INFORMATION: Primer OT803

<400> SEQUENCE: 180
ccctcactaa agggaacaaa agctggagct cgatatcggc gcgcccacat gcagtgatgc 60
acgcgcga 68

<210> SEQ ID NO 181
<211> LENGTH: 49
<212> TYPE: DNA
<213> ORGANISM: Artificial Sequence
<220> FEATURE:
<223> OTHER INFORMATION: Primer OT804

<400> SEQUENCE: 181
aaggatgaca ttgtttagtt ccatggttgt aatatgtgtg tttgtttgg 49

<210> SEQ ID NO 182
<211> LENGTH: 51
<212> TYPE: DNA
<213> ORGANISM: Artificial Sequence
<220> FEATURE:
<223> OTHER INFORMATION: Primer OT785

<400> SEQUENCE: 182
cacacatatt acaaccatgg aactaaacaa tgtcatcctt gaaaaggaag g 51

<210> SEQ ID NO 183
<211> LENGTH: 63
<212> TYPE: DNA
<213> ORGANISM: Artificial Sequence
<220> FEATURE:
<223> OTHER INFORMATION: Primer OT786

<400> SEQUENCE: 183
atcattcatt ggccattcag gccttatcta tttttgaagc cttcaatttt tcttttctct 60
atg 63

<210> SEQ ID NO 184
<211> LENGTH: 65

<212> TYPE: DNA
<213> ORGANISM: Artificial Sequence
<220> FEATURE:
<223> OTHER INFORMATION: Primer OT787

<400> SEQUENCE: 184
caaaaataga taaggcctga atggccaatg aatgatttga tgatttcttt ttccctccat 60
ttttc 65

<210> SEQ ID NO 185
<211> LENGTH: 77
<212> TYPE: DNA
<213> ORGANISM: Artificial Sequence
<220> FEATURE:
<223> OTHER INFORMATION: Primer PT805

<400> SEQUENCE: 185
gaattgggta ccgggccccc cctcgaggtc gacttatagt attatatttt ctgatttggt 60
tatagcaagc agcgttt 77

<210> SEQ ID NO 186
<211> LENGTH: 1269
<212> TYPE: DNA
<213> ORGANISM: Artificial Sequence
<220> FEATURE:
<223> OTHER INFORMATION: Codon optimized ter

<400> SEQUENCE: 186
actagtacca taaccaagta atacatattc agcatgctag tgaaggccaa gttcgtcaag 60
ggctttatta gagatgttca tccgtatggg tgtaggagag aagtgttaaa ccagattgac 120
tactgcaaga aagcaattgg ctttaggggc cctaaaaagg ttcttattgt aggtgcttct 180
tcaggcttcg gactagctac tagaatatct gttgcattcg gagggcctga agcccataca 240
atcggtgttt catacgagac tggagctaca gacagaagga taggtacggc tgggtggtac 300
aataatatct tctttaaaga attcgctaag aagaaaggtt tggtggcaaa gaatttcata 360
gaagatgcat tttcgaatga aaccaaggat aaagtgataa agtatataaa ggacgaattt 420
ggtaaaattg atttattcgt atattcttta gctgctccta gaagaaagga ctacaaaacc 480
ggtaatgttt atacctcaag aattaaaaca attctaggtg actttgaagg gcctactatt 540
gacgtagaaa gagatgaaat aactttaaag aaggtatctt ctgctagtat cgaggaaatc 600
gaagaaacac gtaaagtaat gggcggagaa gactggcagg agtggtgtga ggagttatta 660
tacgaagatt gtttttctga taaagctaca accatcgctt attcctatat tggcagtcct 720
agaacttata aaatatatcg tgaaggaacc attgggattg ctaagaagga tttagaagac 780
aaagccaagt tgatcaacga aaagcttaat agagtcatag gaggtagggc atttgtgtct 840
gttaacaaag ctttagtaac caaggcatct gcttatattc caaccttccc tctatacgct 900
gccatattat ataaagtaat gaaagaaaag aacattcacg aaaattgtat tatgcaaatt 960
gagcgtatgt tctcagagaa aatatactcc aacgaaaaga ttcagttcga tgataagggc 1020
cgtcttagaa tggacgattt agaactaaga aaggatgttc aggatgaagt tgacagaatt 1080
tggtctaaca taacaccaga aaacttcaag gagcttagtg actacaaggg gtataagaaa 1140
gagtttatga atctaaatgg ttttgattta gatggagttg attattccaa ggatcttgat 1200
attgaattac ttagaaaact agagccttaa gcggccgcgt taattcaaat taattgatat 1260
agtactagt 1269

<210> SEQ ID NO 187
<211> LENGTH: 398
<212> TYPE: PRT
<213> ORGANISM: Artificial Sequence
<220> FEATURE:
<223> OTHER INFORMATION: Modified Ter protein

<400> SEQUENCE: 187

```
Met Leu Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380
```

```
Ser Lys Asp Leu Asp Ile Glu Leu Leu Arg Lys Leu Glu Pro
385                 390                 395
```

<210> SEQ ID NO 188
<211> LENGTH: 1484
<212> TYPE: DNA
<213> ORGANISM: Artificial Sequence
<220> FEATURE:
<223> OTHER INFORMATION: Codon optimized ald

<400> SEQUENCE: 188

```
actagttcga ataaacacac ataaacaaac accatggata aagatacctt aatcccaacc     60

accaaagact tgaaagtgaa gactaatggt gaaaacatca acttaaagaa ttacaaagat    120

aactcttcat gttttggagt atttgaaaat gttgagaatg ccatttcttc tgcagtacat    180

gcacaaaaga ttctttccct acactacaca aaggaacaaa gagagaaaat aatcaccgaa    240

ataagaaaag ccgcattaca gaataaagag gtcttagcca caatgatcct ggaggaaacc    300

cacatgggaa ggtatgagga taaaatcttg aaacatgaat tagtggccaa gtatacccca    360

ggcactgaag atctgacaac aacagcatgg tccggcgata atggactaac agtggttgaa    420

atgagtccat acggagttat cggcgctata actccaagca cgaatccaac agaaaccgtt    480

atctgcaatt ctataggtat gatagctgcg gggaatgcag ttgtatttaa tggtcaccca    540

tgcgccaaaa agtgtgtcgc tttcgcagta gaaatgataa acaaagccat aattagctgt    600

ggtggacctg aaaaccttgt cactactata aagaacccaa ctatggaaag tttagacgct    660

attatcaaac atccatccat aaaattgttg tgcggtacgg gtggcccggg tatggtaaaa    720

acccttctta attctggtaa aaaggccatc ggagctggcg cgggtaatcc tccggttatt    780

gtagacgata cagcagatat cgagaaggcc ggcagaagca ttattgaagg ttgttcgttt    840

gacaacaatc ttccttgtat cgcggaaaaa gaagtgttcg tgtttgaaaa cgttgcagat    900

gatctgatct ctaacatgtt gaaaaacaac gccgtcatta tcaatgaaga ccaagtatcc    960

aagctgatag accttgttct tcaaaagaac aatgaaactc aagaatattt cattaataag   1020

aagtgggttg gtaaggacgc taaactgttt ttggatgaaa tagatgtaga gtcaccaagt   1080

aatgtaaagt gtattatttg tgaagtcaac gcaaaccatc cgttcgttat gacggagttg   1140

atgatgccaa ttttgcctat agttagagtg aaggacattg atgaagccat taaatacgcc   1200

aagatagctg agcagaatag aaaacattcc gcctacattt attctaagaa catcgataac   1260

cttaatagat tcgaacgtga aattgataca actatctttg ttaagaatgc aaagtcattt   1320

gcaggtgtcg gttatgaagc tgagggtttc acaaccttta caattgccgg atccacaggt   1380

gaaggaatca cgtcagctag aaactttacc aggcaaagac gttgtgtcct agcaggttag   1440

ggcctgcagg gccgtgaatt tactttaaat cttgcattac tagt                     1484
```

<210> SEQ ID NO 189
<211> LENGTH: 468
<212> TYPE: PRT
<213> ORGANISM: Artificial
<220> FEATURE:
<223> OTHER INFORMATION: Modified Ald

<400> SEQUENCE: 189

```
Met Asp Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30
```

```
Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460
```

Val Leu Ala Gly
465

<210> SEQ ID NO 190
<211> LENGTH: 69
<212> TYPE: DNA
<213> ORGANISM: Artificial Sequence
<220> FEATURE:
<223> OTHER INFORMATION: Primer PT800

<400> SEQUENCE: 190
gggaacaaaa gctggagctc caccgcggtg gggcgcgccc tattttcgag gaccttgtca 60
ccttgagcc 69

<210> SEQ ID NO 191
<211> LENGTH: 50
<212> TYPE: DNA
<213> ORGANISM: Artificial Sequence
<220> FEATURE:
<223> OTHER INFORMATION: Primer OT758

<400> SEQUENCE: 191
ttaaggtatc tttatccatg gtgtttgttt atgtgtgttt attcgaaact 50

<210> SEQ ID NO 192
<211> LENGTH: 52
<212> TYPE: DNA
<213> ORGANISM: Artificial Sequence
<220> FEATURE:
<223> OTHER INFORMATION: Primer OT754

<400> SEQUENCE: 192
ttgggtaccg ggcccccct cgaggtcgac tggccattaa tctttcccat at 52

<210> SEQ ID NO 193
<211> LENGTH: 52
<212> TYPE: DNA
<213> ORGANISM: Artificial Sequence
<220> FEATURE:
<223> OTHER INFORMATION: Primer OT755

<400> SEQUENCE: 193
tgtgtcctag caggttaggg cctgcagggc cgtgaattta ctttaaatct tg 52

<210> SEQ ID NO 194
<211> LENGTH: 50
<212> TYPE: DNA
<213> ORGANISM: Artificial Sequence
<220> FEATURE:
<223> OTHER INFORMATION: Primer OT760

<400> SEQUENCE: 194
cgaaaatagg gcgcgccact ggtagagagc gactttgtat gccccaattg 50

<210> SEQ ID NO 195
<211> LENGTH: 71
<212> TYPE: DNA
<213> ORGANISM: Artificial Sequence
<220> FEATURE:
<223> OTHER INFORMATION: Primer OT792

<400> SEQUENCE: 195
cccttgacga acttggcctt cactagcatg ctgaatatgt attacttggt tatggttata 60
tatgacaaaa g 71

```
<210> SEQ ID NO 196
<211> LENGTH: 71
<212> TYPE: DNA
<213> ORGANISM: Artificial Sequence
<220> FEATURE:
<223> OTHER INFORMATION: Primer OT791

<400> SEQUENCE: 196

cccttgacga acttggcctt cactagcatg ctgaatatgt attacttggt tatggttata     60

tatgacaaaa g                                                          71


<210> SEQ ID NO 197
<211> LENGTH: 73
<212> TYPE: DNA
<213> ORGANISM: Artificial Sequence
<220> FEATURE:
<223> OTHER INFORMATION: Primer OT765

<400> SEQUENCE: 197

ggaacaaaag ctggagctcc accgcggtgg tttaacgtat agacttctaa tatatttctc     60

catacttggt att                                                        73


<210> SEQ ID NO 198
<211> LENGTH: 29
<212> TYPE: DNA
<213> ORGANISM: Artificial Sequence
<220> FEATURE:
<223> OTHER INFORMATION: Primer LDHEcoRV F

<400> SEQUENCE: 198

gacgtcatga ccacccgccg atccctttt                                       29


<210> SEQ ID NO 199
<211> LENGTH: 30
<212> TYPE: DNA
<213> ORGANISM: Artificial Sequence
<220> FEATURE:
<223> OTHER INFORMATION: Primer LDH AatlR

<400> SEQUENCE: 199

gatatccaac accagcgacc gacgtattac                                      30


<210> SEQ ID NO 200
<211> LENGTH: 47
<212> TYPE: DNA
<213> ORGANISM: Artificial Sequence
<220> FEATURE:
<223> OTHER INFORMATION: Primer Cm F

<400> SEQUENCE: 200

atttaaatct cgagtagagg atcccaacaa acgaaaattg gataaag                   47


<210> SEQ ID NO 201
<211> LENGTH: 29
<212> TYPE: DNA
<213> ORGANISM: Artificial Sequence
<220> FEATURE:
<223> OTHER INFORMATION: Primer Cm R

<400> SEQUENCE: 201

acgcgttatt ataaaagcca gtcattagg                                       29


<210> SEQ ID NO 202
<211> LENGTH: 62
<212> TYPE: DNA
```

<213> ORGANISM: Artificial Sequence
<220> FEATURE:
<223> OTHER INFORMATION: Primer P11 F

<400> SEQUENCE: 202
tcgagagcgc tatagttgtt gacagaatgg acatactatg atatattgtt gctatagcgc 60
cc 62

<210> SEQ ID NO 203
<211> LENGTH: 58
<212> TYPE: DNA
<213> ORGANISM: Artificial Sequence
<220> FEATURE:
<223> OTHER INFORMATION: Primer P11 R

<400> SEQUENCE: 203
gggcgctata gcaacaatat atcatagtat gtccattctg tcaacaacta tagcgctc 58

<210> SEQ ID NO 204
<211> LENGTH: 38
<212> TYPE: DNA
<213> ORGANISM: Artificial Sequence
<220> FEATURE:
<223> OTHER INFORMATION: Primer PldhL F

<400> SEQUENCE: 204
gagctcgtcg acaaaccaac attatgacgt gtctgggc 38

<210> SEQ ID NO 205
<211> LENGTH: 30
<212> TYPE: DNA
<213> ORGANISM: Artificial Sequence
<220> FEATURE:
<223> OTHER INFORMATION: Primer PldhL R

<400> SEQUENCE: 205
ggatcctacc atgtttgtgc aaaataagtg 30

<210> SEQ ID NO 206
<211> LENGTH: 34
<212> TYPE: DNA
<213> ORGANISM: Artificial Sequence
<220> FEATURE:
<223> OTHER INFORMATION: Primer F-PnisA (EcoRV)

<400> SEQUENCE: 206
ttcagtgata tcgacatact tgaatgacct agtc 34

<210> SEQ ID NO 207
<211> LENGTH: 48
<212> TYPE: DNA
<213> ORGANISM: Artificial Sequence
<220> FEATURE:
<223> OTHER INFORMATION: Primer R-PnisA(PmeI BamHI)

<400> SEQUENCE: 207
ttgattagtt taaactgtag gatcctttga gtgcctcctt ataattta 48

<210> SEQ ID NO 208
<211> LENGTH: 2460
<212> TYPE: DNA
<213> ORGANISM: Artificial Sequence
<220> FEATURE:
<223> OTHER INFORMATION: Template DNA

<400> SEQUENCE: 208

-continued

```
tgatccaaag gagggtgagg aaatggcgat gtttacgacc accgcaaaag ttattcagcc     60
gaaaattcgt ggttttattt gcaccaccac ccacccgatt ggttgcgaaa aacgtgttca    120
ggaagaaatc gcatacgcac gcgcgcaccc gccgaccagc ccgggtccga aacgtgtgct    180
ggttattggc tgcagtacgg gctatggcct gagcacccgt atcaccgcgg cctttggtta    240
tcaggccgca accctgggcg tgtttctggc aggcccgccg accaaaggcc gtccggccgc    300
ggcgggttgg tataatacgg ttgcgttcga aaaagccgcc ctggaagcag gtctgtatgc    360
acgttctctg aatggtgatg cgttcgattc taccacgaaa gcccgcaccg tggaagcaat    420
taaacgtgat ctgggtaccg ttgatctggt ggtgtatagc attgcagcgc cgaaacgtac    480
cgatccggcc accggcgtgc tgcataaagc gtgcctgaaa ccgattggtg caacctacac    540
caatcgtacg gtgaacaccg ataaagcaga agttaccgat gtgagtattg aaccggccag    600
tccggaagaa atcgcagata ccgtgaaagt tatgggtggc gaagattggg aactgtggat    660
tcaggcactg agcgaagccg gcgtgctggc cgaaggcgca aaaaccgttg cgtattctta    720
tattggcccg gaaatgacgt ggccggtgta ttggagtggc accattggcg aagccaaaaa    780
agatgttgaa aaagcggcga aacgcatcac ccagcagtac ggctgtccgg cgtatccggt    840
tgttgccaaa gcgctggtga cccaggccag tagcgccatt ccggtggtgc cgctgtatat    900
ttgcctgctg tatcgtgtta tgaaagaaaa aggcacccat gaaggctgca ttgaacagat    960
ggtgcgtctg ctgacgacga aactgtatcc ggaaaatggt gcgccgatcg tggatgaagc   1020
gggccgtgtg cgtgttgatg attgggaaat ggcagaagat gttcagcagg cagttaaaga   1080
tctgtggagc caggtgagta cggccaatct gaaagatatt agcgattttg caggttatca   1140
gaccgaattt ctgcgtctgt ttggctttgg tattgatggt gtggattacg atcagccggt   1200
tgatgttgaa gcggatctgc cgagcgccgc ccagcagtaa gtcaacaaag gaggggttaa   1260
aatggttgat ttcgaatatt caataccaac tagaattttt ttcggtaaag ataagataaa   1320
tgtacttgga agagagctta aaaaatatgg ttctaaagtg cttatagttt atggtggagg   1380
aagtataaag agaaatggaa tatatgataa agctgtaagt atacttgaaa aaaacagtat   1440
taaattttat gaacttgcag gagtagagcc aaatccaaga gtaactacag ttgaaaaagg   1500
agttaaaata tgtagagaaa atggagttga agtagtacta gctataggtg gaggaagtgc   1560
aatagattgc gcaaaggtta tagcagcagc atgtgaatat gatggaaatc catgggatat   1620
tgtgttagat ggctcaaaaa taaaaagggt gcttcctata gctagtatat taaccattgc   1680
tgcaacagga tcagaaatgg atacgtgggc agtaataaat aatatggata caaacgaaaa   1740
actaattgcg gcacatccag atatggctcc taagttttct atattagatc caacgtatac   1800
gtataccgta cctaccaatc aaacagcagc aggaacagct gatattatga gtcatatatt   1860
tgaggtgtat tttagtaata caaaaaacagc atatttgcag gatagaatgg cagaagcgtt   1920
attaagaact tgtattaaat atggaggaat agctcttgag aagccggatg attatgaggc   1980
aagagccaat ctaatgtggg cttcaagtct tgcgataaat ggacttttaa catatggtaa   2040
agacactaat tggagtgtac acttaatgga acatgaatta agtgcttatt acgacataac   2100
acacggcgta gggcttgcaa ttttaacacc taattggatg gagtatattt taaataatga   2160
tacagtgtac aagtttgttg aatatggtgt aaatgtttgg ggaatagaca aagaaaaaaa   2220
tcactatgac atagcacatc aagcaataca aaaaacaaga gattactttg taaatgtact   2280
```

-continued

```
aggtttacca tctagactga gagatgttgg aattgaagaa gaaaaattgg acataatggc   2340

aaaggaatca gtaaagctta caggaggaac cataggaaac ctaagaccag taaacgcctc   2400

cgaagtccta caaatattca aaaaatctgt gtaaacctac gtttaaactt acgcgtatga   2460
```